US008247438B2

(12) United States Patent
Elkashef

(10) Patent No.: US 8,247,438 B2
(45) Date of Patent: Aug. 21, 2012

(54) METHODS FOR TREATING SCHIZOPHRENIA

(75) Inventor: Ahmed Elkashef, Dunn Loring, VA (US)

(73) Assignee: Neuropill, Inc., Dunn Loring, VA (US)

( * ) Notice: Subject to any disclaimer, the term of this patent is extended or adjusted under 35 U.S.C. 154(b) by 1061 days.

(21) Appl. No.: 12/136,099

(22) Filed: Jun. 10, 2008

(65) Prior Publication Data

US 2009/0215840 A1 Aug. 27, 2009

Related U.S. Application Data

(60) Provisional application No. 61/032,010, filed on Feb. 27, 2008, provisional application No. 61/038,451, filed on Mar. 21, 2008.

(51) Int. Cl.
| | | |
|---|---|---|
| *A01N 43/78* | (2006.01) | |
| *A01N 43/26* | (2006.01) | |
| *A01N 43/06* | (2006.01) | |
| *A01N 47/28* | (2006.01) | |
| *A61K 31/425* | (2006.01) | |
| *A61K 31/385* | (2006.01) | |
| *A61K 31/38* | (2006.01) | |
| *A61K 31/17* | (2006.01) | |

(52) U.S. Cl. ......... 514/365; 514/439; 514/448; 514/596
(58) Field of Classification Search .................. None
See application file for complete search history.

(56) References Cited

U.S. PATENT DOCUMENTS

| | | | | |
|---|---|---|---|---|
| 5,340,802 | A * | 8/1994 | Shiosaki et al. ............. | 514/12.6 |
| 5,610,144 | A * | 3/1997 | Capet et al. .................. | 514/12.3 |
| 5,624,939 | A | 4/1997 | Capet et al. | |
| 5,633,270 | A | 5/1997 | Dubroeucq et al. | |
| 5,637,602 | A | 6/1997 | Capet et al. | |
| 5,935,980 | A | 8/1999 | Imperato | |
| 6,150,387 | A | 11/2000 | Bohme et al. | |
| 6,380,230 | B1 | 4/2002 | Brodin et al. | |
| 6,410,516 | B1 | 6/2002 | Baltimore et al. | |
| 6,512,120 | B1 | 1/2003 | Mishra et al. | |
| 6,558,708 | B1 | 5/2003 | Lin | |
| 7,081,239 | B2 | 7/2006 | Lin | |

FOREIGN PATENT DOCUMENTS

| | | |
|---|---|---|
| WO | 9301167 A1 | 1/1993 |
| WO | 93/12791 A1 | 7/1993 |
| WO | 94/15914 A1 | 7/1994 |
| WO | 94/15954 A1 | 7/1994 |
| WO | 94/15955 A1 | 7/1994 |
| WO | 96/38139 A1 | 5/1996 |
| WO | 0056296 A2 | 9/2000 |

OTHER PUBLICATIONS

Crawley, "Cholecystokinin-dopamine interactions", TrendsPharm. Sci., 1991, vol. 12, pp. 232-236.*
MeSH (Medical Subject Heading) entry for "Nucleus Accumbens", National Library of Medicine, 2007.*
Verbaan et al. "Cognitive impairment in Parkinson's disease", J.Neurol.Neurosurg.Psychiatry, 2007, vol. 78, pp. 1182-1187, Abstract.*
Margetts et al. "Transdermal drug delivery: principles and opioid therapy", Cont.Ed.Anaes.Crit.CarePain, 2007, vol. 7, No. 5, pp. 171-176.*
Frank Sams-Dodd, A test of the predictive validity of animal models of schizophrenia based on phencyclidine and d-amphetamine, Neuropsychopharmacolog 1998—vol. 18, No. 4:293-304, Published by Elsevier Science Inc. New York, NY, USA.
Eric R. Marcotte, Debra M. Pearson, Lalit K. Srivastava, Animal models of schizophrenia: a critical review, J Psychiatry Neurosci 2001; 26(5):395-410, Published by the Canadian Medical Association, Montreal, CA.
Sarmila Dasgupta, Xi-Ming Li, Andres Jansson, Ulla-Britt Finnman, Toshimitsu Matsui, Ago Rinken, Ernest Arenas, Luigi F. Agnait, Kjell Fuxe, Regulation of dopamine D2 receptor affinity by cholecystokinin octapeptide in fibroblast cells cotransfected with human CCKB and D2 K receptor cDNAs, Molecular Brain Research 36 (1996) 292-299, Published by Elsevier Science B.V.
Hirokazu Tachikawa, Shoji Harada, Yoichi Kawanishi, Takahito Okudo, Hiroyasu Shiraishi, Novel Polymorphism in the promoter and coding regions of the human cholecystokinin B receptor gene: An association analysis with schizophrenia, American Journal of Medical Genetics (Neuropsychiatric Genetics) 88:700-704 (1999), Published by Wiley-Liss, Inc.
Susan E Bachus, Thomas M. Hyde, Mary M. Herman, Michael F. Egan, Joel E. Kleinman, Abnormal Cholecystokinin mRNA levels in entorhinal cortex of schizophrenics, J psychiat Res., vol. 31, No. 2:233-256, 1997, Published by Elsevier Science Ltd 1997 in Great Britain.
Stuart A. Montgomery, Mary C.D. Green, The use of cholecystokinin in schizophrenia: a review, Psychological Medicine, 1988, 18, 593-603, Printed in Great Britain.
David J. Gracey, Robert Bell, David J. King, PD-135,158, a cholecystokinin B antagonist, enhances latent inhibition in the rat, Pharmacology Biochemistry and Behavior, vol. 65, No. 3, pp. 459-463, 2000, Published by Elsevier Science Inc. USA.
M. Bourin, Cholecystokinin as a target for neuropsychiatric drugs, Drug News Perspect. 11(6), Aug. 1998, Published Prous Science.
M. Bourin, G.B. Baker, J. Bradwejn, Neurobiology of panic disorder, J of Psychosomatic Research, vol. 44, No. 1, pp. 163-180, 1998, Published by Elsevier Science Inc.
Reese T. Jones, A Comparative, Randomized, Two-Way Crossover, Food-Effect Bioavailability Study of RPR 1028681 in Healthy Subjects, Protocol No. NIDA-CPU-RPR 102681-01, Jun. 30, 2005, Published by National Institute on Drug Abuse (NIDA).
David Feifel, Tammi Reza, Stephanie Robeck, Antipsychotic potential of CCK-based treatments: an assessment using the prepulse inhibition model of psychosis, Neuropsychopharmacology 1999—Vol. 20, No. 2: 141-149, Published by Elsevier Science Inc., New York, USA.
P. D. Shilling, D. Feifel, SR146131, a cholecystokinin—A receptor agonist, antagonizes prepulse inhibition deficits produced by dizocilpine and DOI, Psychopharmacology (2002) 164:285-293, Published by Springer-Verlag 2002.

(Continued)

Primary Examiner — James D Anderson
Assistant Examiner — Stephanie Springer
(74) Attorney, Agent, or Firm — The Marbury Law Group, PLLC

(57) ABSTRACT

Treatment of schizophrenia or humans suffering from conditions associated with high dopamine levels in ventral striatum or caudate nucleus administers the compound (2S)-2-{3-[3-({[(2R,4R)-4-tert-Butoxycarbonyl-2-(2-fluorophenyl)]-3-thiazolidinyl}carbonylmethyl)ureido]phenyl}propionic acid and its physiological acceptable salts.

25 Claims, 41 Drawing Sheets

OTHER PUBLICATIONS

Robert B. Innis, Benjamin S. Bunney, Dennis Charney, Lawrence H. Price, William M. Glazer, David E. Sternberg, A. Laowrence Rubin, George R. Heninger, Dose the Cholecystokinin antagonists proglumide possess antipsychotic activity?, Psychiatry Research, 18, 1-7, 1986, Published by Elsevier Science Publishers B.V.

Paul B. Hicks, Sophia Vinogradov, Sherry J. Riney, Kevin Su, John G. Csernansky, A preliminary dose-ranging trial of proglumide for the treatment of refractory schizophrenics, J Clin. Psychopharmacol., vol. 9, No. 3, 209-212, 1989.

David J. Gracey, Robert Bell, David J. King, Karen M. Trimble, Barbara J. McDermott, Enhancement of latent inhibition in the rat by the CCK antagonist proglumide, Pharmacology Biochemistry and Behavior, vol. 59, No. 4, pp. 1053-1059, 1998, Published by Elsevier Science Inc. USA.

Kurt Rasmussen, Marsha E. Stockton, Janet F. Czachura, J. Jeffrey Howbert, Cholecystokinin (CCK) and Schizophrenia: the selective CCK B antagonist LY262691 decreases midbrain dopamine unit activity, European Journal of Pharmacology, 209 (1991) 135-138, Published by Elsevier Science Publishers B.V.

Louis Cantilena, Jr., Dean Wong, Roberta Kahn, Ahmed Elkashef, Nora Chiang, Moo Kwang Park, Phase I, double-blind, placebo-controlled dose escalating assessment of potential interaction between intravenous cocaine and RPR 102681, NIDA-CPU-0003 RPR 102681—Cocaine Interaction Study, National Institute of Health, May 22, 2006.

Yun Zhou, Susan M. Resnick, Weiguo Ye, Hong Fan, Daniel P. Holt, William E. Klunk, Chester A. Mathis, Robert Dannals, Dean F. Wong, Using a reference tissue model with spatial constraint to quantify [11C]Pittsburgh compound B PET for early diagnosis of Alzheimer's disease, NeuroImage 36 (2007) 289-312, Published by Elsevier Inc.

Crawley, Schizophrenia an Essay, ESI Special Topics 2001, pp. 1-3, esp. p. 1-2.

Notification of Transmittal of the International Search Report and the Written Opinion of the International Searching Authority, or the Declaration, May 4, 2009. PCT Application No. PCT/US 09/35296.

Martha E. Shenton, Chandlee C. Kickey, Melissa Frumin, Robert W. MCcArley, A Review of MRI Findings in Schizophrenia, Schizophrenia Research 49 (2001) 1-52, Elsevier Science Ltd.

Kurt Tasmussen, CCK, Schizophrenia, And Anxiety—CCK-B Antagonists Inhibit the Activity of Brain Dopamine Neurons, Ann NY Acad Sci. Mar. 23, 1994;713:300-11.

Robert B. Innis, Benjamin S. Bunney, Dennis S. Charney, Lawrence H. Price, William M. Glazer, David E. Sternberg, A. Lawrence Rubin, and George R. Heninger, Does the Cholecystokinin Antagonist Proglumide Possess Antipsychotic Activity?, Psychiatric Research, 18, 1-7, 1986, Elsevier Science Publishers B.V.

M. Bourin, Cholecystokinin as a Target for Neuropsychiatric Drugs, Drug News Perspect 11(6), Aug. 1998.

M. Bourin, M Malinge, E. Vasar, J. Bradwejn, Two faces of cholecystokinin: anxiety and schizophrenia, Fundam. Clin. Pharmacol. 1996;10(2):116-26.

T. Moriji, N. Watanabe, N. Aoki, S. Itoh, Antipsychotic effects of caerulein, a decapeptide chemically related to cholecystokinin octapeptide, on schizophrenia, Int. Pharmacopsychiatry, 1982;17(4): 255-73.

N. P. Nair, D. M. Bloom, G. Debonnel, G. Schwartz, S. Mosticyan, Cholecystokinin-octapeptide in chronic schizophrenia: a double-blind placebo-controlled study, Prog. Neuropsychopharmacol. Biol. Psychiatry, 1984;8 (4-6):711-4.

N. P. Nair, D. M. Bloom, J. N. Nestoros, Cholecystokinin appears to have antipsychotic properties, Prog. Neuropsychopharmacol. Biol. Psychiatry, 1982;6(406):509-12.

M. Albus, Cholecystokinin, Prog. Neuropsychopharmacol. Biol. Psychiatry, 1988;12 Suppl:S5-21.

P. B. Hicks, S. Vinogradov, S. J. Riney, K. Su, J. G. Csernansky, A preliminary dose-ranging trial of proglumide for the treatment of refractory schizophrenics, J. Clin. Psychopharmacol., Jun. 1989;9(3):209-12.

C. A. Tamminga, R. L. Littman, L. D. Alphs, T. N. Chase, G. K. Thaker, A. M. Wagner, Neuronal cholecystokinin and schizophrenia: pathogenic and therapeutic studies, Psychopharmacology, Mar. 1986: vol. 88, No. 3:387-389, Springer Berlin/Heidelberg.

E. Peselow, B. Angrist, A. Sudilovsky, J. Corwin, J. Siekierski, F. Trent, J. Rotrosen, Double blind controlled trials of cholecystokinin octapeptide in neuroleptic-refractory schizophrenia, Psychopharmacology (Berl)., 1987;91(1):80-4.

D. W. Hommer, D. Pickar, J. N. Crawley, H. Weingartner, S. M. Paul, The effects of cholecystokinin-like peptides in schizophrenics and normal human subjects, Ann. N. Y. Acad. Sci., 1985; 448:542-52.

R. A. Boza, D. J. Rotondo, Is cholecystokinin therapeutic in chronic schizophrenia?, J. Clin. Psychiatry, Nov. 1985; 46(11):485-6.

D. L. Garver, M. C. Beinfeld, J. K. Yao, Cholecystokinin, dopamine and schizophrenia, Psychopharmacol. Bull., 1990;26(3):377-80.

T. Nishikawa, M. Tanaka, A. Tsuda, I. Koga, Y. Uchida, Treatment of tardive dyskinesia with ceruletide, Prog. Neuropsychopharmacol. Biol. Psychiatry, 1988;12(5):803-12.

S. A. Montomery, M. C. Green, The use of cholecystokinin in schizophrenia: a review, Psycho!. Med., Aug. 1988;18(3):593-603.

N. P. Nair, S. Lal, D. M. Bloom, Cholecystokinin peptides, dopamine and schizophrenia—a review, Prog. Neuropsychopharmacol. Biol. Psychiatry, 1985;9(5-6):515-24.

International Preliminary Report on Patentability, WIPO, Sep. 10, 2010, 6pgs.

* cited by examiner

FIG. 1

| Study Phase | Session Number | Study Day | Infusion |
|---|---|---|---|
| Screening | Session 1 | 2 | Saline/20 mg cocaine followed by 20 mg cocaine/saline 1 hr later |
| Screening | Session 2 | 3 | Saline/40 mg cocaine followed by 40 mg cocaine/saline 1 hr later |
| Baseline | Session 3 | 7 | Saline/20 mg cocaine followed by 20 mg cocaine/saline 1 hr later |
| Baseline | Session 4 | 8 | Saline/40 mg cocaine followed by 40 mg cocaine/saline 1 hr later |
| Treatment | Session 5 | 14 | RPR 102681 200 mg b.i.d./placebo followed by saline/20 mg cocaine 1 hr later and then followed by 20 mg cocaine/saline 1 hr later |
| Treatment | Session 6 | 15 | RPR 102681 200 mg b.i.d./placebo followed by saline/40 mg cocaine 1 hr later and then followed by 40 mg cocaine/saline 1 hr later |
| Treatment | Session 7 | 21 | RPR 102681 400 mg b.i.d./placebo followed by saline/20 mg cocaine 1 hr later and then followed by 20 mg cocaine/saline 1 hr later |
| Treatment | Session 8 | 22 | RPR 102681 400 mg b.i.d./placebo followed by saline/40 mg cocaine 1 hr later and then followed by 40 mg cocaine/saline 1 hr later |
| Treatment | Session 9 | 28 | RPR 102681 800 mg b.i.d./placebo followed by saline/20 mg cocaine 1 hr later and then followed by 20 mg cocaine/saline 1 hr later |
| Treatment | Session 10 | 29 | RPR 102681 800 mg b.i.d./placebo followed by saline/40 mg cocaine 1 hr later and then followed by 40 mg cocaine/saline 1 hr later |

FIG. 2

| Cocaine | Day | Group | Time | HR | | | SBP | | | DBP | | |
|---|---|---|---|---|---|---|---|---|---|---|---|---|
| | | | | N | Mean | SD | N | Mean | SD | N | Mean | SD |
| 20 mg | 7 | RPR | Pre-inf | 12 | 73.9 | 10.0 | 12 | 119.7 | 11.2 | 12 | 71.7 | 7.6 |
| | | | Saline | 12 | 86.7 | 11.8 | 12 | 130.7 | 12.2 | 12 | 80.1 | 6.1 |
| | | | Cocaine | 12 | 100.1 | 12.8 | 12 | 139.2 | 9.5 | 12 | 89.6 | 9.6 |
| | | Placebo | Pre-inf | 7 | 76.9 | 7.0 | 7 | 117.9 | 9.0 | 7 | 69.3 | 4.5 |
| | | | Saline | 7 | 88.6 | 6.9 | 7 | 127.9 | 11.0 | 7 | 78.7 | 5.5 |
| | | | Cocaine | 7 | 98.9 | 9.3 | 7 | 135.4 | 11.1 | 7 | 84.3 | 4.9 |
| | 14 | RPR | Pre-inf | 12 | 73.3 | 7.4 | 12 | 122.3 | 10.6 | 12 | 71.7 | 8.6 |
| | | | Saline | 12 | 84.8 | 14.5 | 12 | 129.3 | 11.0 | 12 | 77.3 | 8.6 |
| | | | Cocaine | 12 | 98.9 | 13.4 | 12 | 143.0 | 12.4 | 12 | 86.9 | 9.4 |
| | | Placebo | Pre-inf | 6 | 77.7 | 3.8 | 6 | 124.9 | 9.9 | 6 | 70.1 | 5.4 |
| | | | Saline | 6 | 91.5 | 6.3 | 6 | 136.0 | 10.3 | 6 | 80.3 | 7.8 |
| | | | Cocaine | 6 | 98.2 | 12.5 | 6 | 143.2 | 16.1 | 6 | 85.3 | 10.4 |
| | 21 | RPR | Pre-inf | 12 | 75.6 | 10.4 | 12 | 122.0 | 12.2 | 12 | 73.1 | 10.1 |
| | | | Saline | 12 | 89.0 | 12.2 | 12 | 133.7 | 12.6 | 12 | 82.3 | 10.3 |
| | | | Cocaine | 12 | 102.9 | 16.5 | 12 | 142.8 | 11.7 | 12 | 88.5 | 9.8 |
| | | Placebo | Pre-inf | 5 | 78.5 | 3.5 | 5 | 126.1 | 10.5 | 5 | 72.5 | 8.8 |
| | | | Saline | 5 | 90.6 | 8.8 | 5 | 140.0 | 8.7 | 5 | 84.4 | 7.6 |
| | | | Cocaine | 5 | 101.8 | 10.9 | 5 | 146.0 | 5.4 | 5 | 88.0 | 10.6 |
| | 28 | RPR | Pre-inf | 12 | 76.9 | 10.3 | 12 | 122.4 | 10.4 | 12 | 73.9 | 8.3 |
| | | | Saline | 12 | 90.5 | 17.9 | 12 | 134.0 | 11.1 | 12 | 82.2 | 8.3 |
| | | | Cocaine | 12 | 107.2 | 18.5 | 12 | 145.6 | 11.0 | 12 | 87.3 | 9.8 |
| | | Placebo | Pre-inf | 5 | 78.8 | 8.9 | 5 | 129.0 | 8.2 | 5 | 75.0 | 10.6 |
| | | | Saline | 5 | 92.6 | 12.5 | 5 | 141.4 | 7.2 | 5 | 86.2 | 8.3 |
| | | | Cocaine | 5 | 98.8 | 8.3 | 5 | 151.4 | 13.7 | 5 | 87.0 | 10.0 |
| 40 mg | 8 | RPR | Pre-inf | 12 | 73.1 | 9.8 | 12 | 122.3 | 9.6 | 12 | 73.3 | 8.6 |
| | | | Saline | 12 | 86.6 | 14.0 | 12 | 131.4 | 11.6 | 12 | 81.3 | 9.9 |
| | | | Cocaine | 12 | 108.8 | 17.5 | 12 | 147.5 | 11.4 | 12 | 89.8 | 8.3 |
| | | Placebo | Pre-inf | 7 | 80.4 | 11.0 | 7 | 126.5 | 10.3 | 7 | 76.0 | 7.2 |
| | | | Saline | 7 | 92.9 | 17.4 | 7 | 138.3 | 10.7 | 7 | 83.1 | 5.1 |
| | | | Cocaine | 7 | 109.0 | 15.9 | 7 | 155.1 | 24.1 | 7 | 90.4 | 8.0 |
| | 15 | RPR | Pre-inf | 12 | 73.9 | 9.0 | 12 | 123.3 | 10.0 | 12 | 73.4 | 7.1 |
| | | | Saline | 12 | 87.5 | 14.4 | 12 | 131.6 | 10.9 | 12 | 82.7 | 7.7 |
| | | | Cocaine | 12 | 106.0 | 18.7 | 12 | 146.4 | 13.3 | 12 | 89.6 | 9.8 |
| | | Placebo | Pre-inf | 6 | 79.3 | 4.3 | 6 | 129.6 | 13.9 | 6 | 73.4 | 9.4 |
| | | | Saline | 6 | 91.7 | 9.5 | 6 | 140.2 | 9.8 | 6 | 87.0 | 11.0 |
| | | | Cocaine | 6 | 109.7 | 12.2 | 6 | 157.3 | 24.7 | 6 | 90.7 | 12.3 |
| | 22 | RPR | Pre-inf | 12 | 75.8 | 9.5 | 12 | 123.1 | 12.4 | 12 | 72.9 | 10.9 |
| | | | Saline | 12 | 92.6 | 14.5 | 12 | 134.8 | 14.0 | 12 | 80.7 | 10.8 |
| | | | Cocaine | 12 | 109.3 | 15.6 | 12 | 148.3 | 15.0 | 12 | 89.0 | 10.9 |
| | | Placebo | Pre-inf | 5 | 80.0 | 4.1 | 5 | 131.3 | 8.2 | 5 | 78.0 | 8.2 |
| | | | Saline | 5 | 89.8 | 7.7 | 5 | 138.4 | 11.1 | 5 | 77.4 | 7.8 |
| | | | Cocaine | 5 | 111.2 | 11.8 | 5 | 156.2 | 3.8 | 5 | 89.2 | 5.4 |
| | 29 | RPR | Pre-inf | 11 | 76.8 | 8.2 | 11 | 126.2 | 11.0 | 11 | 75.1 | 9.2 |
| | | | Saline | 11 | 97.7 | 13.3 | 11 | 141.1 | 10.4 | 11 | 84.0 | 10.6 |
| | | | Cocaine | 11 | 107.8 | 17.6 | 11 | 151.3 | 14.8 | 11 | 92.5 | 11.5 |
| | | Placebo | Pre-inf | 5 | 79.6 | 8.2 | 5 | 133.4 | 10.2 | 5 | 79.5 | 9.8 |
| | | | Saline | 5 | 97.4 | 10.7 | 5 | 145.6 | 12.8 | 5 | 81.8 | 9.0 |
| | | | Cocaine | 5 | 108.6 | 13.9 | 5 | 159.0 | 15.6 | 5 | 95.2 | 5.5 |

FIG. 3

| Cocaine | RPR Dose Comparison | HR N | HR Mean+/-SD | HR P-Value | SBP N | SBP Mean+/-SD | SBP P-Value | DBP N | DBP Mean+/-SD | DBP P-Value |
|---|---|---|---|---|---|---|---|---|---|---|
| 20mg | 0mg vs. 200mg | | | | 12 | -5.167+/-7.25 | 00.31 | | | |
| | 0mg vs. 400mg | | | | | | | | | |
| | 0mg vs. 800mg | | | | | | | 12 | 4.33+/-8.17 | 0.093 |
| | 200mg vs. 400mg | | | | 12 | 4.58+/-7.24 | 0.051 | 12 | 3.5+/-5.3 | 0.044 |
| | 200mg vs. 800mg | | | | | | | 12 | 4.5+/-5.0 | 0.009 |
| | 400mg vs. 800mg | | | | | | | | | |
| 40mg | 0mg vs. 200mg | | | | | | | | | |
| | 0mg vs. 400mg | | | | | | | | | |
| | 0mg vs. 800mg | 11 | 13.1+/-13.6 | 0.009 | | | | | | |
| | 200mg vs. 400mg | | | | | | | | | |
| | 200mg vs. 800mg | 11 | 9.09+/-13.0 | 0.043 | | | | | | |
| | 400mg vs. 800mg | | | | | | | | | |

*Only P-values <0.1 are reported*

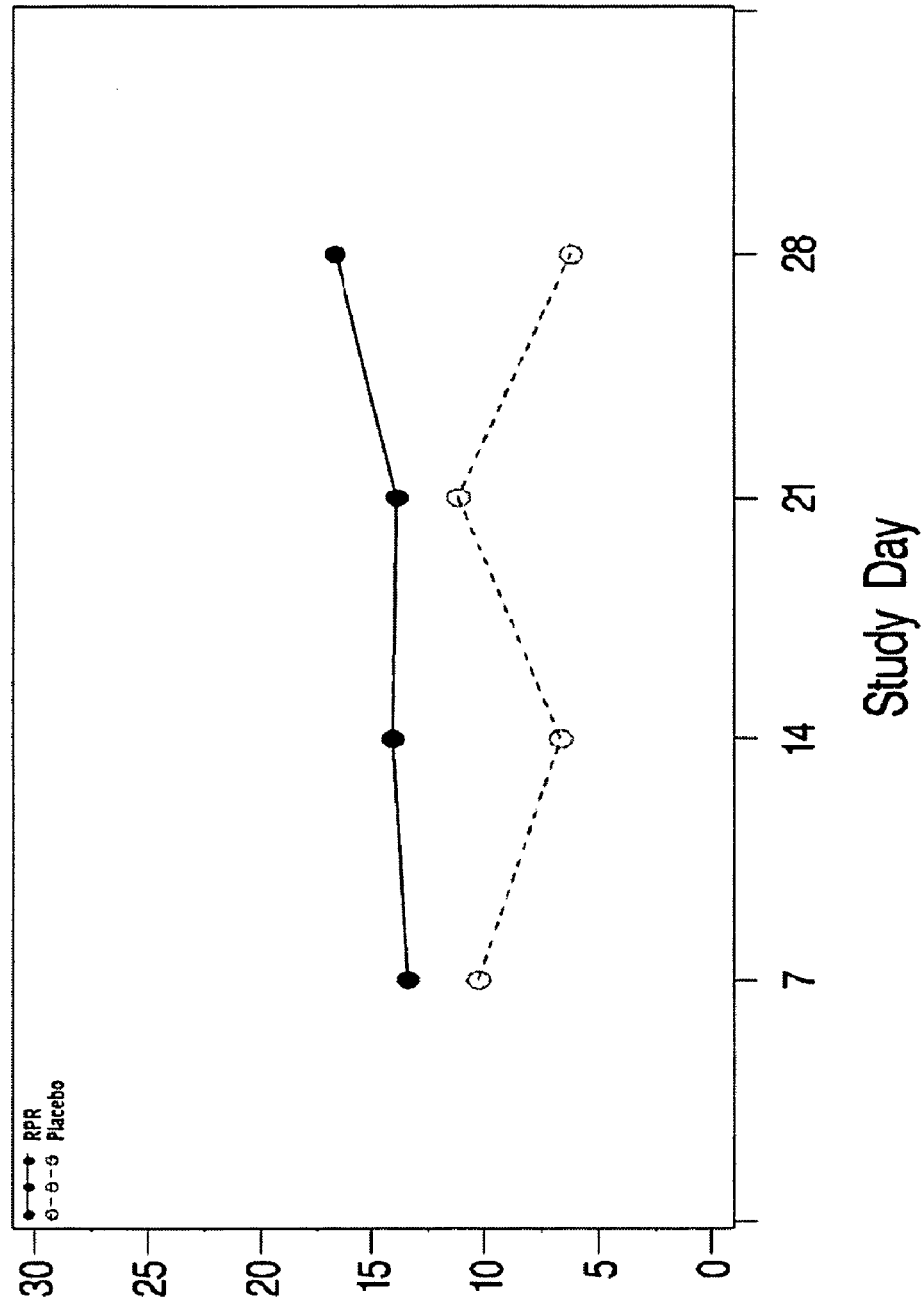

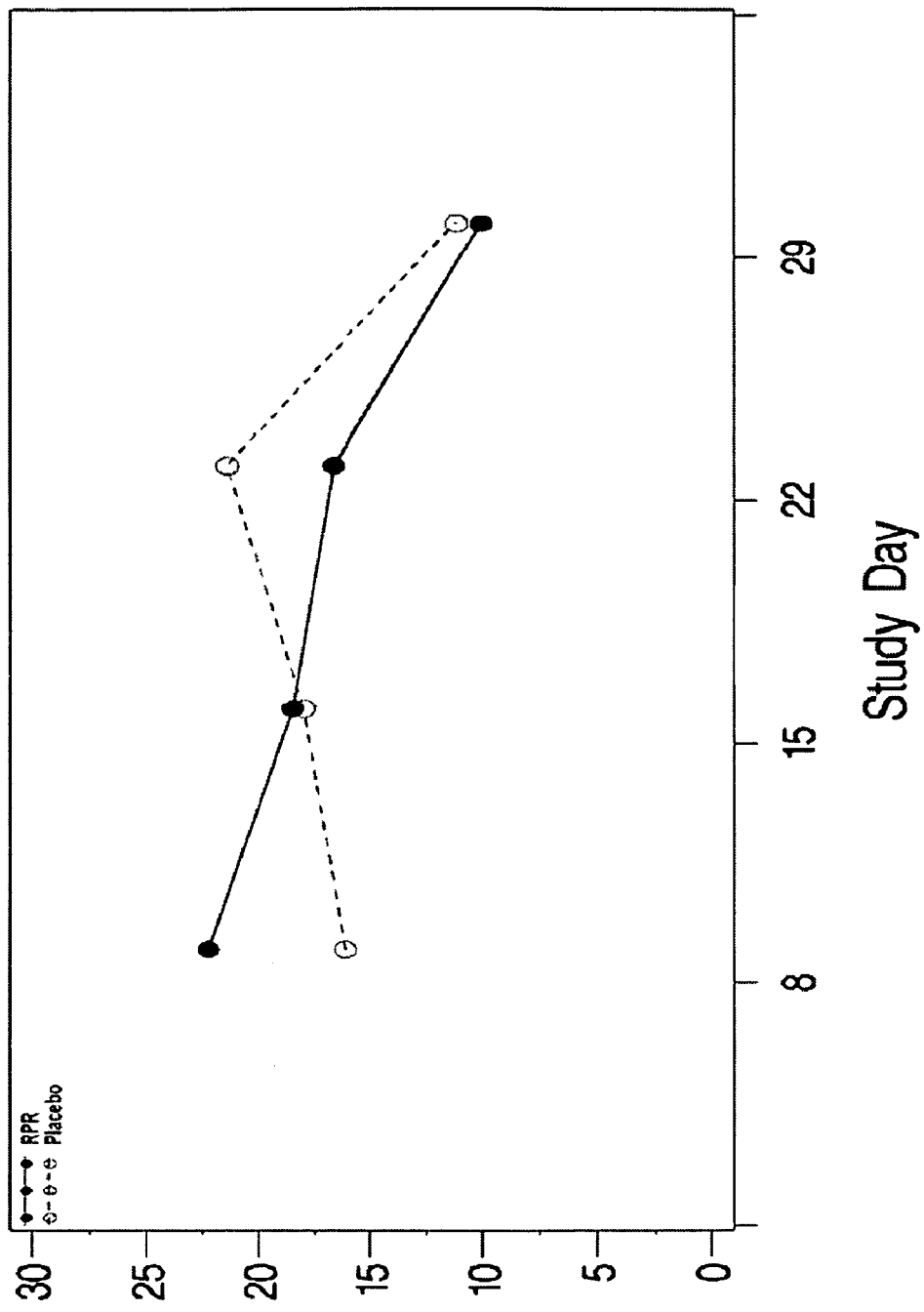

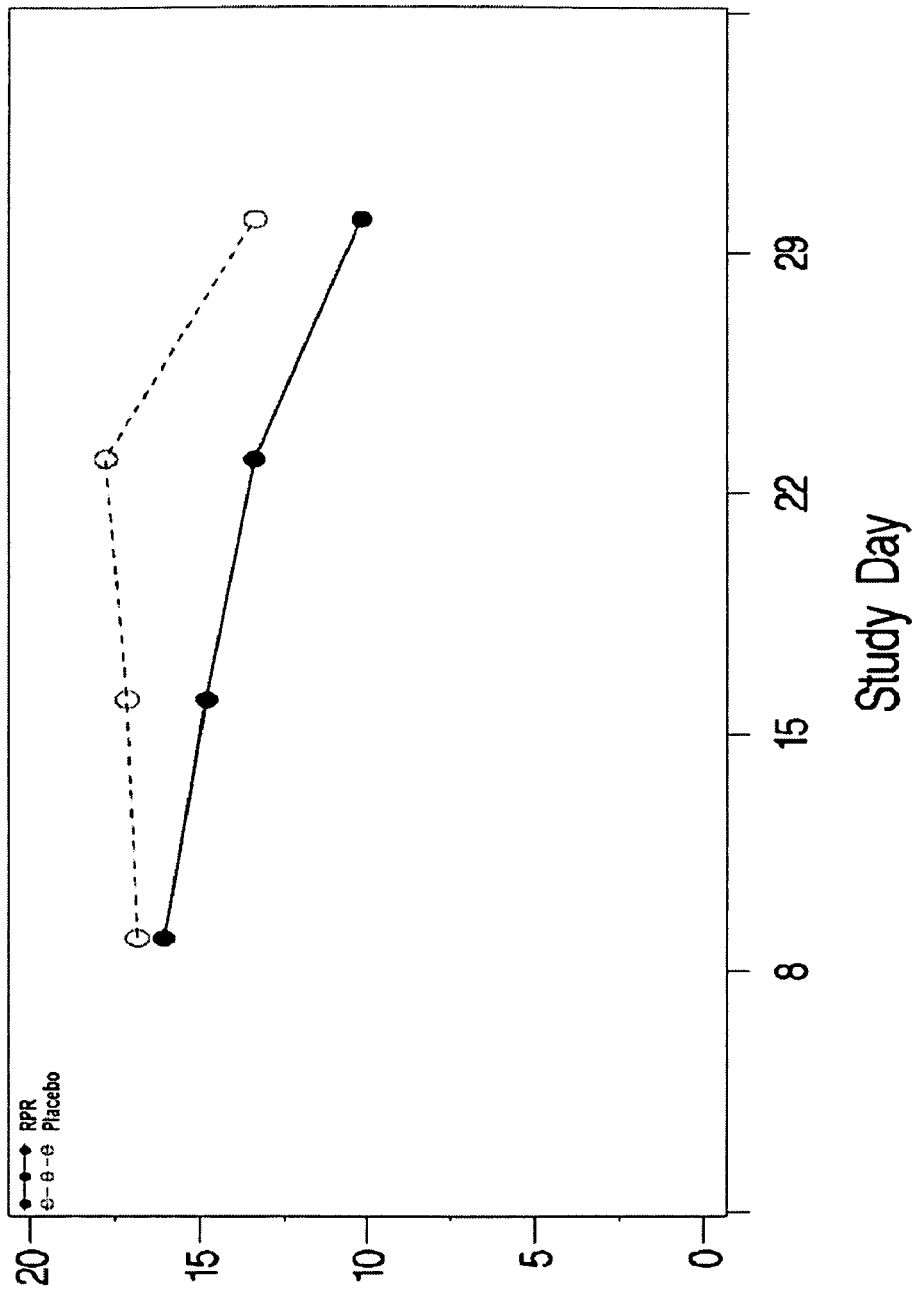

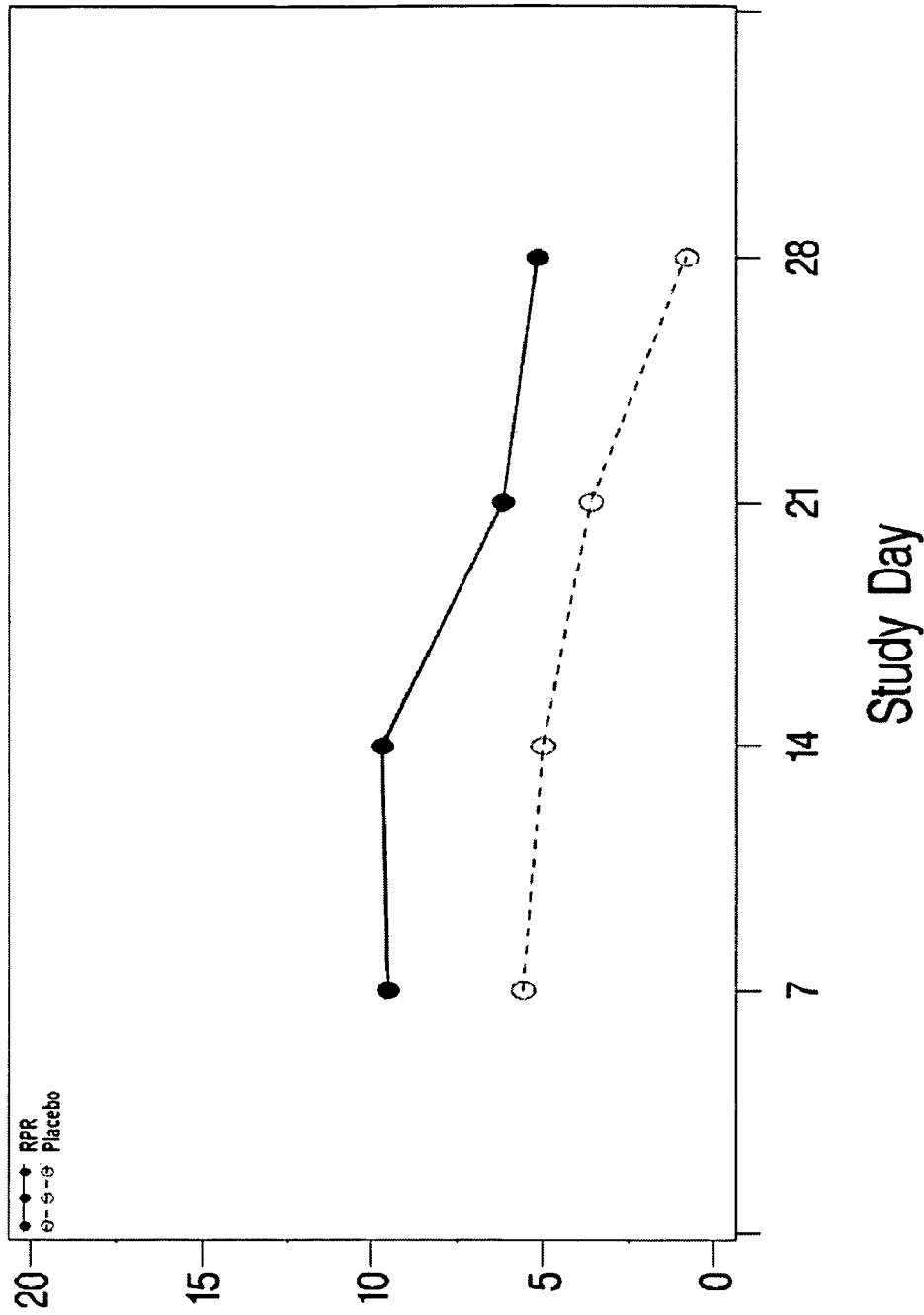

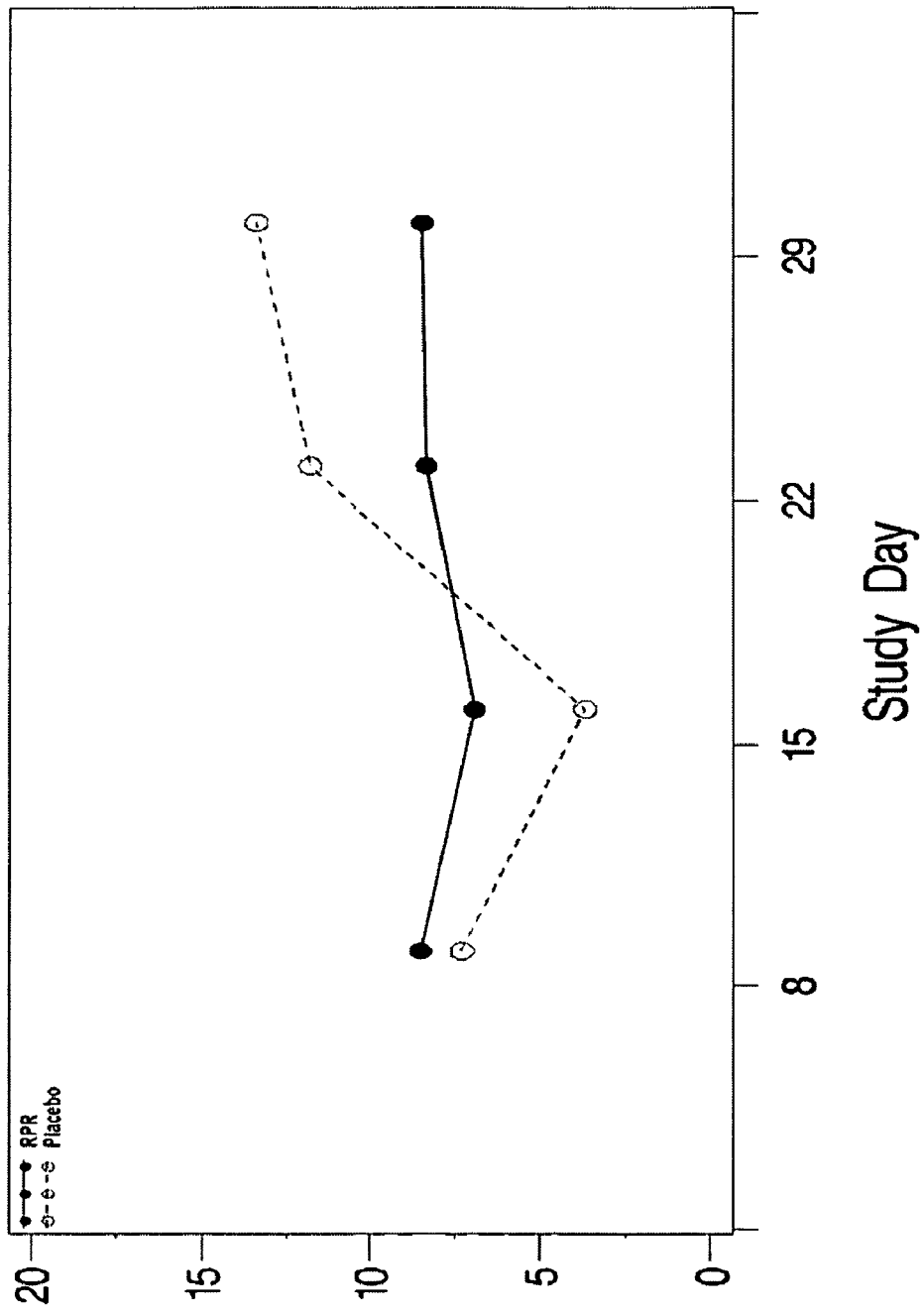

FIG. 5

| Value | Groups | N | Visit | Mean | Range | |
|---|---|---|---|---|---|---|
| | | | | | Min | Max |
| VR (bpm) | RPR 102681 | 12 | Pre-intake Screening | 59.3 | 48.0 | 68.0 |
| | | 12 | Intake Screening | 66.5 | 56.0 | 77.0 |
| | | 12 | Discharge | 76.8 | 61.0 | 96.0 |
| | | 11 | Follow-up | 73.5 | 45.0 | 99.0 |
| | Placebo | 7 | Pre-intake Screening | 64.1 | 47.0 | 79.0 |
| | | 7 | Intake Screening | 79.1 | 64.0 | 82.0 |
| | | 7 | Discharge | 82.1 | 63.0 | 97.0 |
| | | 6 | Follow-up | 72.3 | 66.0 | 86.0 |
| PR (ms) | RPR 102681 | 12 | Pre-intake Screening | 153.8 | 128.0 | 178.0 |
| | | 12 | Intake Screening | 153.3 | 124.0 | 170.0 |
| | | 12 | Discharge | 159.0 | 132.0 | 178.0 |
| | | 11 | Follow-up | 152.5 | 128.0 | 174.0 |
| | Placebo | 7 | Pre-intake Screening | 158.0 | 112.0 | 210.0 |
| | | 7 | Intake Screening | 158.0 | 116.0 | 212.0 |
| | | 7 | Discharge | 159.7 | 118.0 | 212.0 |
| | | 6 | Follow-up | 144.3 | 118.0 | 164.0 |
| QT (ms) | RPR 102681 | 12 | Pre-intake Screening | 386.9 | 352.0 | 431.0 |
| | | 12 | Intake Screening | 369.4 | 334.0 | 390.0 |
| | | 12 | Discharge | 353.2 | 307.0 | 385.0 |
| | | 11 | Follow-up | 364.6 | 324.0 | 434.0 |
| | Placebo | 7 | Pre-intake Screening | 366.1 | 317.0 | 416.0 |
| | | 7 | Intake Screening | 362.6 | 342.0 | 394.0 |
| | | 7 | Discharge | 336.4 | 314.0 | 349.0 |
| | | 6 | Follow-up | 359.2 | 351.0 | 376.0 |
| QRS (ms) | RPR 102681 | 12 | Pre-intake Screening | 86.7 | 74.0 | 104.0 |
| | | 12 | Intake Screening | 88.5 | 80.0 | 104.0 |
| | | 12 | Discharge | 86.8 | 74.0 | 106.0 |
| | | 11 | Follow-up | 87.1 | 76.0 | 106.0 |
| | Placebo | 7 | Pre-intake Screening | 88.6 | 80.0 | 94.0 |
| | | 7 | Intake Screening | 87.7 | 92.0 | 96.0 |
| | | 7 | Discharge | 88.6 | 80.0 | 98.0 |
| | | 6 | Follow-up | 87.7 | 78.0 | 96.0 |
| RR (ms) | RPR 102681 | 12 | Pre-intake Screening | 977.3 | 819.0 | 1244.0 |
| | | 12 | Intake Screening | 860.3 | 718.0 | 1006.0 |
| | | 12 | Discharge | 772.0 | 606.0 | 906.0 |
| | | 11 | Follow-up | 806.1 | 610.0 | 1123.0 |
| | Placebo | 7 | Pre-intake Screening | 947.1 | 769.0 | 1265.0 |
| | | 7 | Intake Screening | 813.0 | 731.0 | 920.0 |
| | | 7 | Discharge | 723.3 | 635.0 | 905.0 |
| | | 6 | Follow-up | 838.7 | 688.0 | 897.0 |

FIG. 6A

|  | Day | Group | N | Mean | S.D. | Min | Max | P-Value* |
|---|---|---|---|---|---|---|---|---|
| PR | -7 to 1 | RPR | 12 | 153.3 | 14.9 | 124.0 | 170.0 | |
|  |  | Placebo | 7 | 158.0 | 29.6 | 116.0 | 212.0 | |
|  | 8 | RPR | 12 | 163.8 | 18.7 | 134.0 | 200.0 | 0.012 |
|  |  | Placebo | 7 | 158.3 | 27.7 | 118.0 | 200.0 | n.s. |
|  | 15 | RPR | 12 | 163.2 | 16.8 | 134.0 | 186.0 | 0.003 |
|  |  | Placebo | 6 | 151.7 | 22.3 | 122.0 | 178.0 | n.s. |
|  | 22 | RPR | 12 | 165.8 | 18.2 | 138.0 | 202.0 | <0.001 |
|  |  | Placebo | 5 | 162.8 | 18.4 | 142.0 | 186.0 | n.s. |
|  | 29 | RPR | 11 | 165.6 | 14.7 | 136.0 | 184.0 | <0.001 |
|  |  | Placebo | 5 | 162.0 | 15.4 | 144.0 | 184.0 | n.s. |
| RR | -7 to 1 | RPR | 12 | 860.3 | 115.3 | 718.0 | 1006 | |
|  |  | Placebo | 7 | 813.0 | 72.7 | 731.0 | 920.0 | |
|  | 8 | RPR | 12 | 828.3 | 124.3 | 662.0 | 1078 | n.s. |
|  |  | Placebo | 7 | 779.7 | 148.2 | 618.0 | 1078 | n.s. |
|  | 15 | RPR | 12 | 843.4 | 137.6 | 657.0 | 1079 | n.s. |
|  |  | Placebo | 6 | 762.0 | 34.5 | 728.0 | 829.0 | n.s. |
|  | 22 | RPR | 12 | 784.2 | 120.3 | 623.0 | 1001 | n.s. |
|  |  | Placebo | 5 | 797.2 | 47.9 | 731.0 | 840.0 | n.s. |
|  | 29 | RPR | 11 | 823.6 | 108.3 | 669.0 | 1014 | n.s. |
|  |  | Placebo | 5 | 748.8 | 51.0 | 670.0 | 792.0 | n.s. |
| QT | -7 to 1 | RPR | 12 | 369.4 | 19.4 | 334.0 | 390.0 | |
|  |  | Placebo | 7 | 362.6 | 21.1 | 342.0 | 394.0 | |
|  | 8 | RPR | 12 | 356.3 | 25.5 | 308.0 | 391.0 | n.s. |
|  |  | Placebo | 7 | 348.1 | 21.7 | 326.0 | 388.0 | n.s. |
|  | 15 | RPR | 12 | 362.4 | 24.4 | 324.0 | 415.0 | n.s. |
|  |  | Placebo | 6 | 336.8 | 24.1 | 296.0 | 370.0 | n.s. |
|  | 22 | RPR | 12 | 355.8 | 23.4 | 322.0 | 390.0 | n.s. |
|  |  | Placebo | 5 | 348.4 | 10.2 | 335.0 | 363.0 | n.s. |
|  | 29 | RPR | 11 | 359.0 | 21.1 | 333.0 | 391.0 | n.s. |
|  |  | Placebo | 5 | 353.2 | 16.7 | 333.0 | 375.0 | n.s. |

*The nonparametric Signed Rank Test was used to compare reading at intake screening (days -7 to 1) and pre infusion value for each group and day. Only P-values <0.05 are reported here. (n.s.) means not significant at α=0.05 level.

FIG. 6B

| | | | PR | | | | Change from Pre Infusion Baseline | | | | | |
|---|---|---|---|---|---|---|---|---|---|---|---|---|
| | | | N | Mean | SD | Min | Max | N | Mean | SD | Min | Max | P-value |
| Day | Time | Group | | | | | | | | | | | |
| 8 | Baseline (-10 Min) | RPR | 12 | 163.8 | 18.7 | 134.0 | 200.0 | 0 | | | | | |
| | | Placebo | 7 | 158.3 | 27.7 | 118.0 | 200.0 | 0 | | | | | |
| | Post IV (4 Min) | RPR | 12 | 153.2 | 15.7 | 120.0 | 174.0 | 12 | -10.7 | 18.3 | -42.0 | 28.0 | n.s. |
| | | Placebo | 7 | 146.0 | 19.2 | 120.0 | 172.0 | 7 | -12.3 | 10.1 | -28.0 | 2.0 | 0.031 |
| | Post IV (40 Min) | RPR | 12 | 157.8 | 15.5 | 134.0 | 184.0 | 12 | -6.0 | 7.6 | -16.0 | 4.0 | 0.019 |
| | | Placebo | 7 | 154.3 | 27.6 | 118.0 | 202.0 | 7 | -4.0 | 6.5 | -16.0 | 2.0 | n.s. |
| 15 | Baseline (-10 Min) | RPR | 12 | 163.2 | 16.8 | 134.0 | 186.0 | 0 | | | | | |
| | | Placebo | 6 | 151.7 | 22.3 | 122.0 | 178.0 | 0 | | | | | |
| | Post IV (4 Min) | RPR | 12 | 147.0 | 20.1 | 114.0 | 172.0 | 12 | -16.2 | 16.5 | -56.0 | 8.0 | 0.003 |
| | | Placebo | 6 | 144.7 | 17.1 | 122.0 | 164.0 | 6 | -7.0 | 8.9 | -18.0 | 6.0 | n.s. |
| | Post IV (40 Min) | RPR | 12 | 155.0 | 13.7 | 134.0 | 174.0 | 12 | -8.2 | 8.1 | -24.0 | 2.0 | 0.003 |
| | | Placebo | 6 | 146.0 | 20.1 | 118.0 | 166.0 | 6 | -5.7 | 6.1 | -14.0 | 2.0 | n.s. |
| 22 | Baseline (-10 Min) | RPR | 12 | 165.8 | 18.2 | 138.0 | 202.0 | 0 | | | | | |
| | | Placebo | 5 | 162.8 | 18.4 | 142.0 | 186.0 | 0 | | | | | |
| | Post IV (4 Min) | RPR | 12 | 150.8 | 16.9 | 124.0 | 174.0 | 12 | -15.0 | 12.7 | -36.0 | 12.0 | 0.003 |
| | | Placebo | 5 | 156.8 | 17.6 | 128.0 | 174.0 | 5 | -6.0 | 19.8 | -22.0 | 28.0 | n.s. |
| | Post IV (40 Min) | RPR | 12 | 159.3 | 14.5 | 138.0 | 182.0 | 12 | -6.5 | 9.7 | -32.0 | 4.0 | 0.015 |
| | | Placebo | 5 | 154.4 | 13.4 | 138.0 | 170.0 | 5 | -8.4 | 7.1 | -16.0 | 2.0 | n.s. |
| 29 | Baseline (-10 Min) | RPR | 11 | 165.6 | 14.7 | 136.0 | 184.0 | 0 | | | | | |
| | | Placebo | 5 | 162.0 | 15.4 | 144.0 | 184.0 | 0 | | | | | |
| | Post IV (4 Min) | RPR | 11 | 154.0 | 17.5 | 122.0 | 182.0 | 11 | -11.6 | 13.5 | -32.0 | 8.0 | 0.027 |
| | | Placebo | 5 | 152.0 | 20.8 | 116.0 | 168.0 | 5 | -10.0 | 18.7 | -28.0 | 12.0 | n.s. |
| | Post IV (40 Min) | RPR | 11 | 157.1 | 15.2 | 134.0 | 176.0 | 11 | -8.5 | 8.6 | -18.0 | 8.0 | 0.012 |
| | | Placebo | 5 | 154.0 | 19.1 | 134.0 | 172.0 | 5 | -8.0 | 10.6 | -18.0 | 10.0 | n.s. |

FIG. 6C

| | | | RR | | | | Change from Pre Infusion Baseline | | | | | |
|---|---|---|---|---|---|---|---|---|---|---|---|---|
| | | | N | Mean | SD | Min | Max | N | Mean | SD | Min | Max | P-value |
| Day | Time | Group | | | | | | | | | | | |
| 8 | Baseline (-10 Min) | RPR | 12 | 828.3 | 124.3 | 662.0 | 1078 | 0 | | | | | |
| | | Placebo | 7 | 779.7 | 148.2 | 618.0 | 1078 | 0 | | | | | |
| | Post IV (4 Min) | RPR | 12 | 617.5 | 82.1 | 488.0 | 749.0 | 12 | -211 | 122.5 | -388 | 18.0 | <0.001 |
| | | Placebo | 7 | 591.6 | 100.5 | 451.0 | 747.0 | 7 | -188 | 181.3 | -491 | 129.0 | 0.031 |
| | Post IV (40 Min) | RPR | 12 | 740.8 | 117.3 | 551.0 | 926.0 | 12 | -87.5 | 125.1 | -264 | 70.0 | n.s. |
| | | Placebo | 7 | 725.6 | 91.8 | 591.0 | 841.0 | 7 | -54.1 | 130.0 | -237 | 162.0 | n.s. |
| 15 | Baseline (-10 Min) | RPR | 12 | 843.4 | 137.6 | 657.0 | 1079 | 0 | | | | | |
| | | Placebo | 6 | 762.0 | 34.5 | 728.0 | 829.0 | 0 | | | | | |
| | Post IV (4 Min) | RPR | 12 | 627.5 | 105.9 | 481.0 | 820.0 | 12 | -216 | 105.2 | -396 | -41.0 | <0.001 |
| | | Placebo | 6 | 585.3 | 86.3 | 477.0 | 689.0 | 6 | -177 | 67.8 | -251 | -66.0 | 0.031 |
| | Post IV (40 Min) | RPR | 12 | 749.8 | 135.5 | 518.0 | 984.0 | 12 | -93.7 | 120.7 | -280 | 53.0 | 0.022 |
| | | Placebo | 6 | 725.0 | 71.9 | 601.0 | 796.0 | 6 | -37.0 | 54.7 | -127 | 41.0 | n.s. |
| 22 | Baseline (-10 Min) | RPR | 12 | 784.2 | 120.3 | 623.0 | 1001 | 0 | | | | | |
| | | Placebo | 5 | 797.2 | 47.9 | 731.0 | 840.0 | 0 | | | | | |
| | Post IV (4 Min) | RPR | 12 | 583.1 | 93.8 | 448.0 | 762.0 | 12 | -201 | 107.8 | -391 | -6.0 | <0.001 |
| | | Placebo | 5 | 619.2 | 105.1 | 454.0 | 744.0 | 5 | -178 | 96.4 | -277 | -19.0 | n.s. |
| | Post IV (40 Min) | RPR | 12 | 759.8 | 138.3 | 574.0 | 987.0 | 12 | -24.3 | 112.9 | -262 | 130.0 | n.s. |
| | | Placebo | 5 | 735.0 | 39.6 | 701.0 | 800.0 | 5 | -62.2 | 66.4 | -129 | 37.0 | n.s. |
| 29 | Baseline (-10 Min) | RPR | 11 | 823.6 | 108.3 | 669.0 | 1014 | 0 | | | | | |
| | | Placebo | 5 | 748.8 | 51.0 | 670.0 | 792.0 | 0 | | | | | |
| | Post IV (4 Min) | RPR | 11 | 600.6 | 104.8 | 450.0 | 763.0 | 11 | -223 | 105.4 | -398 | -79.0 | <0.001 |
| | | Placebo | 5 | 596.2 | 84.5 | 463.0 | 673.0 | 5 | -153 | 79.2 | -264 | -57.0 | n.s. |
| | Post IV (40 Min) | RPR | 11 | 750.1 | 140.0 | 539.0 | 947.0 | 11 | -73.5 | 100.1 | -230 | 111.0 | n.s. |
| | | Placebo | 5 | 722.2 | 92.5 | 642.0 | 855.0 | 5 | -26.6 | 75.2 | -125 | 67.0 | n.s. |

FIG. 6D

| | | | QT | | | | Change from Pre Infusion Baseline | | | | | |
|---|---|---|---|---|---|---|---|---|---|---|---|---|
| | | | N | Mean | S.D. | Min | Max | N | Mean | S.D. | Min | Max | P-value |
| Day | Time | Group | | | | | | | | | | | |
| 8 | Baseline (-10 Min) | RPR | 12 | 356.3 | 25.5 | 308.0 | 391.0 | 0 | | | | | |
| | | Placebo | 7 | 348.1 | 21.7 | 326.0 | 388.0 | 0 | | | | | |
| | Post IV (4 Min) | RPR | 12 | 338.3 | 24.4 | 304.0 | 377.0 | 12 | -18.0 | 13.5 | -48.0 | 3.0 | 0.001 |
| | | Placebo | 7 | 331.4 | 24.6 | 302.0 | 365.0 | 7 | -16.7 | 17.2 | -32.0 | 21.0 | n.s. |
| | Post IV (40 Min) | RPR | 12 | 348.8 | 28.1 | 301.0 | 391.0 | 12 | -7.5 | 17.8 | -44.0 | 13.0 | n.s. |
| | | Placebo | 7 | 337.4 | 19.7 | 317.0 | 371.0 | 7 | -10.7 | 13.4 | -32.0 | 9.0 | n.s. |
| 15 | Baseline (-10 Min) | RPR | 12 | 362.4 | 24.4 | 324.0 | 415.0 | 0 | | | | | |
| | | Placebo | 6 | 336.8 | 24.1 | 296.0 | 370.0 | 0 | | | | | |
| | Post IV (4 Min) | RPR | 12 | 348.0 | 25.4 | 316.0 | 399.0 | 12 | -14.4 | 16.9 | -37.0 | 20.0 | 0.025 |
| | | Placebo | 6 | 319.0 | 29.5 | 271.0 | 359.0 | 6 | -17.8 | 17.6 | -32.0 | 17.0 | n.s. |
| | Post IV (40 Min) | RPR | 12 | 351.3 | 27.9 | 291.0 | 392.0 | 12 | -11.2 | 17.2 | -40.0 | 21.0 | 0.036 |
| | | Placebo | 6 | 333.0 | 9.9 | 325.0 | 348.0 | 6 | -3.8 | 19.0 | -22.0 | 30.0 | n.s. |
| 22 | Baseline (-10 Min) | RPR | 12 | 355.8 | 23.4 | 322.0 | 390.0 | 0 | | | | | |
| | | Placebo | 5 | 348.4 | 10.2 | 335.0 | 363.0 | 0 | | | | | |
| | Post IV (4 Min) | RPR | 12 | 342.8 | 31.1 | 300.0 | 392.0 | 12 | -13.1 | 18.5 | -35.0 | 27.0 | 0.041 |
| | | Placebo | 5 | 338.8 | 33.6 | 297.0 | 389.0 | 5 | -9.6 | 31.0 | -47.0 | 38.0 | n.s. |
| | Post IV (40 Min) | RPR | 12 | 354.6 | 31.5 | 310.0 | 398.0 | 12 | -1.3 | 13.0 | -17.0 | 27.0 | n.s. |
| | | Placebo | 5 | 338.2 | 12.5 | 324.0 | 352.0 | 5 | -10.2 | 6.4 | -15.0 | 1.0 | n.s. |
| 29 | Baseline (-10 Min) | RPR | 11 | 359.0 | 21.1 | 333.0 | 391.0 | 0 | | | | | |
| | | Placebo | 5 | 353.2 | 16.7 | 333.0 | 375.0 | 0 | | | | | |
| | Post IV (4 Min) | RPR | 11 | 341.5 | 27.2 | 293.0 | 382.0 | 11 | -17.5 | 19.3 | -43.0 | 22.0 | 0.015 |
| | | Placebo | 5 | 329.4 | 28.7 | 291.0 | 365.0 | 5 | -23.8 | 18.9 | -42.0 | 0.0 | n.s. |
| | Post IV (40 Min) | RPR | 11 | 349.8 | 28.7 | 298.0 | 387.0 | 11 | -9.2 | 17.7 | -38.0 | 25.0 | n.s. |
| | | Placebo | 5 | 338.0 | 17.1 | 324.0 | 366.0 | 5 | -15.2 | 12.7 | -33.0 | 1.0 | n.s. |

FIG. 7

| Parameter | Mean | | p-Value |
|---|---|---|---|
| | Placebo | RPR 102681 | comparison between treatment groups |
| Cmax (ng/mL) | 317.80 | 284.73 | 0.5790 |
| Cmax Log-transformed (ng/mL) | 304.23 | 265.55 | 0.5180 |
| $AUC_{0-t}$ (ng·h/mL) | 334.00 | 326.55 | 0.8770 |
| $AUC_{0-t}$ Log-transformed (ng·h/mL) | 324.47 | 314.25 | 0.8344 |
| $AUC_{0-inf}$ (ng·h/mL) | 360.80 | 362.00 | 0.9810 |
| $AUC_{0-inf}$ Log-transformed (ng·h/mL) | 351.60 | 349.18 | 0.9619 |
| λz (1/hrs) | 0.5716 | 0.5412 | 0.4587 |
| T-1/2 (hr) | 1.2186 | 1.3360 | 0.2632 |
| Vss (L/kg) | 2.41 | 2.73 | 0.5119 |
| CL (mL/h/kg) | 1490 | 1536 | 0.5452 |

FIG. 8

| Parameter | RPR 102681 Dose | Mean | p-value: comparison with baseline | Ratio (%) relative to baseline | 90% CI of Ratio (%) |
|---|---|---|---|---|---|
| Cmax (ng/mL) | Baseline | 284.73 | | | |
| | 200 mg | 276.18 | 0.8191 | 97.0 | 75.1 – 118.9 |
| | 400 mg | 286.82 | 0.9533 | 100.7 | 79.8 – 121.7 |
| | 800 mg | 335.36 | 0.4754 | 117.8 | 76.3 – 159.3 |
| Cmax (ng/mL) Log-transformed | Baseline | 265.55 | | | |
| | 200 mg | 253.28 | 0.6766 | 95.4 | 78.9 – 115.3 |
| | 400 mg | 271.08 | 0.8413 | 102.1 | 86.0 – 121.2 |
| | 800 mg | 279.11 | 0.7310 | 105.1 | 82.5 – 133.8 |
| $AUC_{0-t}$ (ng·h/mL) | Baseline | 326.55 | | | |
| | 200 mg | 316.09 | 0.4821 | 96.8 | 89.2 – 104.4 |
| | 400 mg | 321.91 | 0.7463 | 98.6 | 91.2 – 105.9 |
| | 800 mg | 327.55 | 0.9545 | 100.3 | 91.3 – 109.3 |
| $AUC_{0-t}$ (ng·h/mL) Log-transformed | Baseline | 314.25 | | | |
| | 200 mg | 303.60 | 0.4536 | 96.6 | 89.5 – 104.3 |
| | 400 mg | 313.25 | 0.9407 | 99.7 | 92.6 – 107.3 |
| | 800 mg | 311.00 | 0.8351 | 99.0 | 91.0 – 107.6 |
| $AUC_{0-inf}$ (ng·h/mL) | Baseline | 362.00 | | | |
| | 200 mg | 356.45 | 0.7518 | 98.5 | 90.4 – 106.6 |
| | 400 mg | 355.09 | 0.6766 | 98.1 | 90.4 – 105.7 |
| | 800 mg | 366.64 | 0.8183 | 101.3 | 92.0 – 110.6 |
| $AUC_{0-inf}$ (ng·h/mL) Log-transformed | Baseline | 349.18 | | | |
| | 200 mg | 341.83 | 0.6624 | 97.9 | 90.2 – 106.2 |
| | 400 mg | 344.26 | 0.7434 | 98.6 | 91.7 – 106.0 |
| | 800 mg | 349.78 | 0.9721 | 100.2 | 92.3 – 108.7 |
| λz (1/hrs) | Baseline | 0.5412 | | | |
| | 200 mg | 0.5246 | 0.5381 | 96.9 | 88.7 – 105.2 |
| | 400 mg | 0.5335 | 0.7718 | 98.6 | 90.5 – 106.7 |
| | 800 mg | 0.5404 | 0.9763 | 99.9 | 91.3 – 108.4 |
| T-1/2 (hr) | Baseline | 1.3360 | | | |
| | 200 mg | 1.3576 | 0.7575 | 101.6 | 92.9 – 110.4 |
| | 400 mg | 1.3199 | 0.8179 | 98.8 | 90.1 – 107.5 |
| | 800 mg | 1.3232 | 0.8576 | 99.0 | 90.1 – 108.0 |
| Vss (L/kg) | Baseline | 2.73 | | | |
| | 200 mg | 2.84 | 0.6021 | 103.8 | 91.6 – 116.1 |
| | 400 mg | 2.68 | 0.7967 | 98.1 | 85.8 – 110.4 |
| | 800 mg | 2.74 | 0.9897 | 100.1 | 87.2 – 113.0 |
| CL (mL/h/kg) | Baseline | 1536 | | | |
| | 200 mg | 1580 | 0.5452 | 102.9 | 94.9 – 110.9 |
| | 400 mg | 1547 | 0.8786 | 100.7 | 92.9 – 108.5 |
| | 800 mg | 1544 | 0.9039 | 100.6 | 92.6 – 108.6 |

FIG. 9

| Parameter | RPR 102681 Dose | Mean | p-value: comparison with baseline | Ratio (%) relative to baseline | 90% CI of Ratio (%) |
|---|---|---|---|---|---|
| Cmax (ng/mL) | Baseline | 253.40 | | | |
| | 200 mg | 251.71 | 0.8175 | 99.3 | 94.5 – 104.2 |
| | 400 mg | 244.56 | 0.2284 | 96.5 | 91.7 – 101.3 |
| | 800 mg | 244.22 | 0.2235 | 96.4 | 91.4 – 101.3 |
| Cmax (ng/mL) Log-transformed | Baseline | 249.24 | | | |
| | 200 mg | 249.16 | 0.9901 | 100.0 | 95.1 – 105.1 |
| | 400 mg | 241.68 | 0.3045 | 97.0 | 92.3 – 101.9 |
| | 800 mg | 242.16 | 0.3639 | 97.2 | 92.2 – 102.4 |
| $AUC_{0-4}$ (ng·h/mL) | Baseline | 840.82 | | | |
| | 200 mg | 848.91 | 0.6389 | 101.0 | 97.5 – 104.4 |
| | 400 mg | 818.73 | 0.1931 | 97.4 | 94.0 – 100.7 |
| | 800 mg | 826.00 | 0.3948 | 98.2 | 94.8 – 101.7 |
| $AUC_{0-4}$ (ng·h/mL) Log-transformed | Baseline | 829.07 | | | |
| | 200 mg | 841.43 | 0.4947 | 101.5 | 97.9 – 105.2 |
| | 400 mg | 805.69 | 0.1729 | 97.2 | 93.9 – 100.6 |
| | 800 mg | 818.60 | 0.5536 | 98.7 | 95.3 – 102.3 |

FIG. 10

| Time After Last RPR Dose | Sub No | Day 13 (200 mg) | Day 20 (400 mg) | Day 27 (800 mg) |
|---|---|---|---|---|
| 2-3.5 hours | 58 | 309 | 463 | 450 |
| | 73 | 408 | 1070 | 566 |
| | 76 | 282 | 307 | 545 |
| | 88 | 275 | 336 | 306 |
| Mean | | 318.5 | 544.0 | 466.8 |
| SD | | 61.4 | 357.2 | 118.5 |
| %CV | | 19.3 | 65.7 | 25.4 |
| Median | | 295.5 | 399.5 | 497.5 |
| Min | | 275 | 307 | 306 |
| Max | | 408 | 1070 | 566 |
| 8-11 hours | 7 | 6.18 | 24.7 | 88.1 |
| | 8 | 16 | 28 | 30.9 |
| | 11 | 28 | 27.9 | 32.4 |
| | 12 | 37.8 | 59.5 | 127 |
| | 14 | 7.8 | 29.1 | 31 |
| | 36 | | 67.1 | 90.1 |
| | 52 | 3.58 | 10.6 | 20.2 |
| Mean | | 16.6 | 35.3 | 60.0 |
| SD | | 13.7 | 20.3 | 41.3 |
| %CV | | 82.6 | 57.5 | 68.8 |
| Median | | 11.9 | 28.0 | 32.4 |
| Min | | 3.58 | 10.6 | 20.2 |
| Max | | 37.8 | 67.1 | 127 |

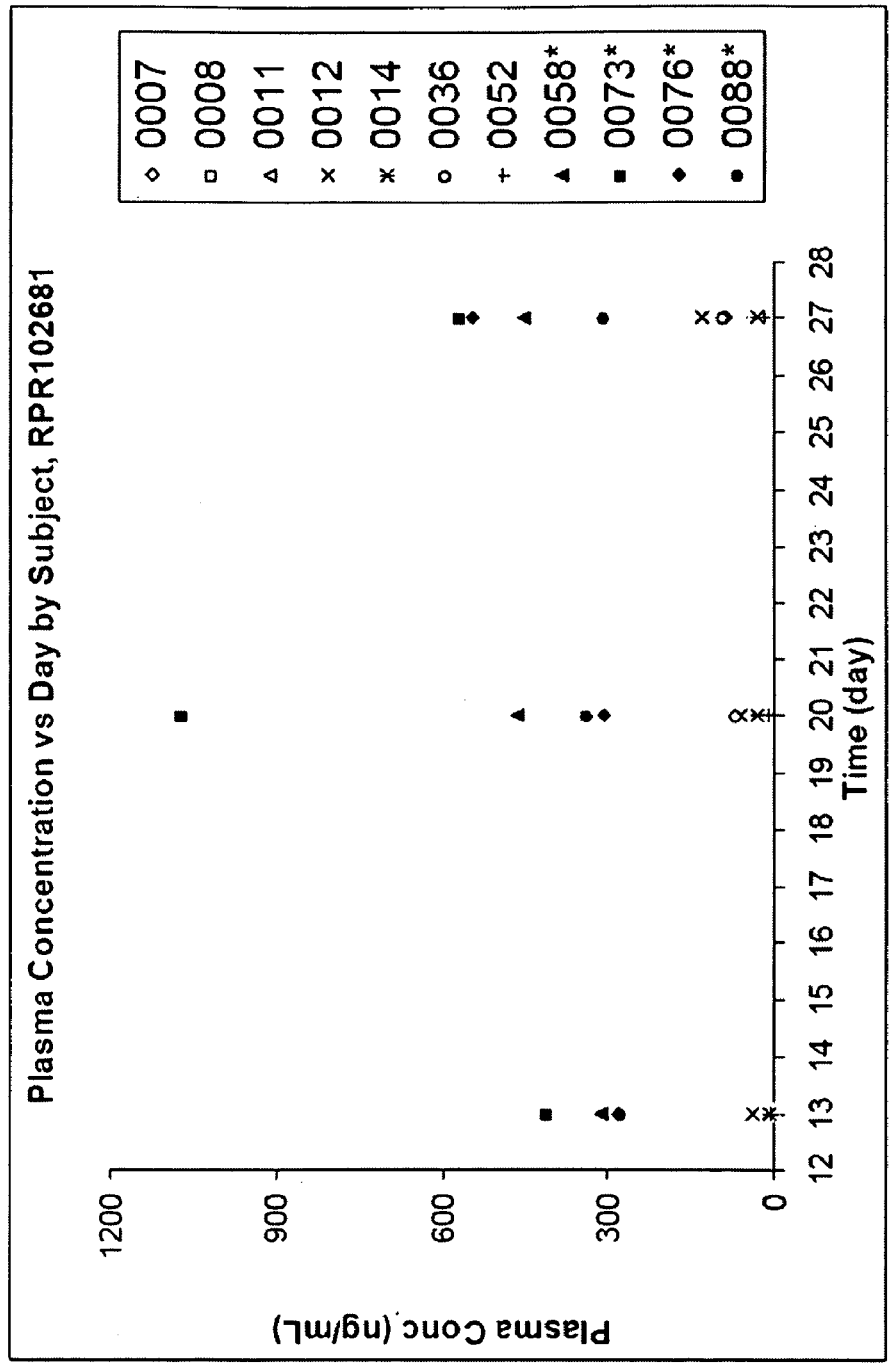

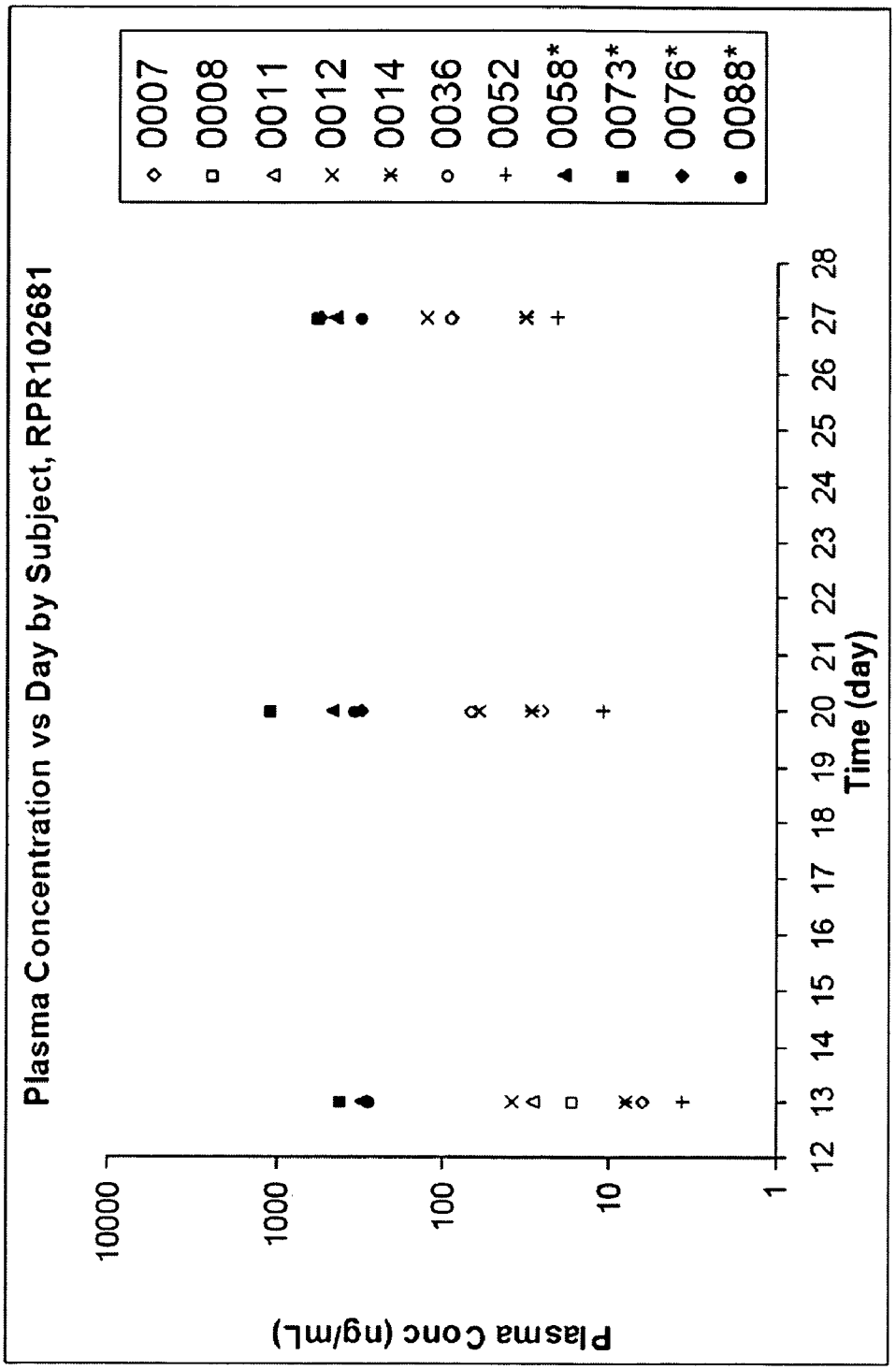

FIG. 13

| Day | At 95 Minutes Post Dose | | | | | | At 215 Minutes Post Dose | | | | | |
|---|---|---|---|---|---|---|---|---|---|---|---|---|
| | N | Mean | SD | Median | Min | Max | N | Mean | SD | Median | Min | Max |
| 13 | 10 | 255.4 | 240.6 | 214.0 | 4.27 | 772 | 12 | 140.4 | 101.4 | 116.0 | 7.64 | 326 |
| 14 | 12 | 224.0 | 212.1 | 169.0 | 5.61 | 788 | 12 | 156.7 | 138.6 | 95.1 | 3.32 | 393 |
| 15 | 12 | 249.7 | 301.6 | 182.0 | 7.01 | 1130 | 12 | 123.7 | 86.2 | 102.5 | 8.3 | 297 |
| 20 | 9 | 492.8 | 332.2 | 401.0 | 111 | 1110 | 10 | 185.5 | 77.1 | 189.5 | 52.9 | 293 |
| 21 | 12 | 348.4 | 345.3 | 278.5 | 3.56 | 1300 | 11 | 219.2 | 243.3 | 126.0 | 1.7 | 714 |
| 22 | 12 | 419.2 | 263.1 | 389.0 | 6.02 | 942 | 12 | 265.7 | 333.0 | 123.5 | 3.69 | 1160 |
| 27 | 10 | 516.7 | 454.9 | 531.5 | 3.83 | 1390 | 11 | 294.3 | 192.9 | 274.0 | 9.45 | 724 |
| 28 | 12 | 467.5 | 347.3 | 474.0 | 19.4 | 989 | 11 | 330.0 | 330.0 | 251.0 | 10 | 985 |
| 29 | 11 | 341.4 | 274.7 | 422.0 | 10.9 | 771 | 11 | 271.8 | 324.9 | 150.0 | 5.07 | 922 |

FIG. 14

Treatment Group: RPR 102681 (N=12)

| Subject No | Average Concentration Of 3 days * at 95 min post-dose (ng/mL) | | | Average Concentration Of 3 days * at 215 min post-dose | | |
|---|---|---|---|---|---|---|
| | 200 mg | 400 mg | 800 mg | 200 mg | 400 mg | 800 mg |
| 1 | 76.63 | 106.19 | 20.54 | 32.95 | 66.80 | 10.68 |
| 7 | 65.25 | 281.33 | 441.75 | 139.93 | 196.33 | 262.23 |
| 8 | 281.00 | 440.33 | 388.75 | 148.33 | 128.87 | 160.60 |
| 11 | 188.67 | 245.00 | 441.97 | 84.73 | 112.33 | 125.09 |
| 12 | 93.80 | 358.67 | 550.33 | 227.03 | 236.00 | 289.00 |
| 14 | 160.33 | 450.67 | 913.67 | 101.33 | 140.35 | 254.00 |
| 36 | 120.77 | 172.40 | 292.00 | 247.00 | 685.00 | 834.67 |
| 52 | 98.03 | 382.33 | 519.67 | 111.87 | 84.70 | 73.00 |
| 58 | 251.00 | 660.00 | 808.33 | 89.17 | 171.00 | 342.67 |
| 73 | 896.67 | 1121.00 | 499.95 | 285.67 | 903.00 | 128.04 |
| 76 | 412.50 | 563.74 | 185.33 | 110.63 | 189.27 | 445.67 |
| 88 | 260.67 | 279.67 | 225.43 | 104.73 | 147.33 | 497.67 |
| Mean | 242.11 | 421.78 | 440.64 | 140.28 | 255.08 | 285.28 |
| SD | 230.63 | 270.60 | 251.09 | 74.96 | 260.32 | 226.41 |
| %CV | 95.26 | 64.16 | 56.98 | 53.43 | 102.05 | 79.37 |
| Median | 174.50 | 370.50 | 441.86 | 111.25 | 159.17 | 258.12 |
| Min | 65.25 | 106.19 | 20.54 | 32.95 | 66.80 | 10.68 |
| Max | 896.67 | 1121.00 | 913.67 | 285.67 | 903.00 | 834.67 |

FIG. 16

| Time After Dose | RPR 102681 Dose | Least-Squares Mean (ng/mL) | Difference from (p-value) | |
|---|---|---|---|---|
| | | | 200 mg | 400 mg |
| 95 min | 200 mg | 1.21 | | |
| | 400 mg | 1.06 | -0.14 (0.3981) | |
| | 800 mg | 0.59 | -0.62 (0.0004)** | -0.47 (0.0062)** |
| 215 min | 200 mg | 0.70 | | |
| | 400 mg | 0.60 | -0.10 (0.2795) | |
| | 800 mg | 0.38 | -0.32 (0.0014)** | -0.22 (0.0313)* |

*significant at p<0.05
**significant at p<0.01

FIG. 18

| Day | Group | N | Mean | SD | Min | Max | Test Change from Day 0 | |
|---|---|---|---|---|---|---|---|---|
| | | | | | | | P-value Paired T test | P-value Signed Rank |
| 0 | RPR | 12 | 10.4 | 3.8 | 2.6 | 15.6 | | |
| | Placebo | 7 | 9.1 | 4.0 | 3.3 | 15.7 | | |
| 15 | RPR | 12 | 12.0 | 4.9 | 6.9 | 22.3 | n.s. | n.s. |
| | Placebo | 6 | 11.5 | 2.2 | 9.1 | 14.6 | n.s. | n.s. |
| 22 | RPR | 12 | 15.8 | 11.7 | 7.0 | 49.4 | n.s. | n.s. |
| | Placebo | 5 | 13.7 | 3.5 | 8.7 | 18.2 | n.s. | n.s. |
| 29 | RPR | 11 | 12.7 | 6.7 | 6.8 | 30.9 | n.s. | n.s. |
| | Placebo | 5 | 13.5 | 3.3 | 9.9 | 17.6 | 0.016 | 0.063 |

* Only P-values <0.05 are reported here. (n.s.) means not significant at α=0.05 level.

FIG. 19

| Day | Time | Group | Prolactin | | | | | Change from Pre Infusion | | | | | P- Paired T- Test | P-Signed Rank Test |
|---|---|---|---|---|---|---|---|---|---|---|---|---|---|---|
| | | | N | Mean | SD | Min | Max | N | Mean | SD | Min | Max | | |
| 15 | Pre-I.V. | RPR | 12 | 12.0 | 4.9 | 6.9 | 22.3 | 0 | | | | | | |
| | | Placebo | 6 | 11.5 | 2.2 | 9.1 | 14.6 | 0 | | | | | | |
| | Post Saline | RPR | 12 | 5.4 | 2.3 | 2.7 | 8.5 | 12 | -6.6 | 3.7 | -14.1 | -0.3 | <0.001 | <0.001 |
| | | Placebo | 5 | 5.5 | 2.2 | 3.2 | 8.6 | 5 | -6.1 | 4.2 | -11.0 | -0.9 | 0.031 | 0.063 |
| | Post Cocaine | RPR | 12 | 5.1 | 1.8 | 2.6 | 8.9 | 12 | -7.0 | 4.8 | -18.5 | -1.6 | <0.001 | <0.001 |
| | | Placebo | 6 | 5.2 | 2.4 | 2.6 | 9.2 | 6 | -6.3 | 3.7 | -11.2 | -0.3 | 0.009 | 0.031 |
| 22 | Pre-I.V. | RPR | 12 | 15.8 | 11.7 | 7.0 | 49.4 | 0 | | | | | | |
| | | Placebo | 5 | 13.7 | 3.5 | 8.7 | 18.2 | 0 | | | | | | |
| | Post Saline | RPR | 12 | 5.2 | 1.8 | 2.8 | 7.8 | 12 | -10.6 | 12.4 | -46.6 | -0.7 | 0.013 | <0.001 |
| | | Placebo | 5 | 5.8 | 3.7 | 2.9 | 11.3 | 5 | -7.8 | 5.4 | -15.2 | -1.2 | 0.032 | 0.063 |
| | Post Cocaine | RPR | 12 | 5.1 | 1.8 | 2.6 | 8.9 | 12 | -10.6 | 11.5 | -44.2 | -2.1 | 0.009 | <0.001 |
| | | Placebo | 4 | 5.9 | 1.7 | 3.7 | 7.7 | 4 | -7.7 | 5.0 | -14.5 | -3.2 | 0.054 | n.s. |
| 29 | Pre-I.V. | RPR | 11 | 12.7 | 6.7 | 6.8 | 30.9 | 0 | | | | | | |
| | | Placebo | 5 | 13.5 | 3.3 | 9.9 | 17.6 | 0 | | | | | | |
| | Post Saline | RPR | 11 | 5.9 | 1.8 | 4.5 | 9.3 | 11 | -6.8 | 5.5 | -21.7 | -2.2 | 0.002 | <0.001 |
| | | Placebo | 5 | 6.0 | 3.4 | 2.8 | 10.6 | 5 | -7.6 | 3.3 | -13.1 | -4.7 | 0.007 | 0.063 |
| | Post Cocaine | RPR | 11 | 4.2 | 1.7 | 2.5 | 7.8 | 11 | -8.5 | 6.3 | -25.9 | -3.7 | 0.001 | <0.001 |
| | | Placebo | 4 | 6.4 | 3.1 | 4.2 | 11.0 | 4 | -7.8 | 4.0 | -13.4 | -4.7 | 0.030 | n.s. |

FIG. 20

| Day | Group | Post Saline | | | Post Cocaine | | | Post Cocaine-Post Saline | | | P-Paired T-Test | P-Signed rank Test |
|---|---|---|---|---|---|---|---|---|---|---|---|---|
| | | N | Mean | SD | N | Mean | SD | N | Mean | SD | | |
| 15 | RPR102681 | 12 | 5.4 | 2.3 | 12 | 5.1 | 1.8 | 12 | -0.3 | 2.6 | n.s. | n.s. |
| | Placebo | 5 | 5.5 | 2.2 | 6 | 5.2 | 2.4 | 5 | 0.2 | 1.5 | n.s. | n.s. |
| 22 | RPR102681 | 12 | 5.2 | 1.8 | 12 | 5.1 | 1.8 | 12 | -0.1 | 2.0 | n.s. | n.s. |
| | Placebo | 5 | 5.8 | 3.7 | 4 | 5.9 | 1.7 | 4 | 0.6 | 3.0 | n.s. | n.s. |
| 29 | RPR102681 | 11 | 5.9 | 1.8 | 11 | 4.2 | 1.7 | 11 | -1.7 | 1.5 | 0.004 | 0.0186 |
| | Placebo | 5 | 6.0 | 3.4 | 4 | 6.4 | 3.1 | 4 | -0.3 | 2.1 | n.s. | n.s. |

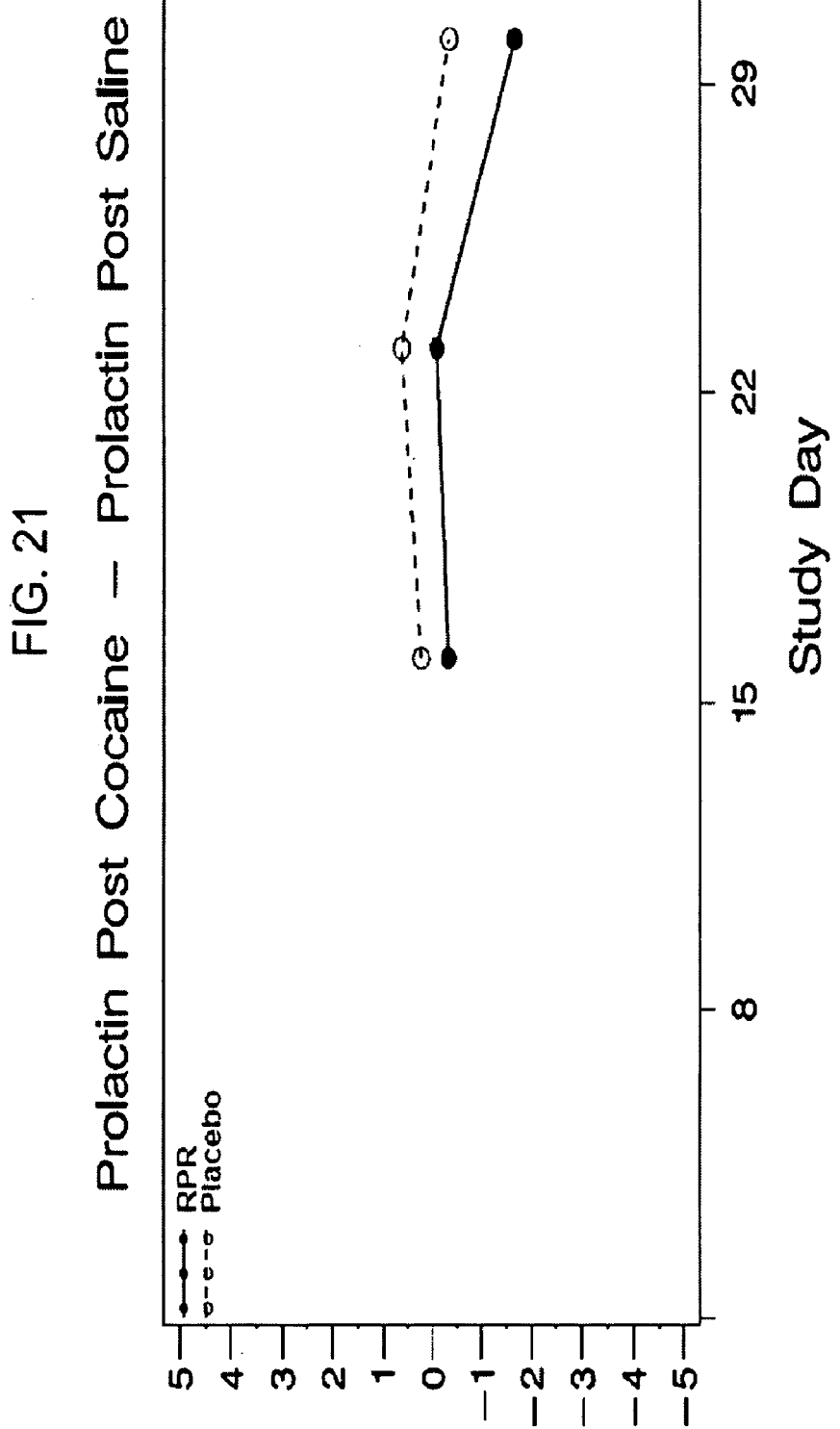

FIG. 23

RPR102681 CONCENTRATION (ng/ml)

| Day of Study | 6 | 13 | 20 | 27 | Dosing Schedule |
|---|---|---|---|---|---|
| Total oral daily dose of RPR102681 | 0 mg | 200 mg Bid | 400 mg Bid | 800 mg Bid | |
| 0007 | 0.00 | 6.20 | 24.70 | 88.10 | A |
| 0008 | 0.00 | 16.00 | 28.00 | 30.90 | A |
| 0011 | 0.00 | 28.00 | 27.90 | 32.40 | A |
| 0012 | 0.00 | 37.80 | 59.50 | 127.00 | A |
| 0014 | 0.00 | 7.80 | 29.09 | 30.98 | A |
| 0036 | 0.00 | xx | 67.10 | 90.09 | A |
| 0052 | 0.00 | 3.58 | 10.59 | 20.24 | A |
| 0058 | 0.00 | 308.93 | 462.85 | 450.38 | B |
| 0073 | 0.00 | 407.57 | 1071.15 | 565.81 | B |
| 0076 | 0.00 | 281.96 | 307.23 | 545.00 | B |
| 0088 | 0.00 | 275.29 | 335.81 | 306.03 | B |

FIG. 25

Pearson Correlation Coefficients and Corresponding P Values [R(p)]

| | $BP_{df}(VS)$ | BPdf(Pu) | BPdf(CN) |
|---|---|---|---|
| $RPRconcPET_0$* | 0.41(0.180) | -0.30(0.336) | 0.0027(0.994) |
| $Prolactin_{df}$ | 0.57(0.016) | -0.01(0.954) | 0.03(0.905) |

*RPR 102681 concentration at PET start time point(PET0)
BP(baseline) was obtained on day 6.
BP(RPR) is the mean of the BPs on days 13, 20, and 27.
VS = ventral striatum
Pu = putamen
CN = caudate nucleus
BPdf=BP(RPR)-BP(baseline).
Prolactin_df=prolactin(RPR)-prolactin(baseline).

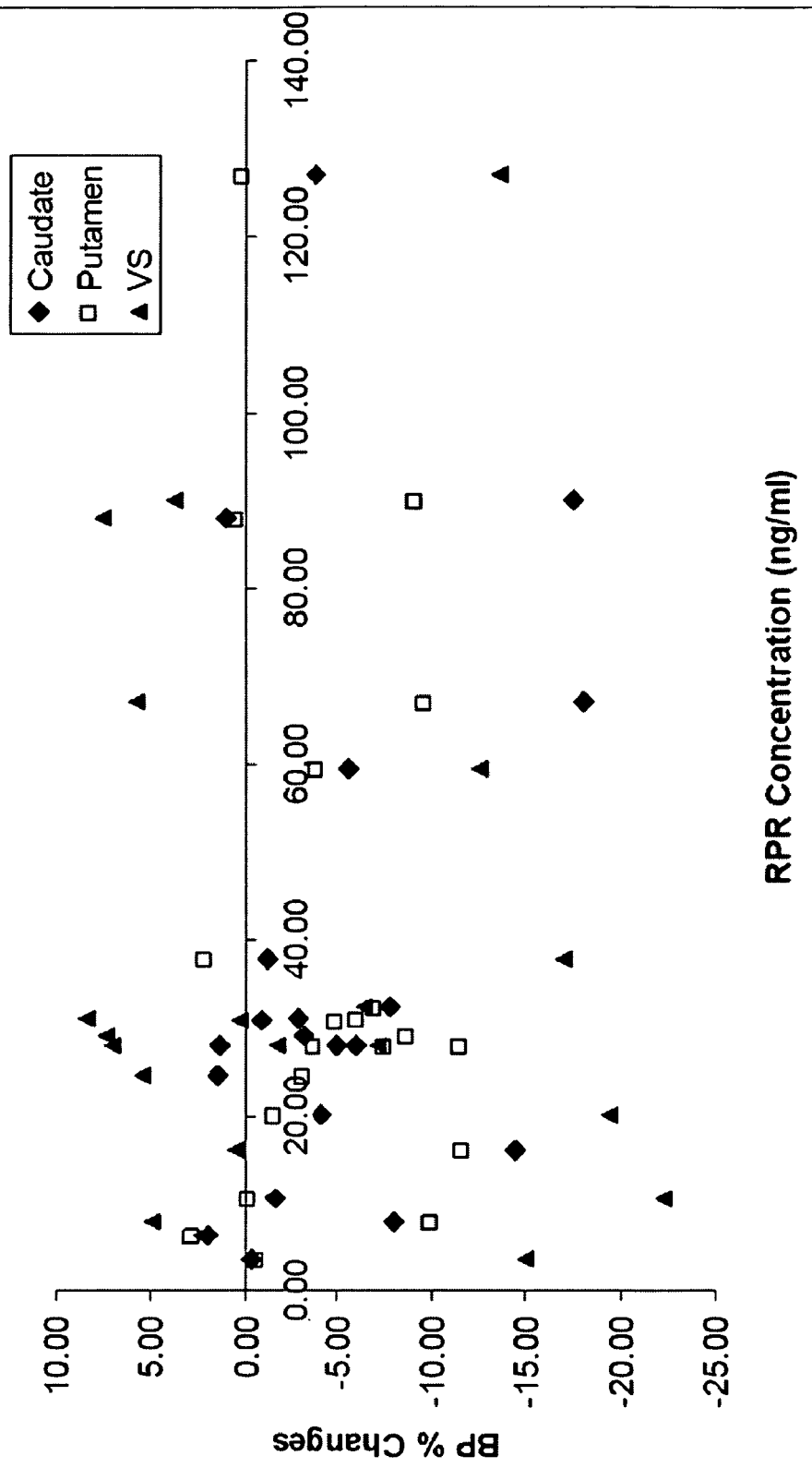

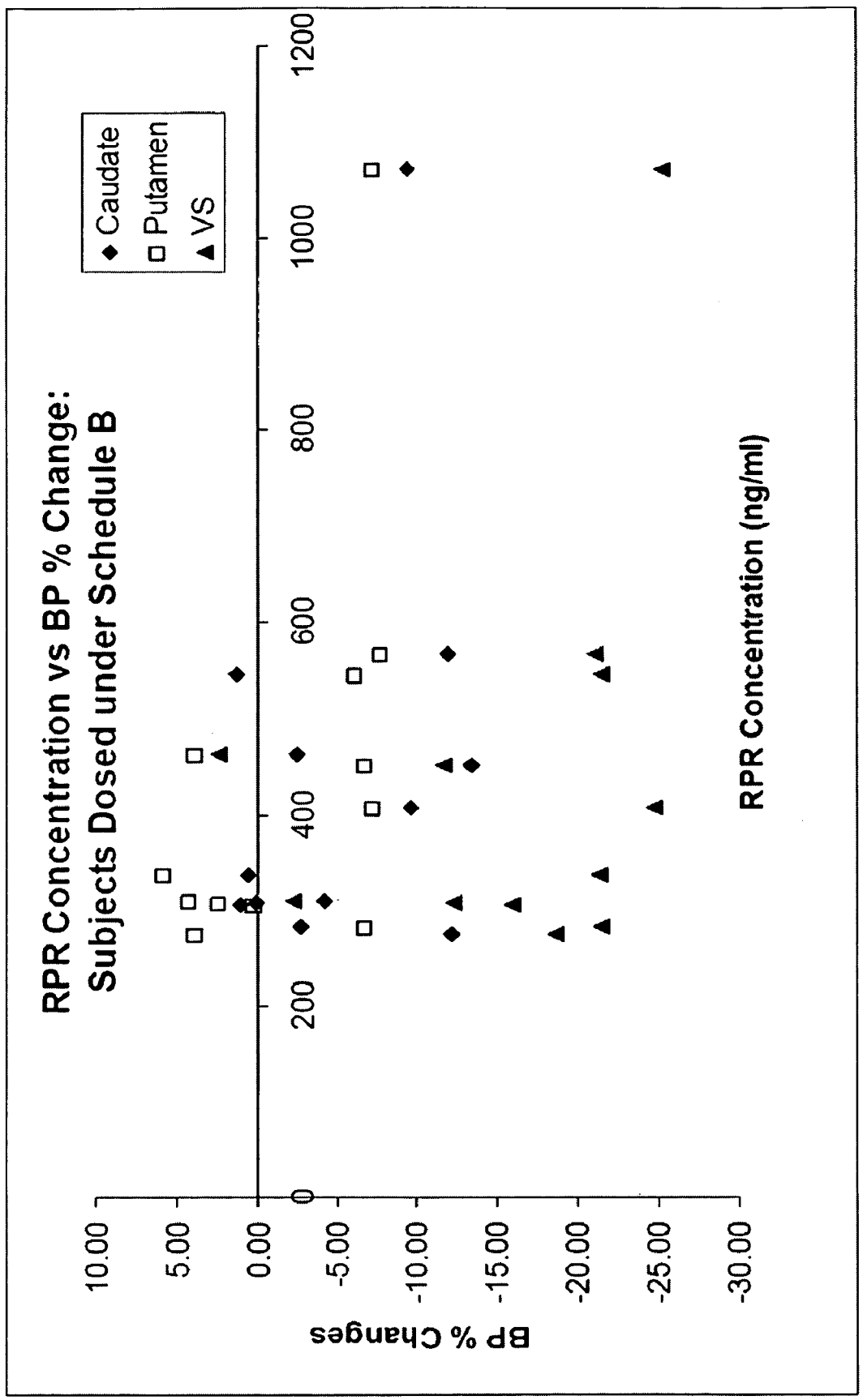

METHODS FOR TREATING SCHIZOPHRENIA

RELATED APPLICATIONS

The present application claims the benefit of priority to U.S. Provisional Patent Application Nos. 61/032,010 filed Feb. 27, 2008 entitled "Methods for Treating Schizophrenia," and 61/038,451 filed Mar. 21, 2008 entitled "Methods for Treating Schizophrenia" the entire contents of each are hereby incorporated by reference.

GOVERNMENT SUPPORT

This invention was made using funds from the National Institute of Health (Study ID# NIDA-CPU-0003-1). The Government has certain rights in this invention.

FIELD OF THE INVENTION

This invention relates to methods for treating conditions or symptoms of certain pathological or psychological conditions in mammals. In particular, this invention relates to methods for treating schizophrenia.

BACKGROUND

Schizophrenia is a chronic, severe, and disabling brain disorder that has been recognized throughout recorded history. It affects about 1 percent of the population. The distressing symptoms and the deterioration and decline associated with schizophrenia make it one of the most severe mental illnesses from which a patient can suffer. Although the true etiology of schizophrenia remains unknown, a substantial body of research suggests that dopamine plays a key role in its pathophysiology.

Schizophrenia is a syndrome characterized by three clusters of symptoms including positive symptoms in the form of hallucinations and delusions, negative symptoms such as anhedonia and poverty of speech, and cognitive impairment, especially memory and executive functions. It is a debilitating mental illness that typically strikes in early adolescence and leads to major deterioration in social and vocational functions.

In schizophrenia there is an increase in dopamine transmission between the substantia nigra to the caudate nucleus-putamen (neostriatum) compared with normal. Dopamine transmission, however, is reduced in other dopaminergic pathways, such as in the mesolimbic forebrain and the tuberoinfundibular system. The dopamine hypothesis of schizophrenia proposes that increased levels of dopamine or dopamine receptors in the dorsal and/or ventral striatum underlie this disorder.

Available antipsyotics (neuroleptics) both typical and atypical are efficacious in treating positive symptoms of schizophrenia. However, these drugs may cause serious side effects, some of which may be irreversible, such as, tardive dyskinesia. Additionally many patients fail to respond adequately to neuroleptics and may develop residual symptoms with functional and social impairment. About 30% of patients show treatment resistance to neuroleptics and continue to have moderate to sever positive symptoms. These treatment resistant patients require the addition of other medications. Most of the available medications for treating schizophrenia have minimal to no effect on negative symptoms and cognitive functions, a problem that is currently the focus of medication development in schizophrenia. Because of the shortcomings of the currently available treatments there is a search for other more effective methods of treatment.

SUMMARY

Novel methods for using the compound of formula (I), a pyrrolidine compound, are disclosed. These methods can be used in treating conditions or symptoms of certain pathological or psychological conditions in mammalian brains. For example, these methods may be used in treating diseases caused by an increase in dopaminergic activity in the basal ganglia, specifically in ventral striatum and caudate nucleus. These methods may also be used in treating schizophrenia.

BRIEF DESCRIPTION OF THE DRAWINGS

The features and nature of the present invention will become more apparent from the detailed description set forth below when taken in conjunction with the drawings in which like reference characters identify correspondingly throughout and wherein:

FIG. 1 is tabulated data showing a cocaine infusion session schedule.

FIG. 2 is tabulated data showing the pre-infusion average and post-infusion maximum values for heart rate, systolic blood pressure and diastolic blood pressure.

FIG. 3 is tabulated data showing P-values of pair-wise comparisons with respect to column variables from RPR 102681 group.

FIGS. 4A-4F are graphical depictions of average differences between maximum post cocaine values and maximum post saline values over time.

FIG. 5 is tabulated data showing ECG summary statistics for non-infusion days.

FIG. 6A is tabulated data showing ECG comparisons between intake screening (days−7 to 1) and each of the pre-infusion measurements on days 8, 15, 22, and 29 when cocaine 40 mg was administered.

FIGS. 6B-D are tabulated data showing results of a Signed Rank Test used to evaluate change from pre-infusion baseline to measurements obtained post cocaine infusion.

FIG. 7 is tabulated data showing the results of a comparison of cocaine pharmacokinetics parameters at baseline between placebo and RPR 102681 groups.

FIG. 8 is tabulated data showing the results of a comparison between cocaine pharmacokinetics parameters at the post-treatment RPR 102681 doses and their baseline values.

FIG. 9 is tabulated data showing the results of a comparison between BE pharmacokinetics parameters at the post-treatment RPR 102681 doses and their baseline values.

FIG. 10 is tabulated data showing plasma concentrations for 11 RPR 102681 subjects at 2-3.5 hours and 8-11 hours post treatment.

FIGS. 11A and 11B are graphical depictions of the plasma concentration-time profile for all subjects by day in linear and semilogarithmic scales.

FIGS. 13 and 14 are tabulated data showing summary statistics for RPR 102681 concentrations at 95 minutes and 215 minutes, and average of 3 days after RPR 102681 dose.

FIG. 16 is tabulated data showing results of the dose-proportionality analysis where dose-normalized RPR 102681 concentrations are compared between RPR 102681 groups.

FIG. 18 is tabulated data showing a comparison of prolactin value at day 0 and prior to infusion on days 15, 22, and 29.

FIG. 19 is tabulated data showing average prolactin levels as well as average change from pre infusion baseline by study day, time point and group.

FIG. 20 is tabulated data showing a comparison of prolactin values between post cocaine infusion and post saline infusions.

FIG. 21 is a graphical depiction of data comparing prolactin values post cocaine infusion to post saline infusions.

FIG. 23 is tabulated data showing plasma concentrations of RPR 102681 in ng/ml for twelve cocaine users at weekly intervals on days 6, 13, 20, and 27, for four weeks of treatment with RPR 102681 orally twice daily, 200 mg on days 9-15, 400 mg on days 16-22, and 800 mg on days 23-29 (Dosing Schedules A and B).

FIG. 25 is tabulated data showing plasma prolactin concentrations and RPR concentrations and binding potential (BP) estimates by PET after the administration of [$^{11}$C]-raclopride for six cocaine users at weekly intervals on days 6, 13, 20, and 27, for four weeks of treatment with RPR 102681 orally twice daily at 6:00 AM and 5:00 PM, 200 mg on days 9-15, 400 mg on days 16-22, and 800 mg on days 23-29 (Dosing Schedules A).

FIG. 26A is a graphical depiction of % BP change plotted against RPR 102681 plasma concentration for those subjects who received RPR 102681 doses under Dosing Schedule A.

FIG. 26B is a graphical depiction of % BP change plotted against RPR 102681 plasma concentration for those subjects who received RPR 102681 doses under Dosing Schedule B.

DETAILED DESCRIPTION

Figure 4C:
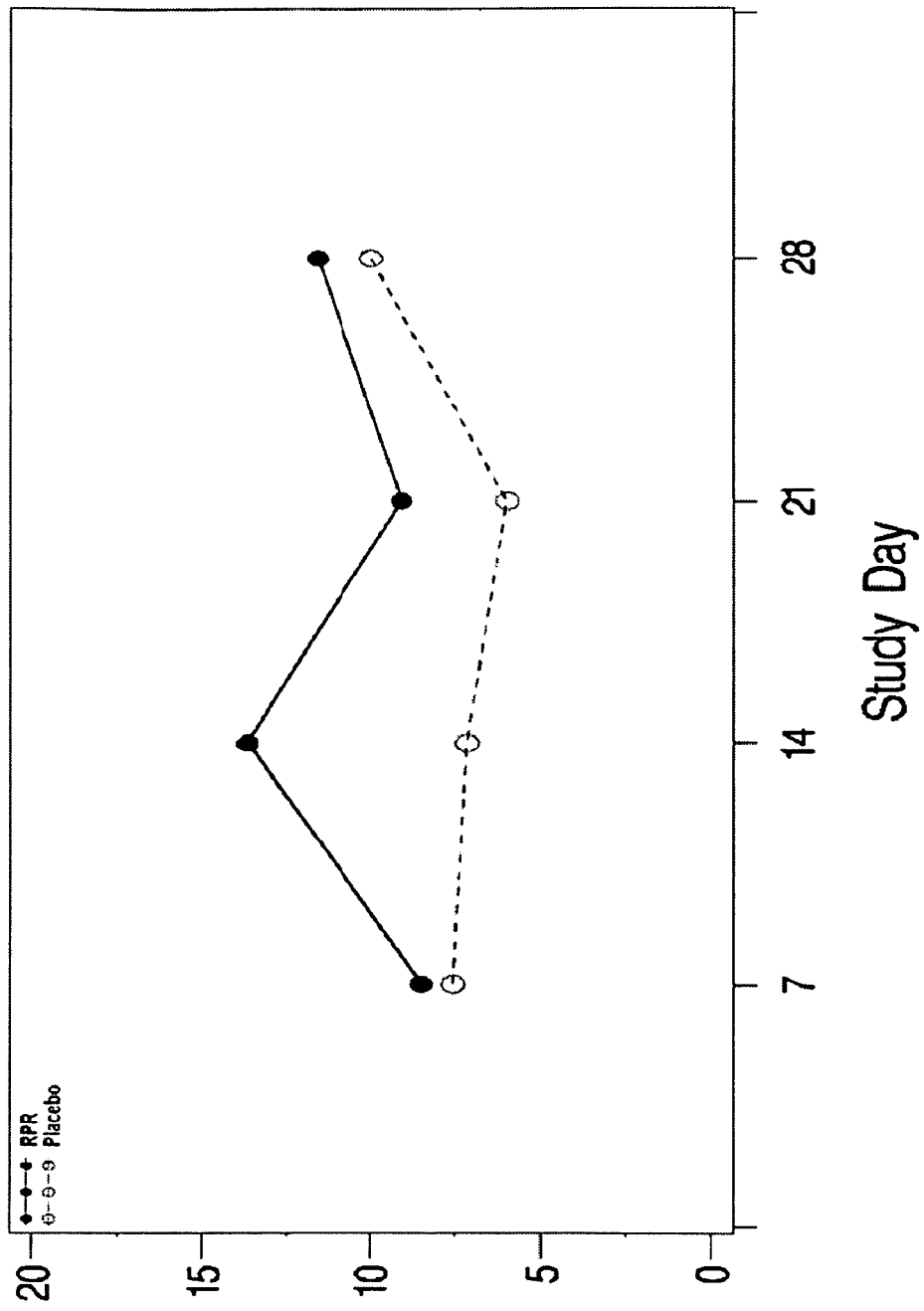
Figure 12A:
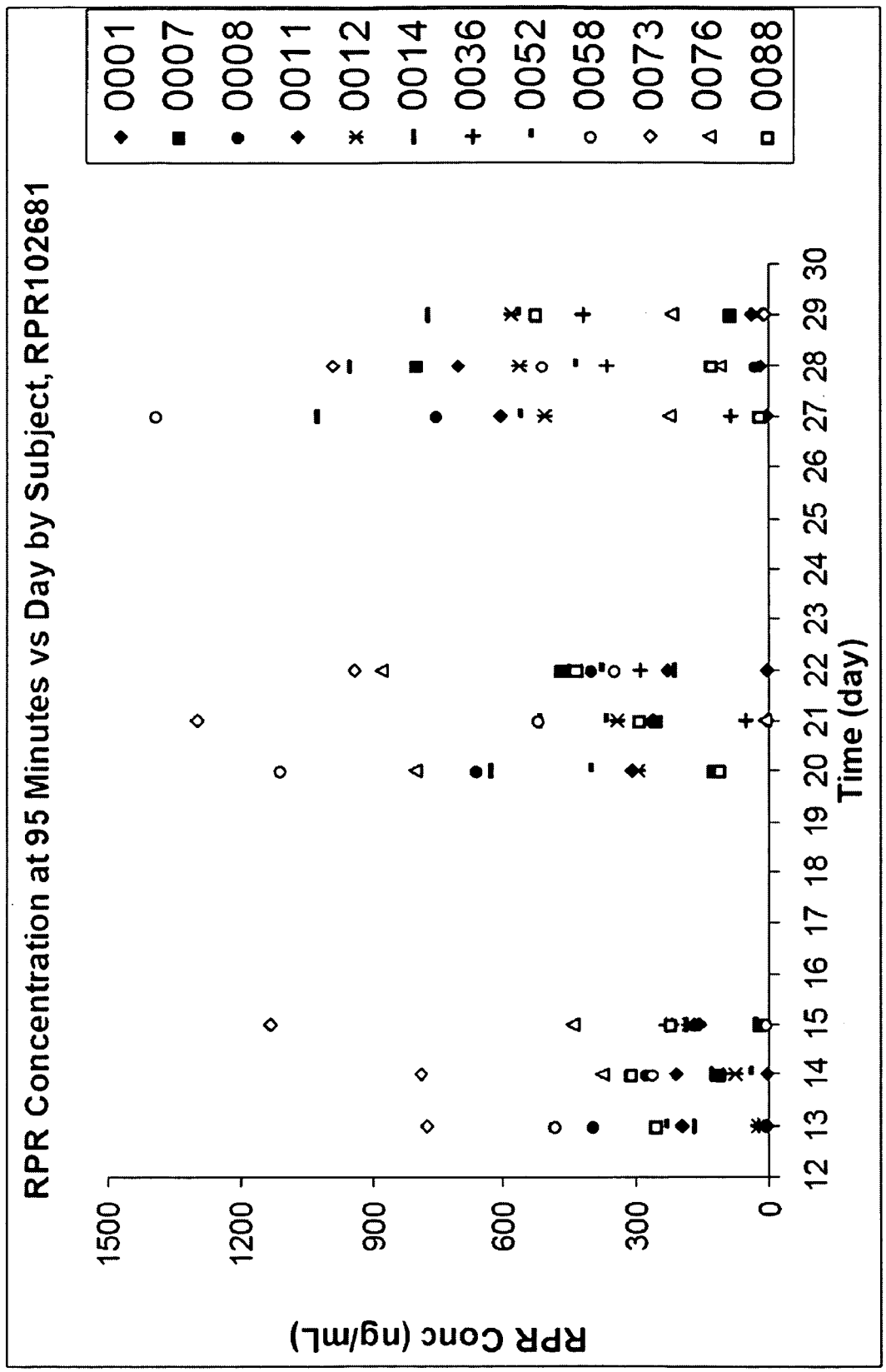
FIGS. 12A-12D are graphical depictions of the RPR 102681 concentrations at 95 minutes and 215 minutes after RPR 102681 dose on linear and semilogarithmic scales.
Figure 12B:
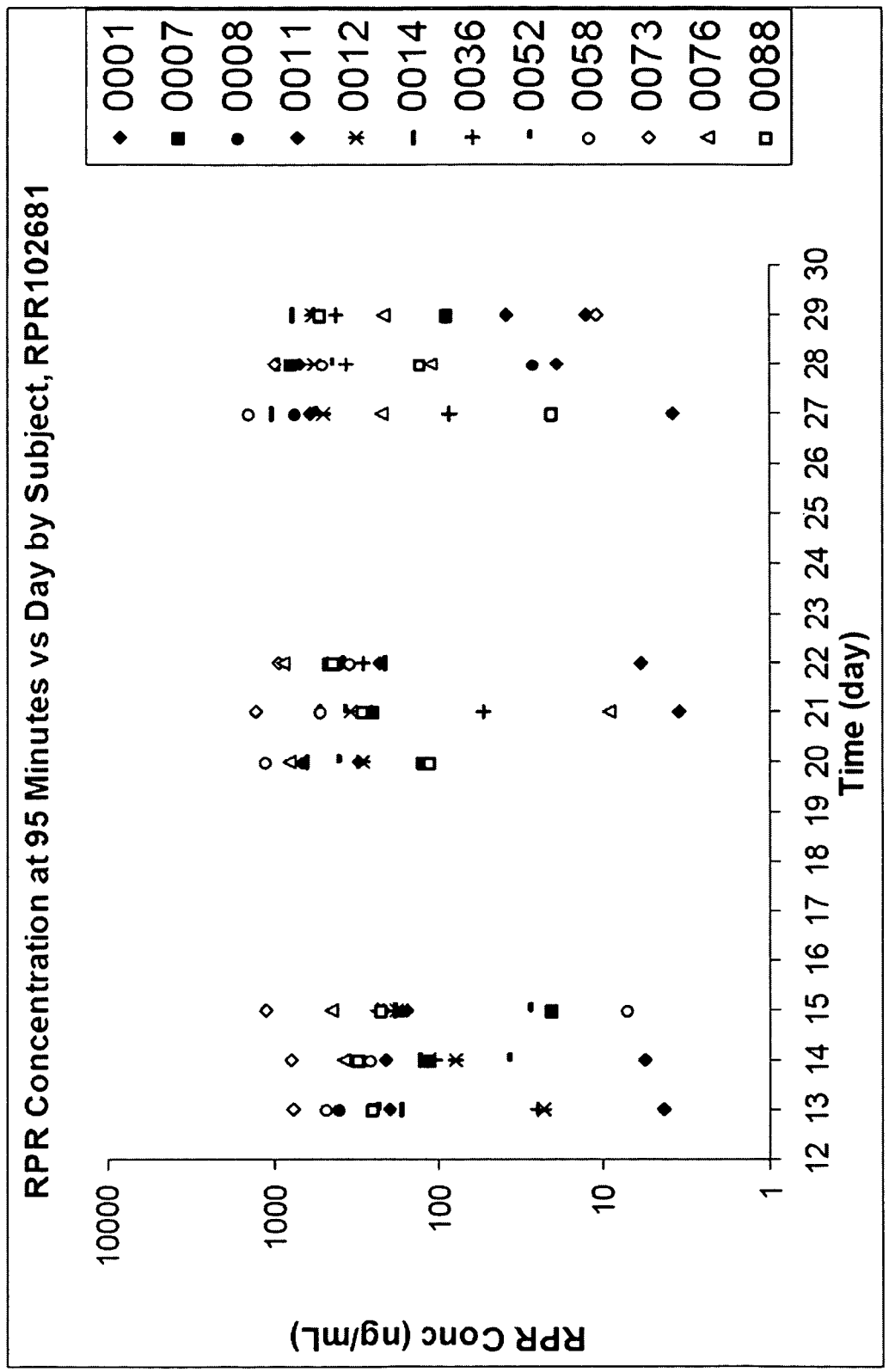
Figure 12C:
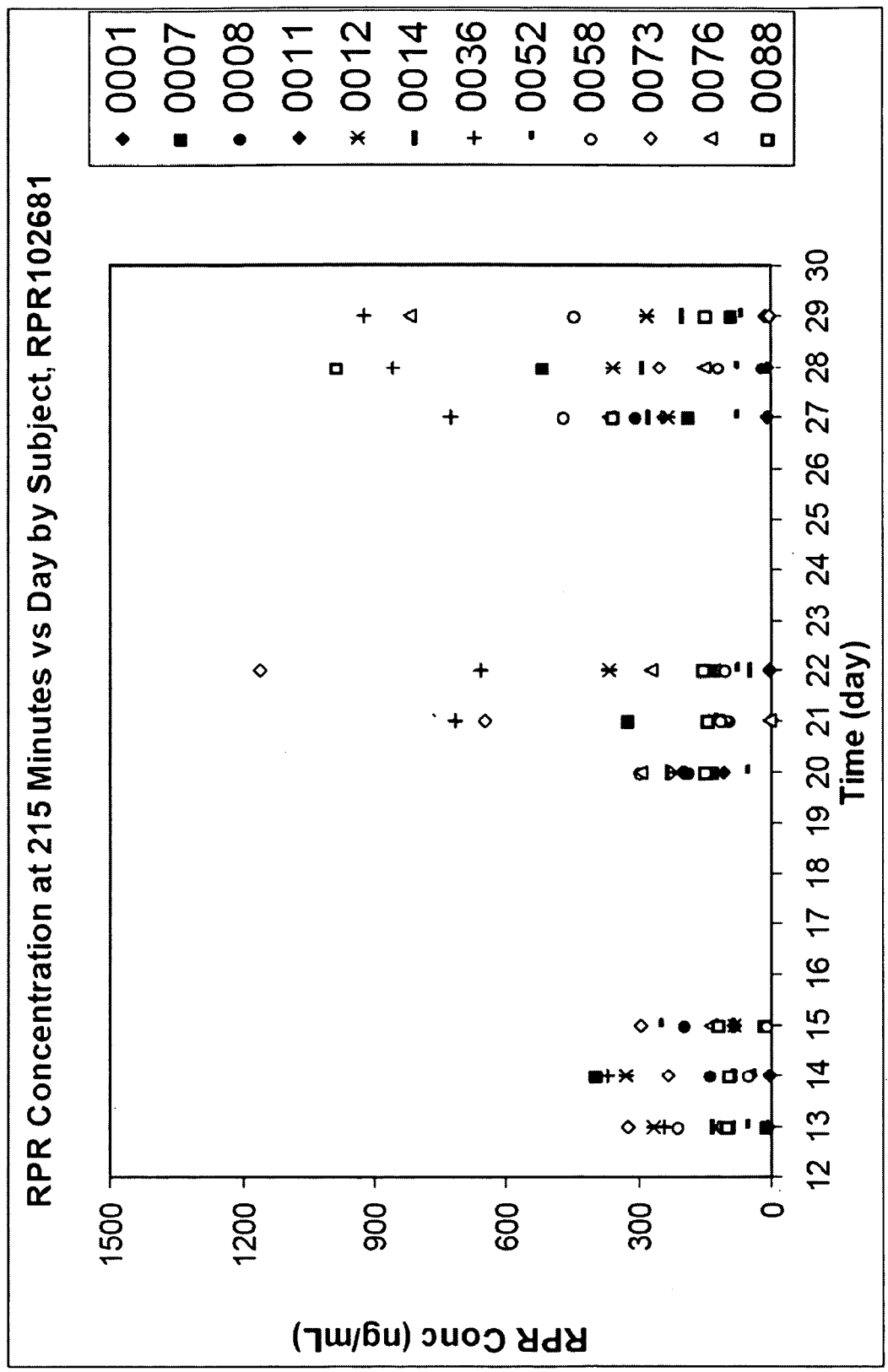
Figure 12D:
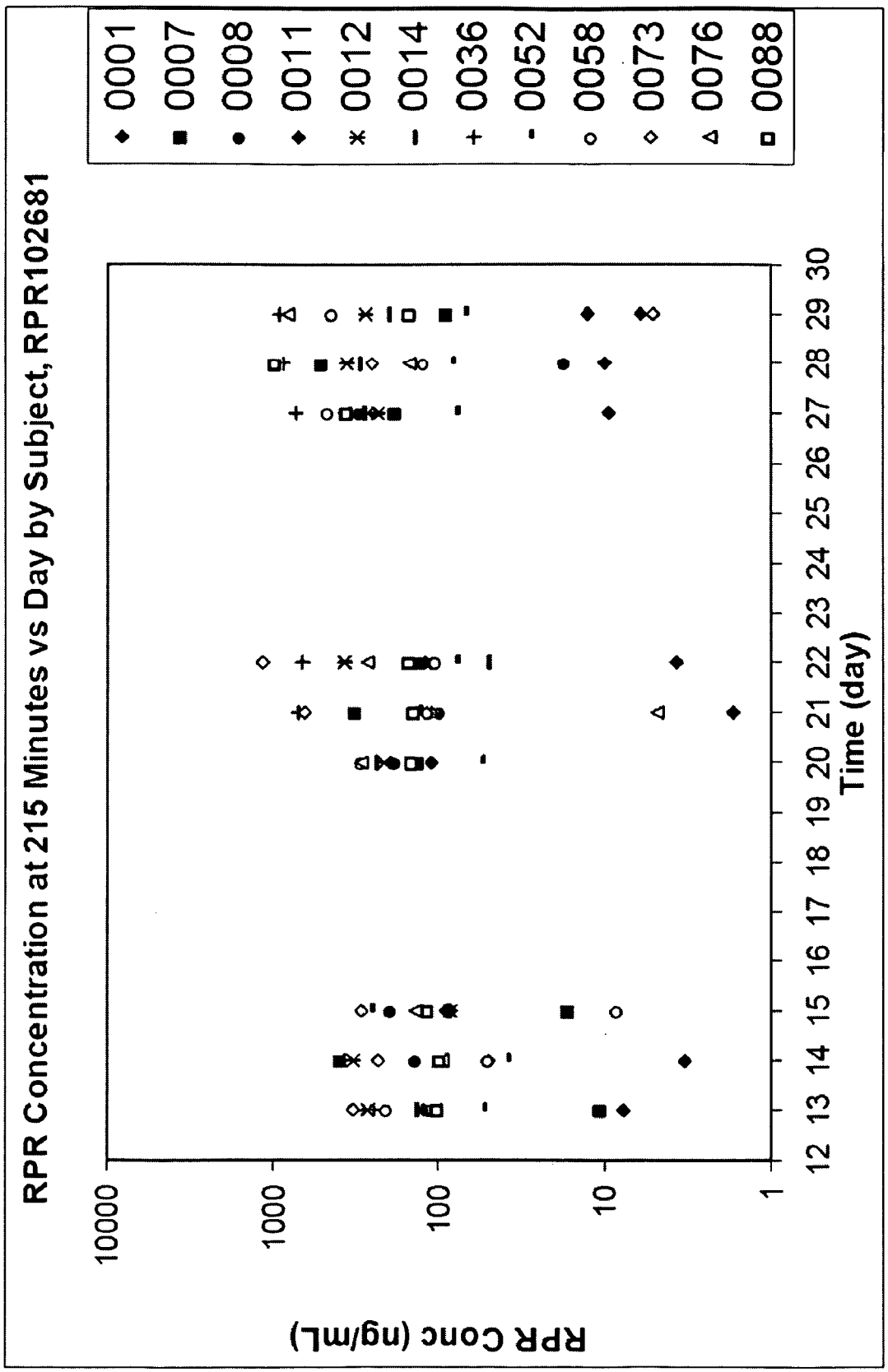

In this description, the terms "the compound of formula (I)," "RPR 102681" and "Aseripide" are used interchangeably. The word "exemplary" is used herein to mean "serving as an example, instance, or illustration." Any implementation described herein as "exemplary" is not necessarily to be construed as preferred or advantageous over other implementations.

Cholecystokinin (CCK) is a neuropeptide in the central nervous system that affects dopaminergic function. It has been hypothesized that in schizophrenia there might be an imbalance between CCK and dopamine in the mesolimbic dopamine system. CCK coexists with dopamine in the mesolimbic pathway and modulates the release of dopamine. Studies have shown that levels of acetylcholine and dopamine are affected by exogenous CCK. CCK, in its ability as a neurotransmitter, has been implicated in both normal and abnormal brain function.

CCK is synthesized de novo in the brain. CCK has been shown to both induce excitation of central neurons and inhibit postsynaptic effects. This is in accordance with morphological findings suggesting that CCK is present in both excitatory and inhibitory neurons. It has been shown that CCK modulates the release of dopamine and that dopaminergic compounds modulate the release of CCK. Similarly, CCK has been found to both facilitate and inhibit dopaminergic activity.

There are two types of CCK receptors: CCK-A and CCK-B. Both of these receptors are widespread through out the central nervous system. CCK-A are present in certain brain areas, namely, in the area postrema, nucleus of solitary tract and interpeduncular, dorsal raphe, nucleus accumbens septi, substantia nigra and ventral tegmental area. CCK-B receptors are generally present in high concentrations in the striatum (caudate nucleus and putamen), cerebral cortex and the limbic system. CCK-B receptors are also present outside the brain since they are equivalent to gastrin receptors found, for example, in the stomach.

It has been discovered that the compound known as (2S)-2-{3-[3-({[(2R,4R)-4-tert-Butoxycarbonyl-2-(2-fluorophenyl)]-3-thiazolidinyl}carbonylmethyl) ureido]phenyl}propionic acid, also known as Aseripide or RPR 102681, having the formula

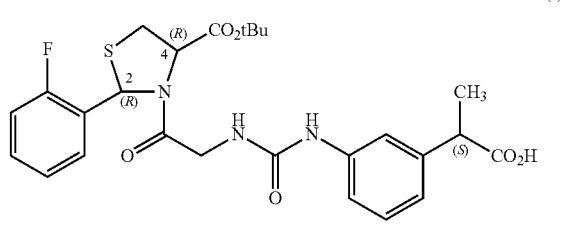

is useful in treating schizophrenia as well as reducing dopamine levels in the basal ganglia and specifically in ventral striatum and caudate nucleus in mammals. The compound of formula (I) is a potent CCK-B receptor antagonist and in human tests with the compound of formula (I), it was discovered that the amount of dopamine in the basal ganglia (ventral striatum and caudate nucleus) is effectively reduced in patients receiving the compound compared to levels before treatment. Unlike neuroleptics that block dopamine receptors and cause sever adverse effects, it was discovered that the compound of formula (I) reduces dopamine release by CCK-B receptor antagonism with a benign adverse effect profile.

The compound of formula (I) may be formulated for use in human and veterinary medicine for therapeutic use. The compound of formula (I) may be administered in its free form or in the form of a physiologically acceptable salts, such as, amine salts, such as dimethylamine or triethylamine salts, ammonium salt, tetrabutylammonium salt, cyclohexylamine salt, cicyclohexylamine salt, alkali metal salts, such as sodium or potassium salts, alkaline earth salts, and zinc salts (all of which are hereinafter referred to as a pharmaceutically acceptable salts). The compound of formula (I) may also be formulated in the pure state or in the form of a composition in which it is combined with any other pharmaceutically compatible product, which may be inert or physiologically active. Physiologically acceptable salts of the compound of formula (I) and its combinations with other compatible products are prepared by methods known in the art.

Administration may be by any suitable route including oral, rectal, nasal, topical (including buccal, and sublingual), vaginal and parenteral (including intrathecal, subcutaneous, intramuscular, intravenous and intradermal) with oral or parenteral being preferred. The preferred route may vary with, for example, the condition and age of the recipient.

While it is possible to administer the compound of formula (I) alone, it is preferable to present it as part of a pharmaceutical formulation. These pharmaceutical formulations may include the compound of formula (I) together with one or more acceptable carriers and optionally other therapeutic ingredients. The carrier(s) must be "acceptable" in the sense of being compatible with the other ingredients of the formulation and not deleterious to the recipient.

The formulations include those suitable for oral, rectal, nasal, topical (including buccal and sublingual), vaginal and parenteral (including intrathecal, subcutaneous, intramuscular, intravenous and intradermal) with oral or parenteral being preferred. The preferred route may vary with, for example, the condition and age of the recipient. The formulations may be presented in unit dosage form, e.g., tablets and sustained release capsule, and may be prepared by any methods well known in the art of pharmacy.

Such methods include the step of bringing into association the compound of formula (I) with the carrier which constitutes one or more accessory ingredients. For example, the formulations may be prepared by uniformly and intimately bringing into association the compound of formula (I) with liquid or finely divided solid carriers or both, and then if necessary shaping the products.

Formulations of the present invention suitable for oral administration may be presented as discrete units such as capsules, cachets, or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion and as a bolus.

As a solid formulation for oral administration, tablets, pills, powders (gelatin capsules, wafer capsules) or granules may be used. In these formulations, the compound of formula (I) is mixed with one or more inert diluents such as starch, cellulose, sucrose, lactose or silica, under a stream of argon or other inert gas. These compositions can also comprise substances other than diluents, for example one or more lubricants such as magnesium stearate or talc, a coloring, or coating (dragees) or a varnish.

In order to obtain unit dosages of oral preparations which are designed to prevent release and possibly decomposition of the active substance in the gastric juice, the tablets or capsules may be enteric-coated with a layer of a gastric juice-resistance enteric fluid or coating that is not dissolvable at the acidic pH of the gastric juice. Thus, the active substance will not be released until the preparation reaches the intestine. Such enteric coatings may include cellulose acetate, phthalate, hydroxypropylmethylcellulose and phthalates.

Sustained release tablets are obtained by using several layers of the compound of formula (I) separated by slowly dissolving coating layers. Another way of preparing sustained release tablets is to divide the dose of the compound of formula (I) into granulates with coatings of different thickness and compress the granules into tablets together with the acceptable carrier substances. The compound of formula (I) can also be incorporated in slowly dissolving tablets made from a variety of substances, such as, a fatty or waxy substance, or a physiologically inert plastic.

As a liquid formulation for oral administration, pharmaceutically acceptable solutions, suspensions, emulsions, syrups and elixirs may be used containing inert diluents such as water, ethanol, glycerol, vegetable oils or liquid paraffin. These formulations can comprise ingredients other than diluents, for example wetting, sweetening, thickening, flavoring or stabilizing products.

The sterile formulations for parenteral administration can preferably be solutions, aqueous or non-aqueous, suspensions or emulsions. As a solvent or vehicle, water, propylene glycol, a polyethylene glycol, vegetable oils, especially olive oil, injectable organic esters, for example ethyl oleate or other suitable organic solvents may be employed. Specifically, it has been shown that the compound of formula (I) is very soluble in ethanol and dimenthylformamide (solubility of 1000 mg/mL), freely soluble in methylene chloride (solubility of 500 mg/mL), ethyl acetate (solubility of 400 mg/mL), acetone (solubility of 250 mg/mL), diethyl ether (solubility of 100 mg/mL) and toluene (solubility of 100 mg/mL), sparingly soluble in sodium phosphate, pH 7.4 (solubility of 20 mg/mL) and very slightly soluble in water (solubility of 0.1 mg/mL). These formulations can also contain adjuvants, especially wetting, tonicity, emulsifying, dispersing and stabilizing agents. The sterilization may be carried out in several ways, for example, by aseptic formulation, by incorporation of a sterilizing agent in the composition, by irradiating or by heating. They may also be manufactured in the form of sterile solid formulations which can be dissolved at the time of use in sterile water or any other sterile injectable medium.

The formulations for rectal administration are suppositories or rectal capsules which contain, besides the active product, excipients such as cocoa, butter, semi-synthetic glycerides or polyethylene glycols.

The formulations for topical administration can be, for example, creams, lotions, patches, eyewashes, mouthwashes, nasal drops or aerosols. The patches bearing or otherwise containing the transdermal formulation are positioned on the body of a wearer in such manner as to remain in contact with the epidermis of the recipient for a prolonged period of time. Such patches comprise the active compound of formula (I) in an optionally buffered, aqueous solution, dissolved and/or dispersed in an adhesive, or dispersed in a polymer. A preferred formulation comprising the compound of formula (I) may be dispersed in a pressure sensitive adhesive which adheres to the skin, thereby permitting the compound to diffuse from the adhesive through the skin for delivery to the patient. Pressure adhesives known in the art such as natural rubber or silicone can be used.

The examples that follow illustrate exemplary medicament formulations or pharmaceutical composition embodiments.

Example 1

Powder-filled hard gelatin capsules containing 200 mg of the compound of formula (I) and having the following composition are manufactured according to techniques known in the art:

Compound of formula (I) . . . 200 mg
Microcrystaline cellulose, NF . . . 159.25 mg
Sodium Starch Glycolate, NF . . . 15 mg
Magnesium stearate, NF . . . 0.75 mg
Size "0" white/white opaque hard gelatin capsules, NF . . . 1 no.

Example 2

Hard gelatin capsules containing a 50 mg dose of the compound of formula (I) and having the following composition are manufactured according techniques known in the art:
Compound of formula (I) . . . 50 mg
Cellulose . . . 18 mg
Lactose . . . 55 mg
Colloidal silica . . . 1 mg
Sodium carboxymethylstarch . . . 10 mg
Talc . . . 10 mg
Magnesium stearate . . . 1 mg

Example 3

Tablets containing a 50 mg dose of active product and having the following composition are manufactured according to the techniques known in the art:
Compound of formula (I) . . . 50 mg
Lactose . . . 104 mg
Cellulose . . . 40 mg
Povidone . . . 10 mg
Sodium carboxymethylstarch . . . 22 mg
Talc . . . 10 mg
Magnesium stearate . . . 2 mg
Colloidal silica . . . 2 mg
Mixture of hydroxymethyl-cellulose, glycerol and titanium oxide (73:3.5:24.5) q.s. 1 finished film-coated tablet weighing 245 mg

Example 4

An injection containing 10 mg of active product and having the following composition may be manufactured according to the techniques known in the art:
Compound of formula (I) . . . 10 mg
Benzoic acid . . . 80 mg
Benzyl alcohol . . . 0.06 cm$^3$
Sodium benzoate . . . 80 mg
Ehanol, 95% . . . 0.4 cm$^3$
Sodium hydroxide . . . 24 mg
Prpylene glycol . . . 1.6 cm$^3$
Water . . . q.s. 4 cm$^3$ The dose at which the compound of formula (I) is administered may vary within a wide range and will depend on various factors, such as, for example, the severity of the condition, the age and weight of the patient and may have to be individually adjusted. In general for treating schizophrenia or reducing dopamine levels in ventral striatum and caudate nucleus, a suitable effective dose of the compound of formula (I), or its pharmaceutically acceptable salts, will be in the range of about 5.7 to 51.4 mg per kilogram recipient body weight per day, and preferably in the range of about 11.4 to 23 mg per kilogram body weight per day. The doses may be administered as unit dosage form. For example, in the clinical safety study described herein, patients with cocaine addiction cessation were administered three escalating doses of the compound of formula (I) orally twice daily at 200 mg, 400 mg and 800 mg. In schizophrenia severe cases it may be necessary to increase these doses by several folds.

A preferred dose is administered to achieve peak plasma concentrations of the compound of formula (I) or its physiologically acceptable salts of from about 200 ng/mL to about 1500 ng/mL, preferably from about 290 ng/mL to about 500 ng/mL and most preferably from about 315 ng/mL to about 470 ng/mL. This plasma concentration may be achieved by orally administering the compound of formula (I) in 200 mg, 400 mg or 800 mg unit dosages six times daily. Desirable blood levels may be maintained by continuous administration of the compound of formula (I) every 3.5 hours. The pharmaceutical compositions containing the compound of formula (I) may be formulated to provide doses within these ranges either as a single unit dosage or as a multiple unit dosage.

The administered ingredients may be used in therapy in conjunction with other medicaments such as neuroleptics, anti-depressants, antianxiety medications, or other medications that would alleviate or treat symptoms of schizophrenia.

U.S. Pat. No. 6,150,387 to Bohme et al. describes the use of substituted pyrrolidine compounds, such as the compound of formula (I), in preventing or reducing drug dependence, pharmacomania or substance abuse and as useful CCK and gastric receptor inhibitors for treating or preventing psychoses, anxiety disorders, Parkinson's disease, tardive dyskinesia, irritable bowl syndrome, acute pancreatitis, ulcers, disorders of intestinal motility and certain CCK-sensitive tumors and as useful appetite regulators and analgesics. The disorders listed above are caused by a decrease in dopaminergic activity. The entire content of the U.S. Pat. No. 6,150,387 is incorporated by reference herein.

A study entitled "Phase I, double-blind, placebo-controlled dose escalating assessment of potential interaction between cocaine and RPR 102681" ("the NIH study") investigated the effects of the RPR 102681 in treating cocaine abuse in humans, the entire content of which is incorporated by reference herein. This study concluded that the RPR 102681 is ineffective in treating cocaine abuse in humans. Based on the brain PET scan results of the participating subjects, the study also concluded that RPR 102681 does not increase the dopamine levels in the striatum of humans. Unexpectedly, these brain PET scan results revealed that the dopamine levels either remained the same or, at certain RPR 102681 plasma concentrations, were decreased in the ventral striatum and caudate nucleus of the study subjects.

The use of substituted pyrrolidine compounds as dipeptidyl peptidase IV inhibitors for use in improving fertility is described in PCT publication WO 0056296 (published Sep. 28, 2000), the entire content of which is incorporated by reference herein. The use of substituted pyrrolidine compounds for treating alcoholism and associated conditions is described in U.S. Pat. No. 5,935,980, the entire content of which is incorporated by reference herein. The compound of formula (I) and their salts may be prepared under the conditions described in International Application WO 93/01167, the entire content of which is incorporated by reference herein.

The safety profile of RPR 102681 was also examined in a study conducted at the National Institute on Drug Abuse, Protocol No. NIDA-CPU-RPR 102681-01, entitled "A Comparitive, Randomized, Two-Way Crossover, Food-Effect Bioavailability Study of RPR 102681 in Healthy Subjects," the entire content of which is incorporated by reference herein. This study concluded that in 12 healthy adult human subjects, most adverse events and treatment-associated adverse events that occurred during the study were mild or moderate except for one subject.

Materials and Methods

Phase I, Double-Blind, Placebo-Controlled Dose Escalating Assessment of Potential Interaction between Cocaine and RPR 102681 in Humans A dose escalation, double-blind, placebo-controlled inpatient study involved a randomized total of 16 volunteer experienced cocaine users, 18 to 45 years of age, who had used cocaine by the smoked or intravenous (i.v.) route in the past six weeks and provided a positive urine test for cocaine within two weeks prior to entering the study. Subjects were entered in a block randomization schedule such that for every two subjects who received the compound of formula (I) (RPR 102681), one subject received a matched placebo.

RPR 102681 capsules, 200 mg, and matching placebo capsules were manufactured by Murty Pharmaceuticals, Lexington, Ky. Both the active drug and placebo were packaged in size 0, white opaque hard gelatin capsules. Cocaine Hydrochloride solutions, 10 mg/mL in 2 mL ampoule (20 mg dose) and 20 mg/mL in 2 mL ampoule (40 mg dose), were manufactured by Murty Pharmaceuticals. Cocaine was administered by i.v. infusion over 60 seconds by the study physician.

The following inclusion and exclusion criteria were used in selecting the subjects for the study:

Inclusion Criteria:

In order to have participated in the study, subjects must have met the following criteria:
1. Volunteers who were not seeking treatment at the time of the study.
2. Between 18 and 45 years of age and within 20% of ideal body weight according to the Metropolitan Height and Weight Chart, and weigh at least 45 kg.
3. Met DSM-IV criteria for cocaine abuse or dependence.
4. Were currently using cocaine by the smoked or intravenous (i.v.) route, with use confirmed by a positive BE urine test once within 30 days prior to entering the study.
5. Been able to verbalize understanding of consent form, able to provide written informed consent, and verbalize willingness to complete study procedures.
6. If female, had a negative pregnancy test within 72 hours prior to receiving the first dose of investigational agent and agreed to use one of the following methods of birth control, or be postmenopausal, or have had hysterectomy, or have been sterilized, or be male.
    a) complete abstinence from sexual intercourse
    b) diaphragm and condom by partner
    c) intrauterine device and condom by partner
    d) sponge and condom by partner
Note: oral contraceptives, Depo-Provera, Norplant and intrauterine progesterone contraceptive system were not allowed.
7. Had a history and physical examination that demonstrate no clinically significant contraindication for participating in the study.
8. Been able to comply with protocol requirements, Clinical Pharmacology Unit (CPU) rules and regulations, and be likely to complete all the study treatments.

Exclusion Criteria:

In order to have participated in the study, subjects must have not met the following criteria:
1. A current or past history of seizure disorder, including alcohol- or stimulant-related seizure, febrile seizure, or significant family history of idiopathic seizure disorder.
2. Any previous medically adverse reaction to cocaine, including loss of consciousness, chest pain, or seizure.
3. According to DSM-IV criteria as determined by structured clinical interview (SCID), had any history of major psychiatric illness, such as bipolar disorder, depression, manic or dysthymic illness, other than drug dependence or disorders secondary to drug use as determined by a National Institute of Mental Health trained technician.
4. Pregnant or lactating.
5. A history of liver disease or current elevation of aspartate aminotransferase (AST) or alanine aminotransferase (ALT) exceeding the upper limit of normal.
6. Donated a unit of blood or participated in any other clinical investigation within 4 weeks of enrolling on the study.
7. A history of any illness, or a family history of early significant cardiovascular disease, or a history of behavior, that in the opinion of the investigator might confound the results of the study or pose additional risk in administering the investigational agents to the subject.
8. Seropositive for hepatitis B surface antigen, hepatitis C antibody, or human immunodeficiency virus (HIV) type 1.
9. A diagnosis of adult onset asthma (i.e., 21 years or older), or chronic obstructive pulmonary disease (COPD), including those with a history of acute asthma within the past two years, and those with current or recent (past 2 years) treatment with inhaled or oral beta-agonist.
10. Any illness, condition, and use of medications, that in the opinion of the principal investigator and the admitting physician, would preclude safe and/or successful completion of the study.
11. Currently use illicit drugs besides cocaine and marijuana.
12. Had used any prescription drugs within 14 days of the start of the study or non-prescription drugs within 7 days of the start of the study.
13. Unable to distinguish between a 20 mg and 40 mg dose of cocaine intravenously during the administration of screening infusions.
14. Had prior exposure to radiation for a research study. This excludes having x-rays for medical purposes.
15. Had tattoos within the last 6 months.
16. Had any metallic body art (such as eye rings, navel rings) that cannot be removed.
17. Had an abnormal MRI finding discovered as part of the PET Scan procedure.

Screening

Subjects had up to 30 days for screening. Screening of subjects to establish eligibility occurred initially before clinic intake and was completed after intake. Assessments performed before intake include collection of demographic information and completion of a subject locator form, a timeline follow back interview for cocaine use for the past 30 days, medical history, a 12-lead ECG, and physical examination including vital signs (HR and BP). Blood was collected for complete blood count, chemistries, including liver function tests, infectious disease panel, including human immunodeficiency virus (HIV) type 1, pregnancy and alcohol assessments. Urine was collected for routine urinalysis. A urine drug toxicology screen was also conducted for drugs of abuse; it was repeated until a negative test for cocaine was obtained. With the exception of cocaine, cocaine metabolites, and marijuana, the urine drug toxicology screen must have been negative to enroll in the study. Candidates deemed eligible based on the screening assessments mentioned above were administered a structured clinical interview (SCID) by a trained mental health professional to determine if there were any underlining psychiatric conditions that might have excluded potential subjects from participation. These assessments were completed within 30 days before clinic intake.

Subjects were instructed that no prescription or non-prescription medications were allowed to be taken within 14 and 7 days of the start of the study, respectively. Subjects were instructed to refrain from using any alcohol from 48 hours before clinic intake until discharge from the study. Subjects were also instructed to refrain from participation in contact sports and weight lifting from 48 hours before the inpatient period until the completion of the study. Potential candidates whose screening assessment results did not exclude them from study participation completed intake procedures and resided full-time as inpatients until discharge or completion of the study.

The first seven inpatient days (Days −7 through −1) were allotted for the subjects' urine to become negative for cocaine. Day 0 and day 1 were the days of inpatient screening before first cocaine infusion and included a brief physical exam, vital signs, 12-lead ECG, serum prolactin, urine drug toxicology screen, a β-HCG (pregnancy test), a blood chemistry, a breathalyzer test, and Brief Substance Craving Scale (BSCS), Brief Psychiatric Rating Scale (BPRS), Profile of Mood States (POMS), Visual Analogue Scale (VAS), Addiction Research Center Inventory (ARCI), and Adjective Scale assessments.

As listed in FIG. 1, cocaine infusions of 20 mg and 40 mg i.v. were administered on days 2 and 3. After establishing eligibility including cardiovascular responses to screening cocaine infusions of 20 mg and 40 mg i.v. (days 2 and 3) subjects were randomized to receive either RPR 102681 or matched placebo. Three days after the second screening infusion and with urine assay negative for cocaine, all subjects received baseline cocaine infusions of 20 mg and 40 mg i.v. on two consecutive days (days 7 and 8) and started treatment the next day (day 9) with 200 mg of RPR 102681 twice daily (b.i.d.) or matched placebo b.i.d. for seven (7) days. After beginning of daily treatment with either RPR 102681 or placebo, subjects received treatment cocaine infusions of 20 mg and 40 mg i.v. on two consecutive days (days 14 and 15). After seven (7) days of treatment with the lowest dose of RPR 102681 (200 mg b.i.d.), the dosing escalated to the next higher dose sequentially, 400 mg b.i.d and then 800 mg b.i.d. Subjects received 7 days at each dose of RPR 102681 with no washout between dosage levels and cocaine infusions of 20 mg and 40 mg i.v. on the last two days of each dosage level. Each cocaine infusion was preceded or followed by saline i.v. infusion in random order; cocaine and saline infusions was administered 60 minutes apart.

Therefore, as shown in FIG. 1, all subjects received cocaine infusions on ten days: days 2, 3, 7, 8, 14, 15, 21, 22, 28, and 29. Subjects received 20 mg cocaine i.v. on days 2, 7, 14, 21, and 28 and 40 mg cocaine i.v. on days 3, 8, 15, 22, and 29. A study physician administered each i.v. infusion dose over 1 minute duration. For each infusion session (screening, baseline and treatment), subjects were randomly assigned (1:1 ratio) to receive either saline at 8:00 A.M. followed by cocaine one hour later at 9:00 A.M. or cocaine at 8:00 A.M. followed by saline in a double-blind fashion (subjects and research staff were blinded) one hour later at 9:00 A.M. During the treatment infusions (sessions #5-10), the subjects took the morning dose of RPR 102681 at 6:05 A.M., and received the infusions at 8:00 A.M. and 9:00 A.M.

Primary Outcome Measures

Primary outcome measures included heart rate (HR) and Blood Pressure (BP). HR and BP measures during saline infusions were compared to HR and BP after each cocaine infusion (20 mg and 40 mg doses). Changes in HR and BP induced by cocaine infusion along with RPR 102681 were compared to those without RPR 102681, by cocaine dose level (20 mg and 40 mg doses), using repeated measures analysis of variance (ANOVA).

Changes in ECG readings during saline infusion as compared to those taken during cocaine infusions were also reported.

Secondary Outcome Measures

Secondary outcome measures included pharmacokinetic (PK) parameters, psychological assessments, and serum prolactin and DA release in striatum. PK interactions between cocaine and RPR 102681 were assessed by collecting blood and determining levels of cocaine and benzoylecgonine (BE), peak and trough levels of RPR 102681 during cocaine treatment infusions, for sessions #6, 8, and 10 as shown in FIG. 1. Serum prolactin levels were assessed to determine the effect of RPR 102681. At each RPR 102681 dosage level, DA release in striatum was estimated using PET scan with [$^{11}$C]-raclopride and compared to baseline DA release.

Pharmacokinetics Parameters

Plasma concentration-time profiles of cocaine after baseline cocaine infusion, FIG. 1, session #4, were analyzed to obtain PK parameter estimates of cocaine ($T_{max}$, $C_{max}$, $AUC_{0-24}$, apparent $t_{1/2}$, CL/F, $V_d$/F, and $k_e$) by individual. The means computed (between subjects comparison) were compared with data from the post-treatment cocaine infusions for each RPR 102681 dose level being averaged by subject. The RPR 102681 levels were analyzed for different sessions shown in FIG. 1. The RPR 102681 levels were analyzed for 200 mg RPR 102681 b.i.d level for sessions #5 and #6, for 400 mg RPR 102681 b.i.d level for sessions #7 and #8 and for 800 mg RPR 102681 b.i.d level for sessions #9 and #10. Blood for cocaine/BE PK determinations was collected at the following time points: 20 minutes prior to and 5, 15, 30, 59, 65, 75, 90, 120, 180, 240 and 300 minutes post infusion, for sessions #4, 6, 8, 10.

PK parameters determined for treatment infusions, for sessions #6, 8 and 10, were compared between RPR 102681 dose levels by t-tests. Confidence intervals (90%) for each parameter were determined. To be certain that there were no inherent differences between the pharmacokinetics of cocaine and the RPR 102681 cohort and cocaine and placebo cohort, PK parameters between these two cohorts were also compared during the baseline 40 mg i.v. cocaine infusion, session #4.

Blood for RPR 102681 PK determinations was collected at 95 and 205 minutes after the morning dose on days 13, 14, 15, 20, 21, 22, 27, 28 and 29. Pharmacokinetics (peak and trough levels) of RPR 102681 during treatment at a dose of 200 mg (day 13), 400 mg (day 20) and 800 mg (day 27) b.i.d. were determined. These data were compared to PK of RPR 102681 obtained during the treatment with cocaine infusions for each dose level by t-tests, i.e. sessions #5 & 6 for 200 mg b.i.d., sessions #7 & 8 for 400 mg b.i.d, and sessions #9 & 10 for 800 mg b.i.d.

The plasma concentration of RPR 102681 was determined with a validated liquid chromatography assay with mass spectrometric detection (LC/MS/MS) at the Department of Biopharmaceutical Sciences, University of California, San Francisco, Calif.

The sample plasma specimens for determining plasma concentration (354 RPR 102681 plasma specimens and 109 Prolactin plasma specimens) were frozen and packed in dry ice upon receipt by the Analytical Division/Drug Studies Unit at South San Francisco, Calif. These samples were kept frozen at approximately −20° C. until analyzed.

Human plasma samples (0.100 mL) were analyzed for RPR 102681 with an LC/MS/MS procedure utilizing a PE Sciex III system equipped with a BDS Hypersil C18 column (4.6×15 mm, 5 μm particle size), a mobile system consisting of acetonitrile:water:trifluoroacetic acid (70:30:0.06) (v/v) with 0.0006% (w/v) ammonium phosphate dibasic; mass spectrometric detection was accomplished with a sample inlet, heated nebulizer, positive ionization by Atmospheric Pressure Chemical Ionization (APCI) and mass scanning by Multiple Reaction Monitoring (MRM) analysis. Sample preparation consisted of precipitation of 0.100 mL of plasma with acetonitrile containing the internal standard (prednisolone acetate) prior to separation by LC/MS/MS. The linear range of the assay was 1.0 to 160 ng/mL, with a lower limit of quantitation of 1.0 ng/mL.

Standard curve and quality control (QC) samples were generated by spiking interference free human plasma samples with known amounts of RPR 102681 and internal standard (IS). These standard curve, assay, and QC samples were processed, then 40 μl aliquots were injected into the LC/MS/MS system for chromatographic separation and subsequent mass spectrometric detection. The peak area ratios of RPR 102681 to IS were calculated for each sample from the measured peak areas obtained by LC/MS/MS. Finally, spiked concentrations and RPR 102681 to IS peak area ratios of the standard curve samples were fit by 1/× weighted least squares linear regression to the equation for the best straight line (y=mx+b, where y=peak area ratio and x=RPR 102681 concentration), and drug concentration in assay sample were calculated by the equation from the RPR 102681 to IS peak area ratios obtained by LC/MS/MS.

Cocaine plasma concentration-time profiles were analyzed by non-compartmental analysis (NCA) (Gibaldi M, Perrier D, "*Pharmacokinetics*" $2^{nd}$ ed. New York: Marcel Dekker, 1982) using the program WinNonlin version 4.1 (WinNonlin, User's Guide, Pharsight Corporation, Mountain View, Calif., 1999). Zero time was defined as the start of the one minute intravenous infusion. Plasma concentrations less than the lower limit of quantitation measured before drug administration were set equal to zero. Plasma concentrations less than the lower limit of quantitation after drug administration were treated as missing data points. The WinNonlin module employed was that for constant-rate intravenous infusion. Maximum plasma concentration ($C_{max}$) and time of maximum plasma concentration ($T_{max}$) were obtained from the WinNonlin computer algorithm, which gives values equivalent to that obtained by visual inspection. Area under the plasma concentration-time curve from 0 time to the last measurable data point ($AUC_{last}$) was measured using the linear trapezoidal rule up to $C_{max}$, and then by the logarithmic trapezoidal rule (Chiou W L, "*Critical evaluation of the potential error in pharmacokinetic studies of using the linear trapezoidal rule method for the calculation of the area under the plasma level-time curve*," J Pharmacokin Biopharm 6:539-546, 1978).

The cocaine terminal exponential rate constant (λz) was estimated by linear, least-squares regression analysis of the terminal exponential phase data-points of the logarithmically transformed cocaine plasma concentrations of the profiles (based on visual inspection of the data λz was calculated using all data points (inclusive) from the nominal 1.0 hour point onwards (or, if there did not exist a 1 hour time-point, the first time-point thereafter). Terminal exponential half-life ($T_{1/2}$) was calculated as ln(2)/λz. Area under the plasma concentration-time curve from the last measurable data point to infinity ("extrapolated area" or $AUC_{(ext)}$) was determined by dividing the last measurable plasma concentration by λz. Area under the plasma concentration-time profile from 0 time to infinity ($AUC_{inf}$) was obtained by summing area to the last measurable data point ($AUC_{last}$) with the extrapolated area ($AUC_{(ext)}$). The extrapolated area as a percent of $AUC_{inf}$ was termed $AUC_{\%\ ext}$. AUC from 0 to 4 hours (available for both cocaine and BE in all datasets, denoted $AUC_{(0-4\ h)}$), was calculated by the WinNonlin interpolation routine.

Mean residence time (MRT) was calculated from the relationship: MRT=[$AUMC_{(0-inf)}$]/[$AUC_{(0-inf)}$], where $AUMC_{(0-inf)}$ is the area under the first statistical moment curve from time 0 to infinity (using the same linear/logarithmic trapezoidal method employed for AUC). Clearance (CL) was determined as dose divided by $AUC_{(0-inf)}$. $V_{ss}$ was calculated from the relationship: $V_{ss}$=(MRT)*(CL). $V_z$ was calculated from the relationship: $V_z$=CL/λz.

BE plasma concentrations were analyzed in the same manner as with the cocaine data, with the following exceptions: (1) the WinNonlin module utilized was for "extravascular administration;" (2) the terminal exponential phase rate constant (λz) and $T_{1/2}$ values were not determined, since terminal exponential data would have occurred subsequent to 4-5 hours, viz., beyond the scope of the data set; and (3) MRT, $V_{ss}$, $V_z$ and CL were not calculable (insufficient data/information).

Prolactin Study

Blood for prolactin level determinations were collected on day 0 at 6:00 A.M. before breakfast (7:00 A.M.) and also three times a day on days 15, 22 and 29 with first blood draw performed at 6:00 A.M. before the morning dose of RPR 102681 (6:05 A.M.) and the other two at 30 minutes after each i.v. infusion. Prolactin levels on days 15, 22, and 29 were compared between RPR 102681 and placebo cohorts to determine the extent to which prolactin levels are modified by the administration of RPR 102681 using repeated measures ANOVA. Changes in prolactin level induced by 40 mg cocaine infusion along with RPR 102681 (days 15, 22 and 29) were compared for each subject by RPR 102681 dose level using repeated measures ANOVA.

Prolactin concentrations were determined using a commercially available radioimmunoassay (Coat-A-Count® Prolactin IRMA, Diagnostic Products Corporation, Los Angeles, Calif.). Calibrator and QCs (CON6, lots #019 and 020) were also supplied by the manufacturer. Fifty microliters of calibrators, QCs and study samples were added to prolactin polyclonal antibody-coated tubes. This was followed by 200 μL of $^{125}$I-labeled prolactin monoclonal antibodies, followed by shaking for 2 hours. The tubes were decanted and drained; 2 mLs of buffered wash solution was added for 1-2 minutes; the tubes were again decanted and drained; this was followed by a second wash step. After thorough draining, the radioactivity in the tubes was determined from 1 minute counts using a Packard Cobra II gamma counter (Downers Grove, Ill.). In theory, the $^{125}$I-labeled prolactin monoclonal antibodies bind only to prolactin bound to the antibody coated onto the tubes. The radioactivity retained in the tube increases as does the amount of prolactin in the samples. The software for the gamma counter generates a standard curve based on the log of the concentration and the log of the B/Bo for the calibrators. This curve is used to back-calculate the concentration of prolactin in the samples. The calibrators have lot-specific concentrations; for those used in these analyses, they were 2.35, 4.90, 9.90, 19.4, 50.0 and 101 ng/mL. The QCs also have lot specific target concentrations. For the first lot they were 8.6, 17.3 and 60 ng/mL; for the second lot they were 8.4, 16.4 and 56 ng/mL. Calibrators and study samples were run in duplicate. For study samples the following rule was used to determine the reported concentration: if the 2 replicates were within 15% the result of the first was used; if the 2 replicates were within >15 to 30%, the average of the two was used; results for the 2 replicates with >30% difference resulted in repeat analysis of a single replicate that was compared to the initial two to see if any 2 first agreed by 15% (use first) or if not by 30% (use average).

Imaging Study

The Positron Emission Tomography (PET) scans were performed at the PET Center of Johns Hopkins University at Johns Hopkins Hospital, Baltimore, Md. During the PET scans three plasma samples of RPR 102681 were obtained from each subject under different dosing to measure RPR 102681 plasma concentration.

Each subject was also studied using Magnetic Resonance Imaging (MRI). Each subject received an individual thermoplastic mask molded to their face to allow for repositioning and stabilizing of the head during the MRI procedure and PET scan later. Marks, which localized the anatomical structures of interest, were placed on the mask following the MRI scan. In particular, each subject received an MRI with a sagittal scout view to localize the anterior commissure-posterior commissure (AC-PC) line to allow standardized positioning across the subjects based on the anatomical landmarks. Subjects then underwent a standard spoiled grass sequence (SPGR) imaging for a three-dimensional anatomical data set of the brain, which was used to check the presence of abnormalities, e.g. brain tumors and other space-occupying or parenchymal lesions that would exclude the subjects from the study, and to identify structures relevant to this study, including caudate, putamen and cerebellar cortex.

Participants received orally twice daily 200, 400, and 800 mg of RPR or matched placebo on days 9-15, 16-22, and 23-29, respectively; 20 and 40 mg iv cocaine infusions on days 2, 7, 14, 21, 28 and 3, 8, 15, 22, 29, respectively, under two different schedules: 1) Dosing Schedule A: bid at 6:00 am and 5:00 pm; 2) Dosing Schedule B: bid at 6:00 am and 5:00 pm, except on days of PET scans the second dose was administered one or one and half hours before the start of the PET scan instead of at 5:00 PM.

[$^{11}$C]-raclopride PET scans were preformed on days 6, 13, 20 and 27. Dynamic images were reconstructed using filtered back projection with a ramp filter, resulting in a spatial resolution of ~4.5 mm full width at half maximum (FWHM). To measure the specific binding of tracer, binding potential (BP) images were generated by a simplified reference model with a linear regression algorithm (*Using a reference tissue model with spatial constraint to quantify [$^{11}$C] Pittsburgh compound B PET for early diagnosis of Alzheimer's disease*, Yun Zhou, Susan M. Resnick, Weiguo Ye, Hong Fan, Daniel P. Holt, William E. Klunk, Chester A. Mathis, Robert Dannals, and Dean F. Wonga, NeuroImage 36 (2007) 298-312).

In pharmacokinetics and receptor-ligand kinetics the BP is a combined measure of the density of available neuroreceptors and the affinity of a drug to that neuroreceptor. Three regions of interest, the caudate nucleus (CN), the putamen (Pu), and the ventral striatum (VS), were defined on the co-registered MRI images. Intrasynaptic dopamine concentration (ISDAC) changes in the striatum are estimated by the difference in BP by using the following mathematical formula:

$$BP_{df} = BP(\text{RPR}) - BP(\text{baseline})$$

Subjects received PET scans with [$^{11}$C]-raclopride at baseline after uneventful completion of screening cocaine infusions and assignment to RPR 102681 or placebo treatment and on the fifth day of each RPR 102681 dose level (days 13, 20 and 27). After six subjects had completed all four PET scans these subjects' PET scan data was analyzed without breaking the blind to determine whether or not the PET scans should have been administered to any additional subjects. If there were no significant drug treatment effects evidenced by changes in the PET scans of these 6 subjects, the PET scans were not done on the remaining subjects; if the PET scan findings were not definitive, the PET scans were administered to the remaining subjects who consented to the PET scan procedures. The subjects were discharged 5 days after the last infusion of cocaine (day 35). Subjects were requested to return for follow-up at 1 month after the day of discharge.

Dopamine (DA) release in striatum measured by PET scans with [$^{11}$C]-raclopride ($B_{max}$, $K_d$ and BP values) were compared between RPR 102681 and placebo cohorts to determine the extent to which administration of RPR 102681 modulates dopamine neurotransmission using repeated measures ANOVA. RPR 102681-induced changes in DA release in striatum were also compared for each subject by dose level to identify an effective dose of RPR 102681 for prospective Phase 2 clinical trials using repeated measures ANOVA.

Results

Phase I, Double-Blind, Placebo-Controlled Dose Escalating Assessment of Potential Interaction between Cocaine and RPR 102681 in Humans Primary Outcome Measures FIG. 2 shows the pre-infusion average and post-infusion maximum for Heart Rate/Systolic Blood Pressure/Diastolic Blood Pressure (HR/SBP/DBP) by treatment group and study day. All vital signs increased after cocaine infusion and greater responses were observed for higher cocaine dose. There was no statistical difference between RPR 102681 and placebo groups prior to infusions, post saline or post cocaine infusions on any day for all three measures. As expected, cocaine at both doses induced significant elevation in HR/SBP/DBP (most P-values<0.05) and its effect was more notable in the RPR 102681 group.

FIG. 3 shows data from the RPR 102681 group; the P-values of pair-wise comparisons for the various RPR 102681 and cocaine conditions, in terms of maximum HR/SBP/DBP changes. Column variables include maximum post cocaine/maximum post saline values. In general, RPR 102681 does not significantly change HR/SBP/DBP with a few exceptions. It appears that RPR 800 mg reduces the elevation of HR after cocaine 40 mg (P-value=0.009) and DBP after cocaine 20 mg (P-value=0.093), but RPR 102681 at 200 mg increased the elevation of SBP after cocaine 20 mg (P-value=0.031).

FIGS. 4A-4F graphically show the average difference between maximum post-cocaine values and maximum post-saline values (-●-●-=RPR; --○--○--=Placebo). After adjusting for baseline (day 7 for 20 mg or day 8 for 40 mg), the GEE model shows that RPR 102681 effect is significant for only SBP at cocaine 20 mg (P-value=0.0412). Compared to the placebo group, the RPR 102681 group experienced significantly greater SBP increase in response to cocaine 20 mg. Furthermore, there is a decreasing trend with higher RPR 102681 doses for HR/SBP after cocaine 40 mg in the RPR 102681 group and DBP after cocaine 20 mg.

FIG. 5 shows ECG statistics on the non-infusion days by group. A 12 Lead ECG was scheduled at Pre-Intake Screening, Intake Screening, Discharge and follow-up all of which are non-infusion days. On infusion days (2, 3, 7, 8, 14, 15, 21, 22, 28 and 29) five 12 Lead ECG's were scheduled at −10, 4, 40, 64 and 100 minutes in relation to the infusion. All subjects completed the non-infusion ECG's at baseline and discharge. The missing ECGs (non-infusion and infusion) were not performed because subjects either discontinued the trial or did not return for follow-up visits. As shown in FIG. 5, the mean values for VR, PR, QT, RR and QRS are within normal range for each domain.

FIG. 6A illustrates a comparison between intake screening (days−7 to 1) and each of the pre infusion measurements on days 8, 15, 22, and 29 when cocaine 40 mg was administered. A nonparametric Signed Rank Test shows that for subjects in the RPR 102681 group, pre infusion PR durations are significantly longer than PR duration at intake screening. There is no significant difference in PR duration between intake screening and pre infusion value for the placebo group. No significant difference is observed between intake screening and pre infusion measurements in RR and QT duration for either group.

To evaluate subjects' responses to cocaine infusion, measurements after cocaine 40 mg infusion were compared to those prior to any infusion (reading at −10 min). Readings at 4 min and 40 min were used when the first infusion was cocaine while readings at 64 min and 100 min were used when the second infusion was cocaine. The nonparametric Signed Rank Test was used to evaluate change from pre infusion baseline to measurements obtained post cocaine infusion, as shown in FIGS. 6B, 6C and 6D. In the RPR 102681 group, PR duration following cocaine infusion is significantly lower than that prior to infusion except on day 8 at 4 min post cocaine infusion. Both RR and QT duration at 4 min post cocaine infusion are significantly lower compared to their pre infusion baseline in the RPR 102681 group. The RPR 102681 group also had decreased RR and QT duration from baseline at 40 min post cocaine infusion on day 15. In the placebo group, some scattered significant decreases from baseline were observed including PR duration at 4 min post cocaine on day 8 and RR duration at 4 min post cocaine on day 8 and 15. In summary, PR/RR/QT duration in the RPR 102681 group seemed to decrease following cocaine 40 mg infusion. However, the statistical significance might not hold if multiplicity adjustment was performed in these multiple comparisons. In fact, the changes were all within normal ranges and were not clinically significant.

Secondary Outcome Measures

Pharmacokinetics Parameters

As shown in FIG. 7, no significant differences between the placebo and the RPR 102681 groups at baseline infusion were found for all the cocaine and BE pharmacokinetic parameters examined. The two cohorts are compatible with respect to their cocaine pharmacokinetics.

FIGS. 8 and 9 illustrate the results of the comparisons between the pharmacokinetic parameters at the post-treatment RPR 102681 doses and their baseline values (within group comparisons) for cocaine and BE, respectively. The estimates of bioavailability, relative to baseline, and the associated 90% confidence intervals are also displayed.

No statistically significant differences from baseline were detected for all cocaine and BE parameters. The ratios of post-treatment PK parameters relative to baseline were close to 100% and their 90% confidence intervals are within acceptable range for all the parameters except for cocaine $C_{max}$. The ratios relative to baseline for cocaine $C_{max}$ at 200 mg and 400 mg of RPR 102681 are near 100%, but with the 90% confidence intervals wider than acceptable range due to the larger variability for $C_{max}$ At 800 mg of RPR 102681, the relative ratio is on the high side (117.8%) and with a very wide confidence interval. This is because of the extremely large $C_{max}$ value observed for subject #58. The ratio became closer to 100% when the analysis was performed on the log-transformed $C_{max}$ (105.1%), as the log transformation tends to minimize the influence of a extremely large value. Though the cocaine $C_{max}$ data prove neither the presence nor the absence of interaction between RPR 102681 and cocaine kinetics due to the larger variability observed, especially when an outlier is present, the overall PK results do not suggest a possibility of interaction.

PET scans were performed on days 13, 20 and 27 and additional plasma samples were also taken at the time of the scan in order to determine if the changes of DA release in striatum (assessed with PET scan) after treatment with RPR 102681 were correlated with RPR 102681 plasma levels. In the original protocol, the PET scan was to be performed at approximately 8-11 hours (close to trough plasma concentrations) after RPR102681 dosing. The protocol was later amended and the time for PET scan was changed to approximately 2-3.5 hours (close to peak plasma concentrations) after dosing. Seven subjects received a PET scan at 8-11 hours after dosing and 4 subjects at 2-3.5 hours after dosing.

FIG. 10 shows the plasma RPR 102681 concentrations for individual subjects and the summary statistics for the plasma concentrations at 2-3.5 hours and at 8-11 hours post treatment. FIGS. 11A-11B present the plasma concentration-time profiles for all subjects by day in linear and semilogarithmic scales (◇=0007, □=0008, △=0011, x=0012, *=0014, ○=0036, +=0052, ▲=0058, ■=0073, ◆=0076, ●=0088). The mean plasma concentrations at 2-3.5 hours were approximately 19, 15 and 8 times of those at 8-11 hours for the 200 mg, 400 mg and 800 mg doses respectively.

FIGS. 12A-12D show the RPR 102681 concentration-time plots for all subjects at 95 minutes and 215 minutes after RPR 102681 dose on linear and semilogarithmic scales (◆=0001, ■=0007, ●=0008, ◆=0011, *=0012, —=0014, +=0036, –=0052, ○=0058, ◇=0073, △=0076, □=0088). Concentration was set to 0 if the concentration was less than 1.00 ng/mL. Summary statistics for RPR 102681 concentrations at 95 and 215 minutes, and an average of 3 days after RPR 102681 dose are presented in FIGS. 13 and 14.

The 3-day average plasma concentrations of RPR 102681 at 200 mg, 400 mg and 800 mg doses for all 12 individual subjects in the treatment group and the summary statistics for the group are presented in FIG. 14. The means of the 3-day average concentrations at each dose level are displayed in FIG. 16.

As illustrated in FIG. 14, at 95 minutes post dose the increase in mean blood level of RPR 102681 was slightly less than proportional as dose increases from 200 mg to 400 mg (concentration increases from 242.11 to 421.78 ng/mL). As the dose increases from 400 mg to 800 mg, the mean blood level of RPR 102681 did not increase much at all (mean concentration is 440.64 ng/mL for 800 mg). A similar pattern was observed for the concentrations at 215 minutes post dose (mean concentrations are 140.28, 255.08 and 285.28 ng/mL for 200, 400 and 800 mg respectively).

Figure 15:
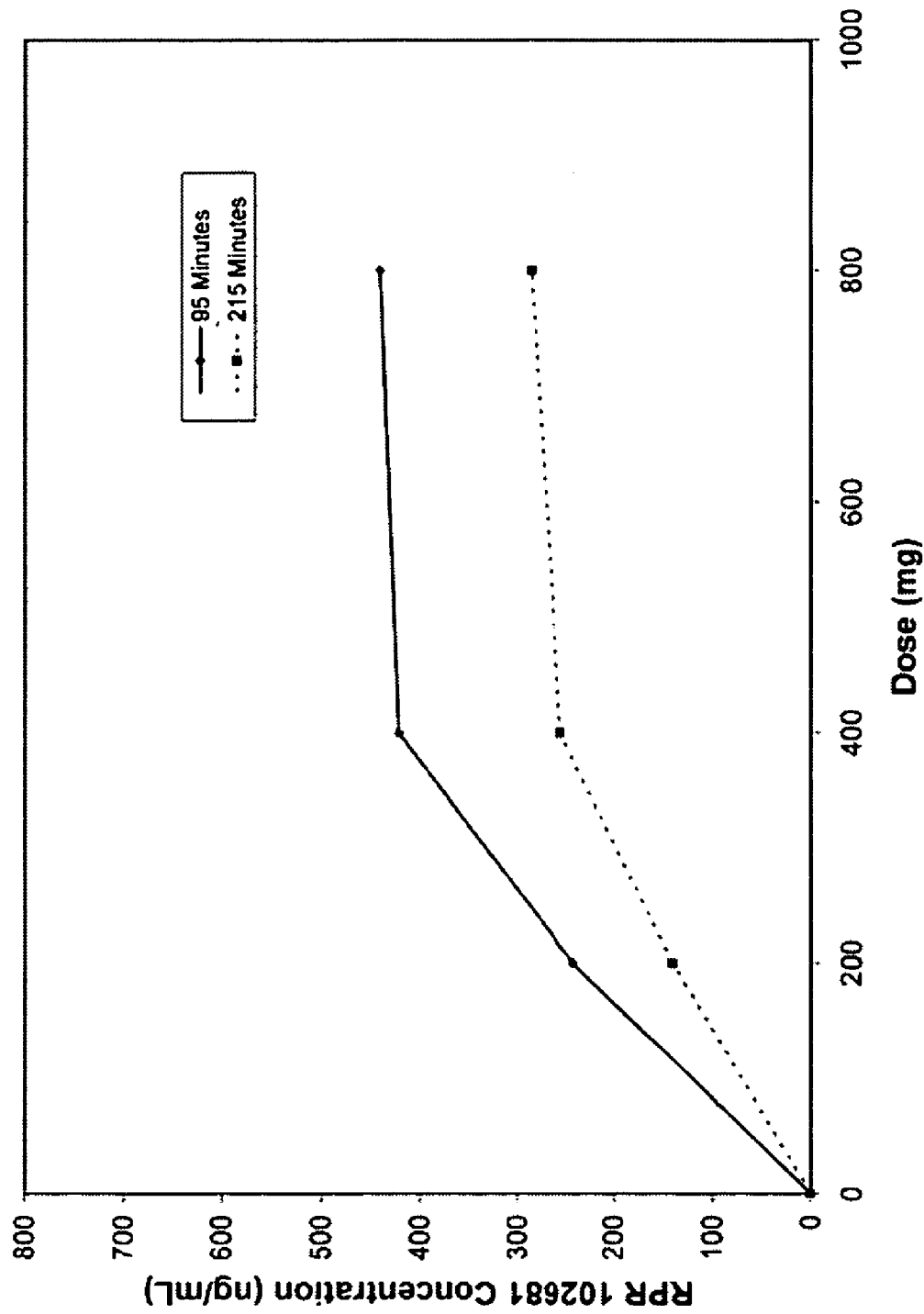
FIG. 15 is a graphical depiction of mean plasma concentrations of RPR 102681 at each dose level for the RPR 102681 group.

FIG. 15 graphically shows the apparent non-linearity of RPR 102681 pharmacokinetics (viz., mean plasma concentration) (●=95 minutes, ■=215 minutes). When PK is dose proportional, the concentration versus dose curve should be a straight line through the origin. Severe deviation from dose-proportionality was observed from 400 mg to 800 mg dose range, and the same pattern was observed for both 95 minutes and 215 minutes post-dose concentrations.

RPR 102681 dose-proportionality was assessed and the results are shown in FIG. 16. As shown in FIG. 16, significant differences in dose-normalized concentrations were found between 200 mg versus 800 mg and 400 mg versus 800 mg for both 95-minute and 215-minute concentrations. The estimated least-squares means of dose-normalized RPR 102681 concentrations at 95 minutes post-dose on each day were as follows: 1.26, 1.12 and 1.25 ng/mL for days 13, 14 and 15 (200 mg), 1.36, 0.87 and 1.05 ng/mL for days 20, 21 and 22 (400 mg), and 0.78, 0.58 and 0.43 ng/mL for days 27, 28 and 29 (800 m). At 215 minutes after dose, the estimated least-squares means were: 0.70, 0.78 and 0.62 ng/mL for days 13, 14 and 15 (200 mg), 0.58, 0.54 and 0.66 ng/mL for days 20, 21 and 22 (400 mg), and 0.42, 0.39 and 0.33 ng/mL for days 27, 28 and 29 (800 mg). Though it appears that at 800 mg there was a decreasing trend with day for the 95-minute concentrations, the trend cannot be confirmed by statistical test. No statistical significant day effect or dose-by-day interaction was found. Therefore, the final analysis included only the dose effect in the model.

Figure 17:
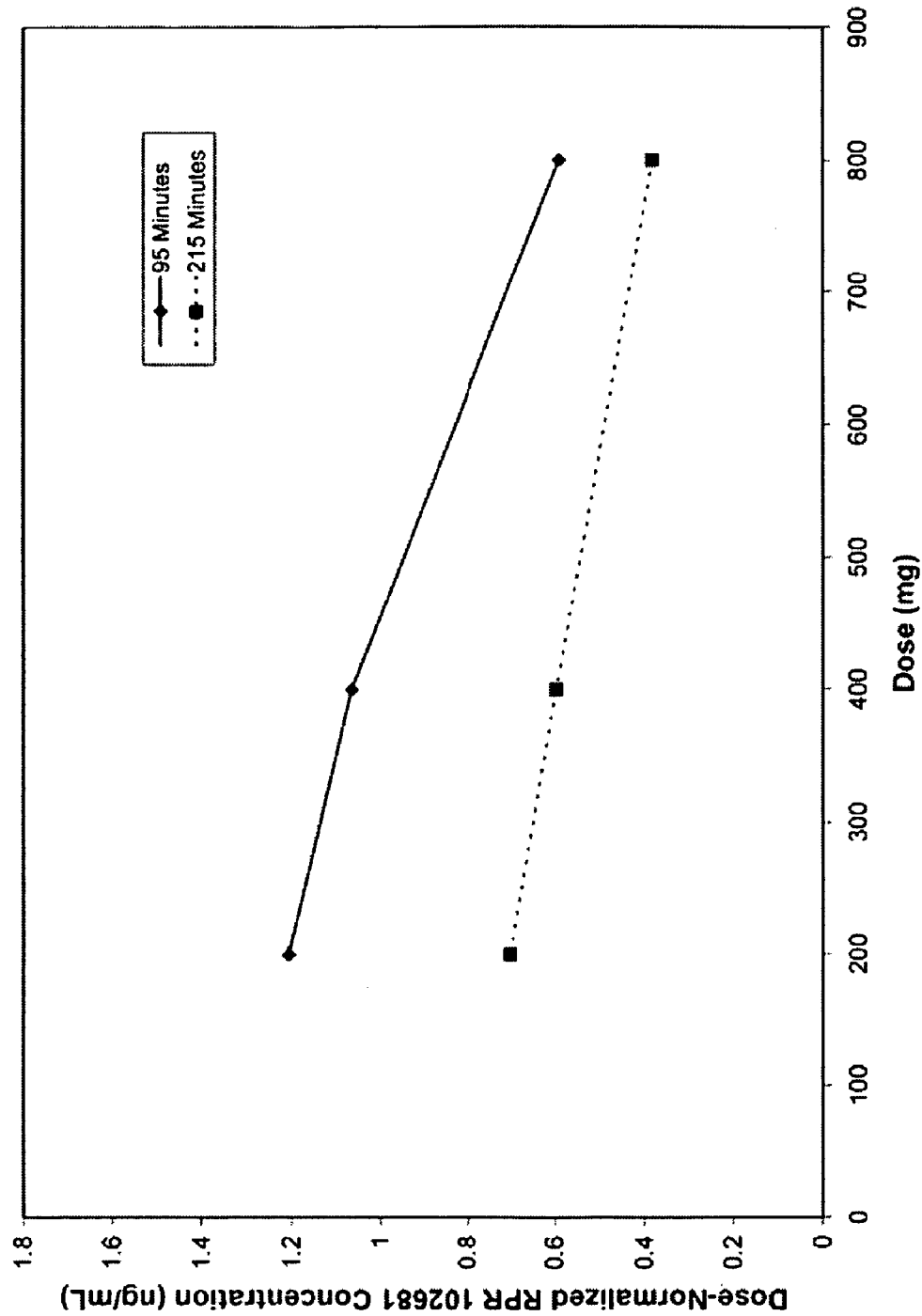
FIG. 17 is a graphical depiction of least-squares means of dose-normalized RPR 102681 concentration at each dose level for the RPR 102681 groups.

FIG. 17 displays the least-squares means versus doses, graphically depicting the least-squares means of dose-normalized RPR 102681 concentration at each dose level for the RPR 102681 groups (●=95 minutes, ■=215 minutes). If the kinetic is linear, the dose-normalized concentrations should remain at the same level for all doses. It is apparent that significant deviation from linearity occurred at the dose range from 400 mg to 800 mg. The most likely explanation is that absorption of RPR 102681 between the 400 and 800 mg doses is saturable or is slow, possibly due to its low solubility (less than 1 mg/mL at pH less than 6) and/or dissolution. However, enhancement of clearance at the 800 mg cannot be ruled out from these data.

Prolactin Study

Serum prolactin data was collected once on day 0 and at −120, 30, 90 minutes on 40 mg cocaine infusion days 15, 22, and 29. FIG. 18 shows a comparison between day 0 and each of the pre-infusion measurements on days 15, 22, and 29. There were no significant differences in serum prolactin levels between RPR 102681 and placebo subjects on any day. There was also no significant change from day 0 to pre infusion measurements except for placebo subjects on day 29. Subjects in placebo group have a relatively higher prolactin value compared to their levels on day 0.

To evaluate subjects' response to infusion, measurements after saline or cocaine infusion were compared to those prior to any infusion (measurement at −120 min). FIG. 19 shows the average prolactin level as well as average change from pre infusion baseline by study day, time point and group. Serum prolactin level decreased significantly following either saline or cocaine infusion in all subjects. There was no significant difference between RPR 102681 and placebo subjects in response to cocaine or saline infusion on any of the infusion days.

FIGS. 20 and 21 further compare prolactin values post-cocaine infusion to post-saline infusion. FIG. 21 graphically depicts data comparing prolactin values post cocaine infusion to post saline infusions (-●-●-=RPR, --○--○--=Placebo). FIG. 21 graphically depicts data comparing prolactin values post cocaine infusion to post saline infusions (-●-●-=RPR, --○--○--=Placebo). No significant differences were observed except for subjects in the RPR 102681 group on day 29 where the post-cocaine prolactin value was significantly lower than post-saline value. This is likely of no importance, and the significance would disappear if corrections were made for multiple comparisons.

Imaging Study

Figure 22A:
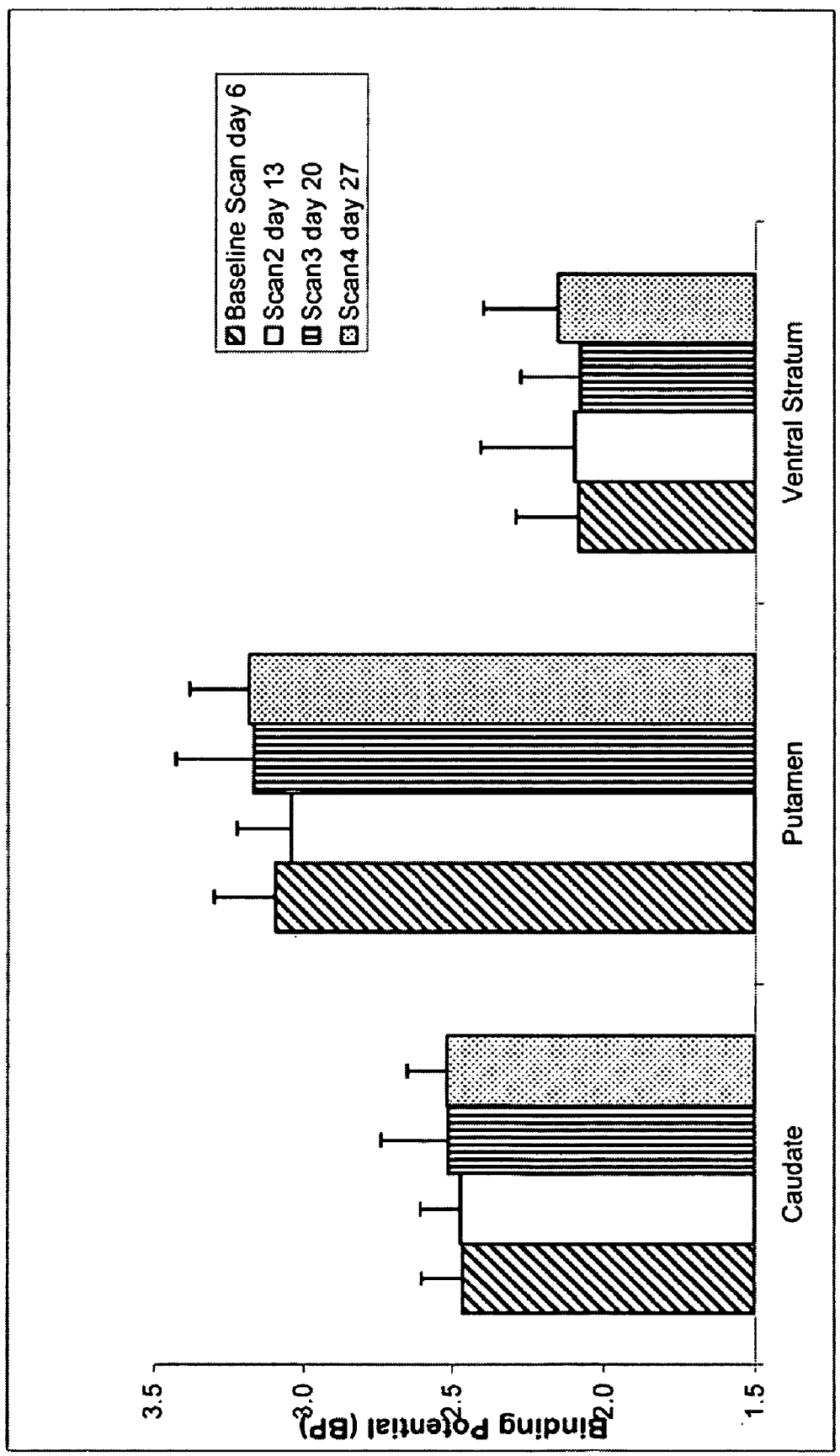
FIG. 22A is a graphical depiction of binding potential estimates (Mean and Standard Error) by PET after the administration of [$^{11}$C]-raclopride for five cocaine users at weekly intervals for four weeks of treatment with placebo.

FIG. 22A shows binding potential (BP) estimates (mean and standard error) by PET scan after the administration of [$^{11}$C]-raclopride for five cocaine users at weekly intervals for five cocaine users at weekly intervals for four weeks of treatment with placebo (▨=Baseline Scan day 6, □=Scan 2 day 13, ▥=Scan 3 day 20, ▤=Scan 4 day 27). As expected, no statistically significant change was observed in the binding potential in caudate nucleus, putamen or ventral striatum while using placebo.

Figure 22B:
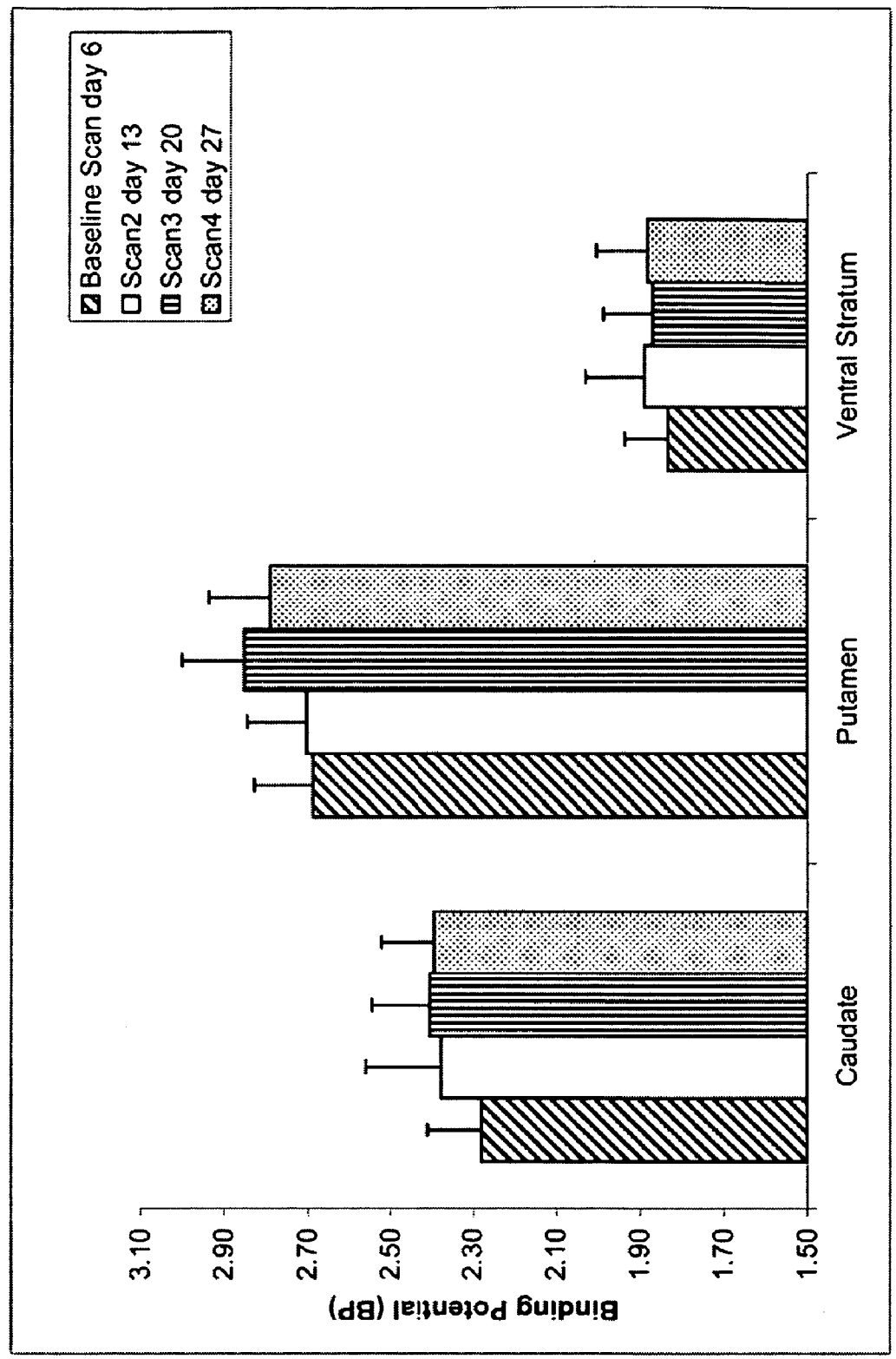
FIG. 22B is a graphical depiction of binding potential estimates (mean and standard error) by PET after the administration of [$^{11}$C]-raclopride for seven cocaine users at weekly intervals for four weeks of treatment with RPR 102681 orally.

FIG. 22B shows BP estimates (mean and standard error) by PET scan after the administration of [$^{11}$C]-raclopride for seven cocaine users at weekly intervals for four weeks of treatment with RPR 102681 orally at 6 A.M. and 5 P.M., 200 mg on days 9-15, 400 mg on days 16-22, and 800 mg on days 23-29 (Dosing Schedule A) (▨=Baseline Scan day 6, □=Scan 2 day 13, ▥=Scan 3 day 20, ▤=Scan 4 day 27). Under Dosing Schedule A, where subjects were dosed in the morning at 6 A.M. on the PET scan day, no statistically significant change in BP was seen in caudate nucleus, putamen or ventral striatum.

Figure 22C:
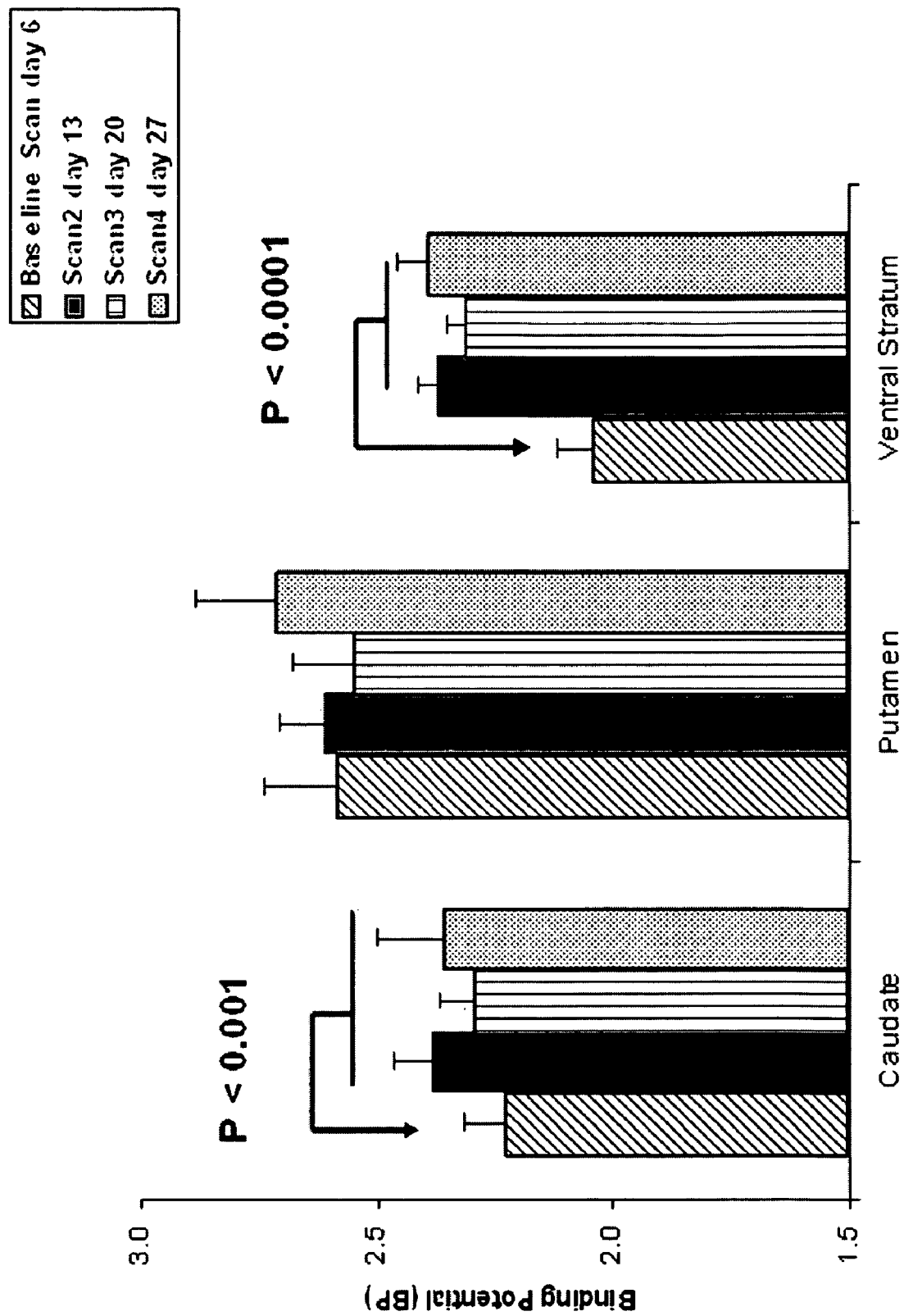
FIG. 22C is a graphical depiction of binding potential estimates (mean and standard error) by PET after the administration of [$^{11}$C]-raclopride for four cocaine users at weekly intervals for four weeks of treatment with RPR 102681 orally.

FIG. 22C shows the BP estimates (mean and standard error) by PET after the administration of [$^{11}$C]-raclopride for four cocaine users at weekly intervals for four weeks of treatment with RPR 102681 orally at 6 A.M. and 5 P.M., 200 mg on days 9-15, 400 mg on days 16-22, and 800 mg on days 23-29 (Dosing Schedule B) (▨=Baseline Scan day 6, ▩=Scan 2 day 13, ▥=Scan 3 day 20, ▤=Scan 4 day 27). On the days of PET scans the second dose was administered one or one and half hours before the start of the PET scan instead of at 5 P.M. As shown in FIG. 22C, RPR 102681 administration significantly increased BP in the caudate nucleus and ventral striatum under Dosing Schedule B, where an additional dose of RPR 102681 was given 60-90 minutes prior to the PET scan (P<0.001).

MRI and PET scan images of the ventral striatum and caudate nucleus, measuring BP after administration of [$^{11}$C]-raclopride, have shown an increased isotope signal following dosing with RPR 102681 which is indicative of decreased dopamine release in these areas.

FIG. 23 show plasma concentrations of RPR 102681 in ng/mL for twelve cocaine users at weekly intervals on days 6, 13, 20, and 27, for four weeks of treatment with RPR 102681 administered orally twice daily, 200 mg on days 9-15, 400 mg on days 16-22, and 800 mg on days 23-29 (Dosing Schedules A and B). Plasma samples were drawn at the midpoint of 90-minute PET scan after the intravenous administration of [$^{11}$C]-raclopride on days 6, 13, 20, and 27.

Figure 24:
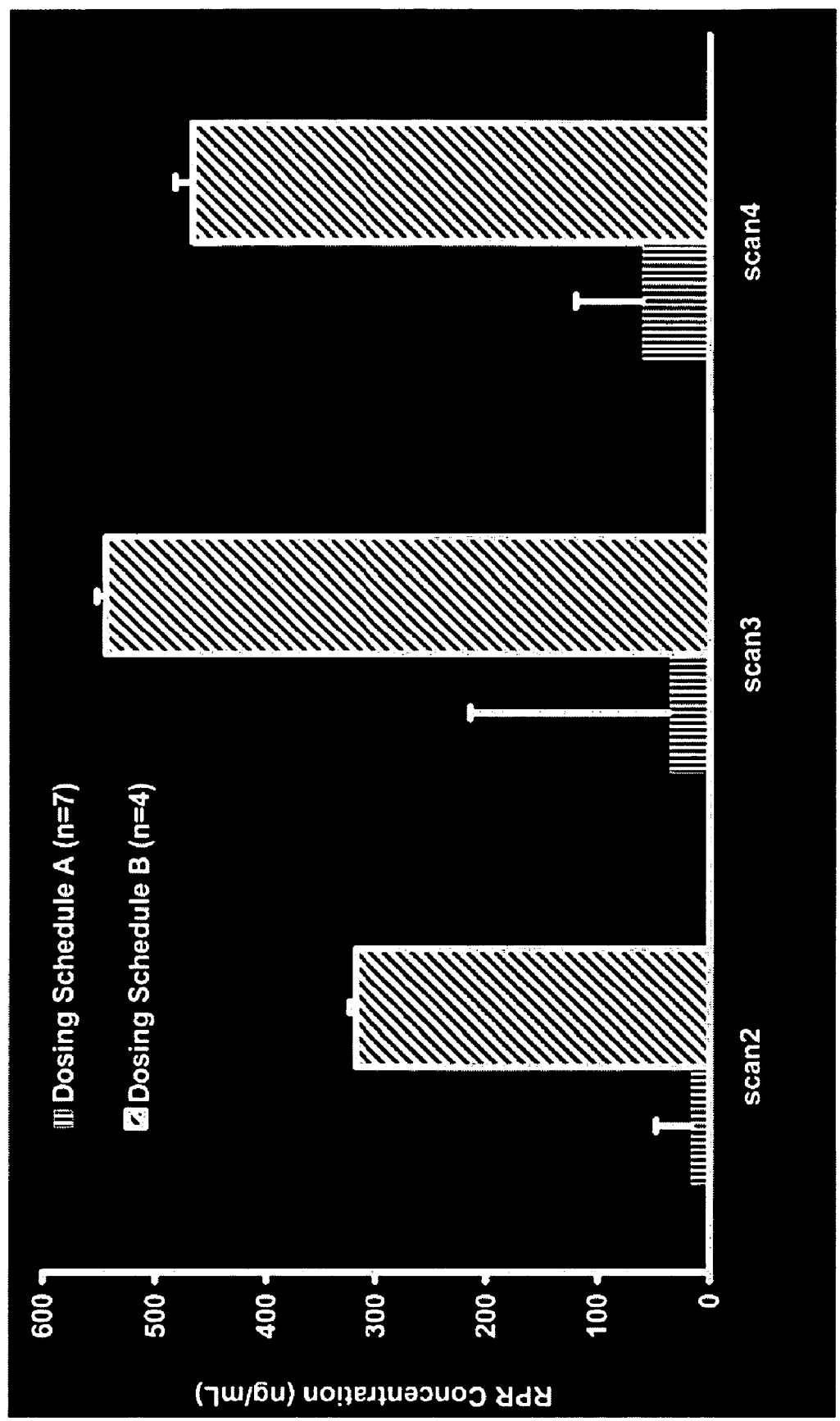
FIG. 24 is a graphical depiction of plasma concentrations (mean and standard error) of RPR 102681 of twelve cocaine users at the midpoints during positron PET after the administration of [$^{11}$C]-raclopride of weekly intervals (Days 6, 13, 20, and 27) for four weeks of treatment with RPR 102681 orally at 6 AM and 5 PM, 200 mg on days 9-15, 400 mg on days 16-22, and 800 mg on days 23-29.

FIG. 24 further compares the results of plasma concentrations (mean and standard error) of RPR 102681 of twelve cocaine users in Dosing Schedules A and B. The plasma concentrations were measured at the midpoints during PET scan after the administration of [$^{11}$C]-raclopride of weekly intervals (Days 6, 13, 20, and 27) for four weeks of treatment with RPR 102681 orally at 6 A.M. and 5 P.M., 200 mg on days 9-15, 400 mg on days 16-22, and 800 mg on days 23-29. For the four participants with Dosing Schedule B only, on the days of PET scans the second dose was administered one or one and half hours before the start of the PET scan instead of at 5 P.M.

FIG. 25 shows the plasma prolactin concentrations and RPR 102681 concentrations and BP estimates by PET scan after the administration of [$^{11}$C]-raclopride for six cocaine users at weekly intervals on days 6, 13, 20, and 27, for four weeks of treatment with RPR 102681 orally twice daily at 6 A.M. and 5 P.M., 200 mg on days 9-15, 400 mg on days 16-22, and 800 mg on days 23-29 (Dosing Schedules A). The baseline prolactin samples were obtained at variable times before the start of the study.

The study prolactin samples were drawn on days 15, 22, and 29. As shown in FIG. 25, the change in prolactin levels correlated positively with the change in the BP, but only within a subset of subject who were dosed under Dosing Schedule A (N=7). Interestingly, this correlation was not found under Dosing Schedule B, where the significant increase in BP and higher prolactin plasma levels was observed.

FIGS. 26A and B show the percent change in BP plotted against RPR 102681 plasma concentration for those subjects who received RPR 102681 doses under Dosing Schedule A and B, respectfully. FIG. 26A graphically plots % BP change against RPR 102681 plasma concentration for those subjects who received RPR 102681 doses under Dosing Schedule A (♦=Caudate, □=Putamen, ▲=Ventral Striatum (VS)). As shown in FIG. 26A, no significant relationship was observed for subjects dosed under Dosing Schedule A. FIG. 26A graphically plots % BP change against RPR 102681 plasma concentration for those subjects who received RPR 102681 doses under Dosing Schedule B ((♦=Caudate, □=Putamen, ▲=Ventral Striatum (VS)). As shown in FIG. 26B, for those subjects dosed under Dosing Schedule B, there is also no significant correlation, however, the caudate and putamen show a slight trend.

Discussion

Phase I, Double-Blind, Placebo-Controlled Dose Escalating Assessment of Potential Interaction between Cocaine and RPR 102681 in Humans Primary Outcome Measures All vital signs increased after cocaine infusion and greater responses were observed for higher cocaine dose. There was no statistical difference between RPR 102681 and placebo groups prior to infusions, post saline or post cocaine infusions on any day for all three measures. As expected, cocaine at both doses induced significant elevation in HR/SBP/DBP (most P-values<0.05) and its effect was more notable in the RPR 102681 group. Compared to the placebo group, the RPR 102681 group experienced significantly greater SBP increase in response to cocaine 20 mg. Furthermore, there was a decreasing trend with higher RPR 102681 doses for HR/SBP after cocaine 40 mg in the RPR 102681 group and DBP after cocaine 20 mg.

The ECG study results showed the mean values for VR, PR, QT, RR and QRS were within normal range for each domain. PR/RR/QT duration in the RPR 102681 group seemed to decrease following cocaine 40 mg infusion. However, the statistical significance might not hold if multiplicity adjustment was performed in these multiple comparisons and the changes were all within normal ranges and were not clinically significant.

Secondary Outcome Measures

Pharmacokinetics Parameters

The overall results of the analyses of cocaine and BE pharmacokinetic parameters at baseline and after 200 mg, 400 mg and 800 mg treatment of either placebo or RPR 102681 showed no evidence that the administration of RPR 102681 alters the pharmacokinetics of cocaine. There was a large intersubject variability in the plasma concentrations of RPR 102681. The data suggest that plasma concentrations of RPR 102681 around the peak times are not proportional to dose at the dose range from 400 mg to 800 mg, and this reflects RPR 102681 PK nonlinearity, probably related to absorption.

Prolactin Study

Serum prolactin level decreased following cocaine or saline infusions. There were no significant differences between the RPR and placebo groups in response to infusion.

Imaging Study

The main result of the PET scan study is the significant increase in BP correlating with RPR treatment. The results show that RPR 102681 is significantly associated with an increase in binding potential in the ventral striatum and caudate nucleus, which is discrepant with findings from animal models. An increase in BP may be due to decreased intrasynaptic dopamine or an affinity change. Although significant correlations were found between prolactin levels and the BP difference, the results were only seen in a subgroup of the subjects scanned under dosing schedule A (n=7).

Unexpected Results

According to research considered by the NIH study, animal data had demonstrated that intraperitoneal administration of RPR 102681 stimulates dopamine release in the ventral striatum (measured by microdialysis), and at the highest dose tested (20 mg/Kg), the release of dopamine is almost tripled compared to baseline values. However, the NIH study showed the opposite effects in humans. It showed that RPR 102681 inhibited dopamine release as evidenced by increasing binding potential of the PET ligand $^{11}$C raclopride in PET brain imaging study.

Therefore, contrary to the teachings of the prior art, namely the animal studies and the U.S. Pat. No. 6,150,387, the PET scan study with the Dosing Schedule B revealed that RPR 102681 decreases intrasynaptic dopamine levels in the striatum. This result is entirely unexpected as prior studies of other compounds within its family described in U.S. Pat. No. 6,150,387 taught that opposite effects should be expected. Thus, RPR 102681 was shown to be dopamine antagonist-like and an unfavorable candidate for the treatment of cocaine addition, and thus may also be ineffective for the treatment of other conditions suggested in the '387 patent.

While the unexpected results demonstrated that RPR 102681 is most likely ineffective for treating disorders in which dopamine up-regulation may be beneficial, the inventor discovered that the likely biological mechanism of RPR 102681 would be applicable to the treatment of schizophrenia. Specifically, by reducing dopamine release by CCK-B receptor antagonism with a benign adverse effect profile, the compound appears well suited to treat a suspected mechanism of schizophrenia.

According to the NIH study, RPR 102681 was safely administered to humans with no serious adverse events observed in the two clinical studies conducted in France by Caplain in 1997 and 1998, and two studies conducted by the NIH. The principal adverse events in the first clinical study with RPR 102681 were postural hypotension (6 occurrences), headaches (3 occurrences), somnolence (3 occurrences), diarrhea (2 occurrences), and euphoria (2 occurrences). The most frequent adverse events observed in the second clinical study with RPR 102681 were flatulence (4 occurrences), pharyngitis (4 occurrences), and headache (1 occurrence).

Since human tolerance of RPR 102681 has been demonstrated, the compound is believed to hold significant promise as a schizophrenia treatment. Further, dosing studies performed during its study as a cocaine cessation agent have revealed a dosing schedule expected to be effective in schizophrenia patients.

The dose and administration embodiments disclosed herein are based upon the human trials described herein and on the inventor's expertise. Further refinement of dosing schedules may result in modifications within the ranges described herein.

While the full investigation of the mechanism by which RPR 102681 acts as a CCK-B receptor antagonist has not been accomplished, it is believed that the compound of formula (I) presynaptically modulates the release of dopamine in the striatum. Other currently available antipsychotic medications block postsynaptic dopamine receptor. Furthermore, while most antipsychotics mainly improve positive symptoms with minimal or no effect on negative symptoms and/or cognition, RPR 102681 may be used to improve negative symptoms and cognition in schizophrenia. The unexpected findings that RPR 102681 reduces dopamine levels in the ventral striatum and caudate nucleus and its safety and benign adverse effect profiles in humans make this a desirable compound for treating schizophrenia.

Prophetic Example

The following is a prophetic example showing the effects of RPR 102681 versus placebo in patients suffering with schizophrenia:

Methods

The following two studies are designed to study the effects of RPR102681 on humans who show schizophrenia symptoms.

Study 1:

This will be a four (4) week, inpatient study of the effects of RPR 102681 on human patients with relapsed schizophrenia symptoms.

This study will establish the efficacy and safety of RPR 102681 as the sole treatment for schizophrenia.

Patients will be admitted to an inpatient unit. After baseline assessments, patients will be randomized to RPR 102681 or placebo.

RPR 102681 dose will follow a flexible schedule range 400-1600 mg/day administered orally twice daily.

Selected patient will be healthy with no significant medical illness that will warrant excluding them form the study (e.g. Hypertension, diabetes, seizure disorder, HIV, etc.).

Baseline assessments will include positive and negative symptoms scale (PANSS) at baseline and weekly, Cognitive functions scale (Matrix) at baseline and at the end of the study (week 4), Angus Simpson scale for extra pyramidal side effects (EPS).

PET brain imaging scans at baseline, and at the end of the study (week 4) using $^{11}$C-raclopride to document associated changes in dopamine turnover.

Serum prolactin levels will be assessed at baseline and end of the study (week 4) to document any changes in prolactin that may be associated with RPR 102681 treatment.

Primary and secondary outcome measures will be assessed.

Primary outcomes: Patients in the RPR 102681 group will show significant improvement in positive symptoms compared to those in the placebo group.

Secondary outcomes: (a) Patients in the RPR 102681 group will show better improvement in negative symptoms of schizophrenia as compared to those in the placebo group; (b) patients in the RPR 102681 group will show improved cognitive functions as compared to those in the placebo group; (c) patients in the RPR 102681 group will show decreased dopamine release as evidenced by increased binding of the radioligand $^{11}$C-raclopride in the ventral striatum and basal ganglia as compared to those in the placebo group; (d) patients in the RPR 102681 group will show minimal or no change in prolactin from baseline commensurate with the changes in dopamine levels; (e) the safety of RPR 102681 vs. placebo will be compared including the incidence of adverse and serious events.

Following the completion of week four assessments, patients will be restarted on their previous medications, stabilized and discharged. Follow up appointment 4 weeks later will be scheduled.

Study 2:

This study will assess the safety and efficacy of RPR 102681 in combination with atypical antipsychotics for the treatment of schizophrenia.

40 outpatients with DSM-IV diagnosis of schizophrenia will be recruited. Following baseline and screening assessments, 20 will be randomized to RPR 102681 group and 20 to placebo group. This will be a 6 week study. Accordingly, RPR 102681 will be administered in a flexible dosing schedule based on tolerability (dose range 400-1600, administered in divided does twice daily).

Assessments will include positive and negative symptoms scale (PANSS) at baseline and weekly, Cognitive functions scale (Matrix) at baseline and end of study (week 6), Angus Simpson scale for extra pyramidal side effects (EPS) at baseline and weekly.

Primary and secondary outcome measures will be assessed.

Primary outcomes: Patients in the RPR 102681 group will show significant improvement in positive symptoms as compared to those in the placebo group.

Secondary outcomes: (a) Patients in the RPR 102681 group will show better improvement in negative symptoms of schizophrenia as compared to those in the placebo group; (b) Patients in the RPR 102681 group will show improvement in cognitive functions as compared to those in the placebo group; (c) The safety of RPR 102681 vs. placebo will be compared including the incidence of adverse and serious events.

Following the completion of the treatment period (end of week six) patients will have a follow up visit four weeks later.

Results

Based upon inventor's expertise it is believed that the prophetic tests will reveal that RPR 102681 will have efficacy in treating positive symptoms as well as improving negative and cognitive symptoms of schizophrenia by itself and in combination with another antipsychotic medication. The inventor also believes that the tests will reveal changes in brain imaging studies consistent with findings in the above described tests, indicating a decreased dopamine release in the ventral striatum and caudate nucleus. The inventor also believes that the tests will reveal that RPR 102681 will have a favorable side effects profile and no major or serious adverse events. Finally, the inventor also believes that the tests will reveal that RPR 102681 will cause minimal or no change in prolactin, weight and BMI.

Conclusions

RPR 102681 is a medication with a unique mechanism of action different form all other marketed antipsychotic drugs and offers new hope for patients with schizophrenia. It can be used alone or in combination with other antipsychotic drugs to synergize their effects. Unlike other available antipsychotics, RPR 102681 possesses a very favorable safety profile with no evidence of causing EPS, weight gain, or metabolic effects.

The foregoing description of the various embodiments is provided to enable any person skilled in the art to make or use the present invention. Various modifications to these embodiments are well known in the art, will be readily apparent to those skilled in the art, and the generic principles defined herein may be applied to other embodiments without departing from the spirit or scope of the invention. Thus, the present invention is not intended to be limited to the embodiments shown herein, and instead the claims should be accorded the widest scope consistent with the principles and novel features disclosed herein.

I claim:
1. A method for treating schizophrenia comprising the administration of a compound of formula (I)

or a physiologically acceptable salt thereof to a human diagnosed as having schizophrenia, the compound being administered in an amount effective to treat at least one symptom of schizophrenia; wherein the at least one symptom of schizophrenia comprises hallucinations, delusions, anhedonia, poverty of speech, cognitive impairment, or a combination thereof.

2. The method of claim 1 wherein the compound of formula (I) or the physiologically acceptable salt thereof is administered orally.

3. The method of claim 1 wherein a capsule containing the compound of formula (I) is orally administered.

4. The method of claim 1 wherein a tablet containing the compound of formula (I) is orally administered.

5. The method of claim 2 wherein an aqueous solution containing the compound of formula (I) is orally administered.

6. The method of claim 2 wherein an aqueous suspension containing the compound of formula (I) is orally administered.

7. The method of claim 1 wherein the physiologically acceptable salt thereof is alkali metal, alkaline earth or ammonium salt.

8. The method of claim 1 wherein the effective amount is 200 to 1600 mg of the compound of formula (I).

9. The method of claim 1 wherein the compound of formula (I) or the physiologically acceptable salt thereof is administered topically.

10. The method of claim 1 wherein a transdermal patch containing the compound of formula (I) is topically administered.

11. A pharmaceutical composition in unit dosage form for treating schizophrenia comprising per dosage unit 800 to 1600 mg of a physiologically acceptable salt of a compound of formula (I)

with a pharmaceutically acceptable carrier in solid or liquid form.

12. A method for decreasing dopamine levels in basal ganglia comprising administrating a compound of formula (I)

or physiologically acceptable salt thereof to a human diagnosed as having schizophrenia, the compound being administered in an amount effective to decrease dopamine levels in basal ganglia of the human.

13. The method of claim 12 wherein the compound of formula (I) or the physiologically acceptable salt thereof is administered orally.

14. The method of claim 13 wherein a capsule containing the compound of formula (I) is orally administered.

15. The method of claim 13 wherein a tablet containing the compound of formula (I) is orally administered.

16. The method of claim 13 wherein an aqueous solution containing the compound of formula (I) is orally administered.

17. The method of claim 13 wherein an aqueous suspension containing the compound of formula (I) is orally administered.

18. The method of claim 13 wherein the physiologically acceptable salt thereof is alkali metal, alkaline earth or ammonium salt.

19. The method of claim 13 wherein the effective amount is 200 to 1600 mg of the compound of formula (I).

20. The method of claim 1, further comprising first diagnosing the human with schizophrenia before administration of the compound of formula (I) or the physiological acceptable salt thereof.

21. The method of claim 1, further comprising first identifying at least one symptom of schizophrenia in the human before administration of the compound of formula (I) or the physiological acceptable salt thereof.

22. The method of claim 21, wherein the at least one symptom of schizophrenia comprises hallucinations, delusions, anhedonia, poverty of speech, cognitive impairment, or a combination thereof.

23. The method of claim 12, further comprising first diagnosing the human with schizophrenia before administering the compound of formula (I) or the physiological acceptable salt thereof.

24. The method of claim 12, further comprising first identifying at least one symptom of schizophrenia in the human before administering the compound of formula (I) or the physiological acceptable salt thereof.

25. The method of claim 24, wherein the at least one symptom of schizophrenia comprises hallucinations, delusions, anhedonia, poverty of speech, cognitive impairment, or a combination thereof.

\* \* \* \* \*